United States Patent [19]

Asai

[11] 4,294,757
[45] Oct. 13, 1981

[54] 20-O-ACYLMAYTANSINOIDS

[75] Inventor: Mitsuko Asai, Takatsuki, Japan

[73] Assignee: Takeda Chemical Industries, Ltd, Osaka, Japan

[21] Appl. No.: 112,237

[22] Filed: Jan. 15, 1980

[30] Foreign Application Priority Data

Jan. 31, 1979 [JP] Japan ................................ 54-10551

[51] Int. Cl.³ .......................................... C07D 498/18
[52] U.S. Cl. ......................... 260/239.3 P; 424/248.54
[58] Field of Search ................................. 260/239.3 P

[56] References Cited

U.S. PATENT DOCUMENTS

| | | | |
|---|---|---|---|
| 3,631,176 | 12/1971 | Klopping | 548/306 |
| 3,770,775 | 11/1973 | Paolo et al. | 260/343.21 |
| 3,829,437 | 8/1974 | Zumach et al. | 549/30 |
| 3,896,111 | 7/1975 | Kupchan et al. | 260/239.3 P |
| 4,137,230 | 1/1979 | Hashimoto et al. | 260/239.3 P |
| 4,190,580 | 2/1980 | Hashimoto et al. | 260/239.3 P |

FOREIGN PATENT DOCUMENTS 2017101  10/1979  United Kingdom ......... 260/239.3 P

OTHER PUBLICATIONS

CA. 1972-1976 Chem. Substance Index, 13927 CS, MBR 5601.

Kupchan et al., J.A.C.S., vol. 97, No. 18, 1975.
Kupchan et al., Jour. Medicinal Chem., 1978, vol. 21, No. 1.

Primary Examiner—Henry R. Jiles
Assistant Examiner—Jane T. Fan
Attorney, Agent, or Firm—Wegner & Bretschneider

[57] ABSTRACT

Novel 20-demethoxy-20-acyloxymaytansinoids representable by the formula:

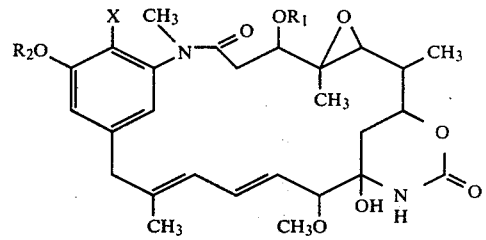

[wherein X is chlorine or hydrogen; $R_1$ is hydrogen or acyl group; $R_2$ is acyl group] are produced from 20-demethoxy-20-hydroxymaytansinoids by means of acylation.

The compounds are useful as antifungal, antiprotozoal or antitumor agent.

37 Claims, No Drawings

20-O-ACYLMAYTANSINOIDS

The present invention relates to a 20-0-acylmaytansinoid compound, the methoxy group at the 20-position of a maytansinoid compound being substituted by an acyloxy group, and to a method for producing the 20-0-acylmaytansinoid compound.

After extensive research undertaken to develop a method for producing a variety of useful compounds with the use as the starting compounds of a maytansinoid compound which has been demethylated in the 20-position by a culture broth, or a processed matter of the culture broth, of a microorganism, or the corresponding compound with a hydroxy group in the 3-position obtained through further deacylation of the resulting 20-demethylated maytansinoid compound, the present inventors found that acylation of the said starting compounds yields a maytansinoid compound, the 20-and 3-positions of which have been substituted by different acyloxy groups, and further research conducted based on this led to completion of the present invention.

In this application, meanwhile, 20-demethoxy-20-acyloxymaytansinoid compound is sometimes referred to briefly as 20-0-acylmaytansinoid compound.

The present invention is directed to: (1) a 20-0-acylmaytansinoid compound (I) of the general formula

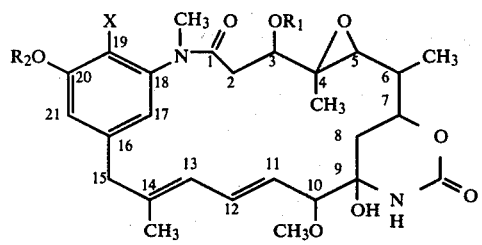

[wherein X is chlorine or hydrogen; $R_1$ is hydrogen or acyl group; $R_2$ is acyl group] and, (2) a method for producing a 20-0-acylmaytansinoid compound (I) which comprises subjecting a demethylmaytansinoid compound (II) of the general formula:

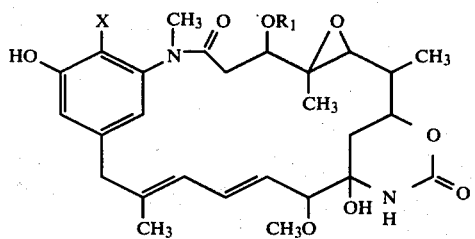

[wherein X and $R_1$ are as respectively defined above] to acylation.

In the present specification, "demethyl" stands for the abbreviation of "20-demethoxy-20-hydroxy", "dechloro" means "19-dechloro" and the compound (II) wherein $R_1$ is —COCH(CH$_3$)$_2$ and X is chlorine will be hereinafter referred to as PDM-3, the compound (II) wherein $R_1$ is —CO(CH$_2$)$_2$—CH$_3$ and X is Cl will be referred to as PDM-3', and the compound (II) wherein $R_1$ is —COCH$_2$—CH(CH$_3$)$_2$ and X is chlorine will be referred to as PDM-4.

Referring to the general formulas described hereinbefore, the acyl group represented by $R_1$ and $R_2$ is the same or different one, and each is an acyl group derived from a carboxylic acid, carbamic acid derivative or organic carbonic acid derivative having a molecular weight of no more than about 300 or an acyl group containing 1 to 20 carbon atoms. The term "acyl group" encompasses, among others, saturated and unsaturated aliphatic acyl groups; saturated or unsaturated alicyclic acyl groups; aromatic acyl groups; saturated or unsaturated heterocyclic acyl groups; N-acyl-α-amino acid type acyl groups; carbamoyl type acyl groups; and carbonate type acyl groups.

Thus, such acyl groups may for example be the groups represented by the formula:

—CO—R$_3$     (III)

(wherein $R_3$ is hydrogen or an optionally substituted or unsubstituted alkyl, alkenyl, cycloalkyl, cycloalkenyl, aryl or heterocyclic group, said cycloalkyl, cycloalkenyl, aryl and heterocyclic group being optionally attached to the carbonyl carbon through an alkylene chain), the groups designated by the formula:

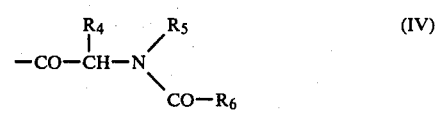

(wherein $R_4$ is hydrogen or an optionally substituted or unsubstituted alkyl, cycloalkyl, aryl, indolyl or imidazolyl group, said cycloalkyl, aryl, indolyl or imidazolyl group being optionally attached to the alpha-carbon atoms through an alkylene chain; $R_5$ is hydrogen or an optionally substituted or unsubstituted alkyl, cycloalkyl, cycloalkylalkyl, aryl or benzyl group; $R_6$ is hydrogen, alkoxy, bornyloxy, isobornyloxy, benzyloxy or an optionally substituted or unsubstituted alkyl, alkenyl, cycloalkyl, cycloalkenyl, aryl or heterocyclic group, said cycloalkyl, cycloalkenyl, aryl and heterocyclic group being optionally attached to the carbonyl carbon atom adjacent the nitrogen atom through an alkylene chain), the groups represented by the formula:

(wherein $R_7$ and $R_8$ may be the same or different and each is hydrogen or an optionally substituted or unsubstituted hydrocarbon residue or heterocyclic group, $R_7$ and $R_8$ optionally forming a heterocyclic group as taken together with the adjacent nitrogen atom), or the groups represented by the formula:

—CO—O—R$_9$     (VI)

(wherein $R_9$ is an optionally substituted or unsubstituted hydrocarbon residue).

When the acyl groups represented by $R_1$ and $R_2$ as hereinbefore described are a group having the formula:

—CO—R$_3$     (III)

(wherein $R_3$ is as defined hereinbefore), the alkyl groups as represented by $R_3$ may be for example an alkyl group having 1 to 18 carbon atoms (e.g. methyl, ethyl, propyl, isopropyl, butyl, isobutyl, sec-butyl, tert-butyl, pentyl, isopentyl, 1-methylpropyl, hexyl, isohexyl, heptyl, 3-heptyl, octyl, nonyl, decyl, undecyl, dodecyl, tridecyl, tetradecyl, pentadecyl, hexadecyl, heptadecyl, octadecyl, 1,2-dimethylpropyl, 1-ethylpropyl, 1,2,2-trimethylpropyl, 1-propylbutyl, 2-ethylhexyl, etc.), although alkyl groups having 1 to 6 carbon atoms are preferable.

Preferred examples of the alkenyl group designated by $R_3$ are alkenyl groups having 2 to 18 carbon atoms (e.g. vinyl, allyl, 1-methyl-vinyl, 2-methyl-vinyl, 1-octenyl, 1-decenyl, 1,3-pentadienyl, oleyl, etc.), with alkenyls of 2 to 4 carbon atoms being particularly desirable.

As examples of the cycloalkyl group represented by $R_3$, there may be mentioned cycloalkyl groups of about 3 to 10 carbon atoms (e.g. cyclopropyl, cyclobutyl, cyclopentyl, cyclohexyl, cycloheptyl, cyclooctyl, norbornyl, adamantyl, etc.) to which a benzene ring may be fused (e.g. 1- or 2-indanyl, benzocyclobutyl, etc.).

As examples of the cycloalkenyl group designated by $R_2$ there may be mentioned cycloalkenyl groups of 3 to 10 carbon atoms (e.g. 1-cyclobutenyl, 1-, 2- or 3-cyclopentenyl, 1-, 2- or 3-cyclohexenyl, 4-cycloheptenyl, 4-cyclooctenyl, 1,4-cyclohexadienyl, 4-norbornenyl, 2,4,6-cycloheptatrienyl, etc.).

The aryl group represented by $R_3$ may for example be phenyl, α- or β-naphthyl or the like, although phenyl is especially desirable.

Examples of the heterocyclic group designated by $R_3$ include a 4-, 5- or 6-membered heterocyclic group containing N, O or/and S, which may be saturated or unsaturated and may have a benzene ring fused thereto. As examples of such N-containing 4-, 5- or 6-membered heterocyclic group, there may be mentioned azetidinyl, pyridyl (e.g. 2-, 3- or 4-pyridyl), 1,2,3,4-tetrahydropyridyl, piperidyl, quinolyl, 1,2-dihydroquinolyl, 3- or 4-isoquinolyl, 1,2-dihydroisoquinolyl, pyrrolyl, pyrrolinyl, pyrrolidinyl, indolyl, etc. The oxygen-containing 5- or 6-membered heterocyclic group may for example be furyl, pyranyl, dihydropyranyl, benzofuryl, benzopyranyl, etc., while the sulfur containing 5- or 6-membered heterocyclic group may for example be thienyl, benzothienyl, or the like. The above heterocyclic groups may each include 2 to 4 heteroatoms, which may be the same or different, such as N, O or/and S. As examples of such heterocyclic groups, there may be mentioned imidazolyl, pyrazolyl, pyrazinyl, pryimidinyl, pyridazinyl, 2-imidazolyl, imidazolidinyl, benzoimidazolyl, indazolyl, quinoxalyl, quinazolinyl, cinnolinyl, 1,4-dioxanyl, 1,4-benzodioxanyl, 1,2- or 1,3-dithiolanyl, 1,3-dithianyl, isooxazolyl, oxazolyl, morpholinyl, benzoisooxazolyl, benzooxazolyl, isothiazolyl, thiazolyl, benzoisothiazolyl, benzothiazolyl, benzothiazinyl, 1,2,4-, 1,2,5- or 1,3,4-oxadiazolyl, 1,2,3- 1,2,4-, 1,2,5- or 1,3,4-thiadiazolyl, 1,2,3-, 1,2,5- or 1,3,4-triazolyl, 1,3,5-triazinyl, benzotriazolyl, 1,2,3,4-tetrazolyl, etc. Generally speaking, when said heterocyclic groups are strongly basic groups having an NH group, such as azetidinyl, 1,2,3,4-tetrahydropyridyl, piperidyl, 1,2-dihydroquinolyl, 1,2-dihydroisoquinolyl, pyrrolyl, pyrrolinyl, pyrrolidinyl, pyrazolyl, 2-imidazolinyl, imidazolidinyl, indazolyl, morpholinyl, 1,2,3-, 1,2,5- or 1,3,4-triazolyl, benzotriazolyl, 1,2,3,4-tetrazolyl, etc., it is desirable that a suitable substituent, which will be described hereinafter, be present in the N-position, or an alkylene chain, which will be described hereinafter, be attached to the N-position.

The cyclic group as $R_3$ mentioned above (i.e. said optionally substituted cycloalkyl, cycloalkenyl, aryl and heterocyclic group) may optionally be attached to the carbonyl carbon atom in —CO—$R_3$ of the formula (III) through an alkylene chain. Therefore, when said cyclic group is attached to an alkylene chain, $R_3$ represents an optionally substituted cycloalkylalkyl, cycloalkenylalkyl, aralkyl or heterocyclic alkyl group. The alkylene chain may consist of a straight-chain or branched alkylene group of 1 to 4 carbon atoms (e.g. methylene, ethylene, methylmethylene (ethylidene), propylene, butylene, 1-, 2- or 3-methylpropylene, 1- or 2-ethylethylene, propylmethylene, 1,1- or 1,2-dimethylethylene, isopropylmethylene, etc.). As examples of said cycloalkylalkyl group, there may be mentioned 1-adamantylmethyl, cyclohexylmethyl, 3-cyclohexylpropyl, 2-cyclopentenylmethyl, 2-cyclopentylethyl, cyclopropylethyl, cyclobutylethyl, cyclopentylmethyl, 2-cyclohexylethyl, 2-methyl-cyclohexylpropyl and the like.

As examples of said cycloalkenylalkyl group, there may be mentioned 1-, 2- or 3-cyclopentenylmethyl, 1-, 2- or 3-cyclohexenylmethyl, 4-cycloheptenyl-3-propyl, 1,4-cyclohexadienylmethyl group, and so on.

Examples of said aralkyl group include benzyl, phenethyl, 3-phenylpropyl, α-methylbenzyl, 1-methyl-3-phenylpropyl, 4-phenylbutyl and so on.

As examples of said heterocyclic alkyl group, there may be mentioned 3-indolylmethyl, 3-(3-indolyl)propyl, 2-pyridylmethyl, 3-pyridylmethyl, 4-pyridylmethyl, 3-(2-thienyl)propyl, 2-benzothiazolylmethyl, 2-benzoxazolylmethyl, 3-benzoisothiazolylmethyl, 3-benzoisoxazolylmethyl, furfuryl, 2-thienyl and so on.

When $R_3$ is an N-containing heterocyclic group, with its N atom linked to the carbonyl carbon of the acyl group —CO—$R_3$, the particular heterocyclic group is defined as being always attached to the carbonyl groups through the alkylene chain mentioned above. As examples of such heterocycle-alkyl group with an alkylene group attached to its N atom, there may be mentioned 1-pyrrolylmethyl, 2-oxo-1-pyrrolidinylmethyl, 1-imidazolylmethyl, 3,5-dimethyl-1-pyrazolylmethyl, 1-piperidylethyl (or 1-piperidinoethyl), 4-morpholinylmethyl (or 4-morpholinomethyl), 1-tetrazolylmethyl, 2,5-dioxo-1-pyrrolidinylmethyl, 1,3-dioxo-2-isoindolylmethyl, 2-thioxo-4-oxo-3-thiazolidinylmethyl, 3,5-diiodo-4-oxo-1,4-dihydropyridyl-1-methyl, 4-methyl-1-piperazinylmethyl, 1-indolylethyl and so on.

The alkyl, alkenyl, cycloalkyl, cycloalkenyl, aryl and heterocyclic group $R_3$ may optionally be substituted, the substituents being exemplified by alkoxy groups of 1 to 4 carbon atoms (e.g. methoxy, ethoxy, propoxy, isopropoxy, n-butoxy, iso-butoxy, sec-butoxy, tert-butoxy, etc.), alkanoyl groups of 2 to 4 carbon atoms (e.g. acetyl, propionyl, n-butyryl, iso-butyryl, etc.), alkanoyloxy groups of 2 to 4 carbon atoms (e.g. acetyloxy, propionyloxy, n-butyryloxy, isobutyryloxy, etc.), alkoxycarbonyl groups of 2 to 4 carbon atoms (e.g. methoxycarbonyl, ethoxycarbonyl, n-propoxycarbonyl, isopropoxycarbonyl, etc.), halogens (e.g. chlorine, fluorine, bromine, iodine), nitro, cyano, trifluoromethyl, di-$C_{1-4}$ alkylamino (e.g. dimethylamino, diethylamino, dipropylamino, diisopropylamino, dibutylamino, etc.), $C_{1-4}$ aklylthio (e.g. methylthio, ethylthio, n-propylthio, isopropylthio, n-butylthio, isobutylthio, sec-butylthio, tert-butylthio, etc.), methylsulfinyl, methylsulfonyl, oxo, thioxo, $C_{1-4}$ alkanoylamido (e.g. formamido, acetamido, propionylamino, butyrylamino, isobutyrylamino, etc.), carboxy group of the formula —COOR$_{12}$ [The group R$_{12}$ is hydrogen, C$_{1-6}$ alkyl, aryl or aralkyl. As examples of these groups, there may be mentioned the corresponding groups given for R$_3$], and so on. When R$_3$ is a cyclic group (i.e. cycloalkyl, cycloalkenyl, aryl and heterocyclic group), alkyl groups of 1 to 4 carbon atoms (e.g. methyl, ethyl, n-propyl, isopropyl, n-butyl, isobutyl, sec-butyl, tert-butyl, etc.) may also be mentioned as the substituents. These substituents may be the same or different and may be present in the number of 1 to 3.

The substituted C$_{1-18}$ alkyl group R$_3$ may for example be methoxymethyl, butoxymethyl, methylthiomethyl, methylthioethyl, ethylthioethyl, isopropylthioethyl, butylthioethyl, isobutylthioethyl, acetyloxymethyl, acetyloxyethyl, ethoxycarbonylmethyl, butoxycarbonylethyl, fluoromethyl, chloromethyl, chloroethyl, 3-chloropropyl, 4-chlorobutyl, 3,3,3-trichloropropyl, trifluoromethyl, bromomethyl, 4-bromobutyl, 5-bromopentyl, iodomethyl, 2iodoethyl, 1,1-dimethyl-2,2-dichloroethyl, 2-chloro-1-chloromethyl-1-methylethyl, cyanomethyl, methylsulfinylethyl, methylsulfonylmethyl, and the like.

1-Chlorovinyl may be mentioned as an example of said substituted C$_{2-10}$ alkenyl group R$_3$.

As examples of the substituted cyclo-C$_{3-10}$ alkyl group R$_3$, there may be mentioned 2,2-dimethylcyclopropyl, 2-propylcyclopropyl, 2-butylcyclopropyl, 4-isobutylcyclohexyl, 2-bromocyclopropyl, 2-chlorocyclobutyl, 4-chlorocyclohexyl, 2-iodocyclohexyl, 2,2-difluorocyclobutyl, 3-methoxycyclohexyl, 2,2-dimethyl-3-acetylcylobutyl, 4-acetylcyclohexyl, 2-cyanocyclohexyl, 2-cyanocyclobutyl, 4-cyanocyclohexyl, 4-dimethylaminocyclohexyl and so on.

As examples of substituted cyclo-C$_{3-10}$ alkenyl group R$_3$, there may be mentioned 2-cyano-2-cyclohexenyl, 3,3-dimethyl-4-cyclobutenyl, 4-ethoxycarbonyl-1-cyclohexenyl, 4-butoxycarbonyl-1-cyclohexenyl and the like.

Typical examples of the substituted aryl group R$_3$ are 2-, 3- or 4methylphenyl, 4-tert-butylphenyl, 2-, 3- or 4-chlorophenyl, 2-, 3- or 4-bromophenyl, 2-, 3- or 4-iodophenyl, 2-, 3- or 4-fluorophenyl, 2- or 4-methoxyphenyl, 4-butoxyphenyl, 4-methoxycarbonylphenyl, 3-acetylphenyl, 2-, 3- or 4nitrophenyl, 3- or 4-cyanophenyl, 4-dimethylaminophenyl, 4-diethylaminophenyl, 4-acetoxyphenyl, 4-butyryloxyphenyl, 2,4-, 2,5-, 2,6-, 3,4- or 3,5-dichlorophenyl, 3,4-dimethoyphenyl, 3,4,5-trimethoxyphenyl, 3,4-methylenedioxyphenyl, 3-trifluoromethylphenyl, 4-methylthiophenyl, 4-methylsulfonylphenyl, 4-acetamidophenyl and so on.

The optionally substituted or unsubstituted 4-, 5- or 6-membered heterocyclic group R$_3$ may for example be 1-acetyl-2-azetidinyl, 1-methyl-2-pyrroryl, 3-methoxy-2-furyl, 3-methyl-2-furyl, 5-methyl-2-furyl, 5nitro-2-furyl, 3-methyl-2-thienyl, 3-bromo,4,5-dimethyl-2-thienyl, 2-methyl-4-thiazolyl, 1,2-dimethyl-4-chloro-5-imidazolyl, 1-butyl-4-pyrazolyl, 2,4-dichloro-4-isothiazolyl, 5-methyl-1,2,3-thiadiazolyl-4, 3,5-dimethyl-4-isoxazolyl, 2-methyl-5-diisopropylamino-4-oxazolyl, 5-methyl-1,2,5-oxadiazolyl-3, 4-methoxy-1,2,5-oxadiazolyl-3, 5-methyl-1,3,4-oxadiazolyl-2, 3-methyl-1,2,3-thiadiazolyl-5, 5-methyl-1,3,4-thiadiazolyl-2, 5-methyl-1,2,3-thiadiazolyl-4, 1-methyl-1,2,3-triazolyl-4, 2-ethyl-1,2,3,4-tetrazolyl-5, 5-nitro-2-pyridyl, 6-ethyl-2-pyridyl, 5-ethoxycarbonyl-3-pyridyl, 5-chloro-3-pyridyl, 1-butyryl-2-piperidyl, 2-oxo-5-pyranyl, 7-methoxy-3,4-dihydro-2H-2-pyranyl, 1-acetyl-2-pyrrolidinyl, 1-propyl-5-oxo-3-pyrrolidinyl, 3-methyl-2,4-dioxo-5-thiazolidinyl, 4-, 5-, 6- or 7-nitro-3-indolyl, 5-fluoro-2-indolyl, 2-methyl-5-methoxy-3-indolyl, 1-methyl-2-indolyl, 5-chloro-2-benzothienyl, 3-methyl-2-benzofuryl, 1-methyl-2-benzoimidazolyl, 6-nitro-2-benzothiazolyl, 4-chloro-3-quinolyl, 6-methoxy-2-quinolyl, 2,4-dimethoxy-3-quinolyl, 2-methyl-1-oxo-3-isocarbostyryl, 7-methyl-3-coumaryl, 4-methyl-2-quinzaolyl, 3-propyl-2,4-dioxo-5-imidazolinyl, 7-methoxycarbonyl-2-oxo-1,2-dihydro-3-quinazolyl, 2-furyl, 2-thienyl, 3-isoxazolyl, 4-imidazolyl, 1,2,5-thiadiazole-3-yl, 2-, 3- or 4-pyridyl, 2-pyrazinyl, 2-pyrimidinyl, 2-s-triazinyl, 1,2-dithiolanyl, 3-indolyl, 2-benzothienyl, 2-benzofuryl, 3-benzopirazolyl, 2-benzoimidazolyl, 2-benzoxazolyl, 3-benzoisoxazolyl, 3-benzoisothiazolyl, 2-benzothiazolyl, 2-benzo-1,4-oxazinyl, 3-quinolyl, 1-isoquinolyl and the like.

As examples of the substituted cycloalkylalkyl group R$_3$, there may be mentioned 3-acetyl-2,2-dimethyl-1-cyclobutylmethyl, 3-acetoxy-2,2-dimethyl-1-cyclobutylmethyl, 2-(3-chloro-1-cyclobutyl)ethyl, 2,3-dimethyl-1-cyclopentylmethyl, 2-isopropyl-1-cyclopentylmethyl, cis- or trans-4-acetamido-1-cyclohexylmethyl, cis-or trans-4-tert-butyl-1-cyclohexylmethyl, cis- or trans-2-(4-acetamido-1-cyclohexyl)ethyl and so on.

As examples of the substituted cycloalkenylalkyl group R$_3$, there may be mentioned 2-(4-isopropyl-1-cyclohexenyl)ethyl, 1-ethyl-2-(4-isopropyl-1-cyclohexenyl)-ethyl, 3-methoxy-4-methyl-3-cyclohexenylmethyl, and so on.

The substituted aralkyl group R$_3$ may for example be 4-bromobenzyl, 2-, 3- or 4-chlorobenzyl, 2,5- or 3,4-dimethoxybenzyl, 4-ethoxybenzyl, 4-fluorobenzyl, 3-or 4-methoxybenzyl, 4-methoxyphenylethyl, 1- or 2-naphthylmethyl, 2-, 3- or 4-nitrobenzyl, 3-nitrophenethyl, benzyl, 2-, 3- or 4-phenylpropyl, 1-, 2- or 3-methylbenzyl, 3,4,5-trimethoxybenzyl, α-methylphenethyl and so on.

As examples of the substituted heterocycle-alkyl group R$_3$, there may be mentioned 5-ethyl-3-indolylmethyl, 5-fluoro-3-indolylmethyl, 5-methoxy-3-indolylmethyl, 5-methyl-3-indolymethyl, 1-methyl-5-tetrazolylmethyl, 2-(1-piperidinyl)ethyl and so on.

When the acyl group R$_1$ and/or R$_2$ is a group of the formula:

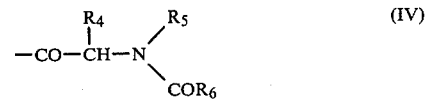

(wherein R$_4$, R$_5$ and R$_6$ are as respectively defined hereinbefore), the alkyl, cycloalkyl and aryl groups represented by R$_4$, R$_5$ and R$_6$ may for example be the corresponding groups mentioned for R$_3$. Thus as examples of the cycloalkylalkyl group represented by R$_5$, there may be mentioned the corresponding groups mentioned for R$_3$.

As examples of the alkenyl, cycloalkenyl and heterocyclic group R$_6$, there may be mentioned the corresponding groups mentioned for R$_3$.

As examples of the alkoxy group R$_6$, there may be mentioned alkoxy groups of 1 to 7 carbon atoms (e.g. methoxy, ethoxy, propoxy, isopropoxy, butoxy, isobutoxy, sec-butoxy, tert-butoxy, pentoxy, hexyloxy, heptyloxy, etc.), although alkoxy groups of 1 to 4 carbon atoms are preferred.

The cycloalkyl, aryl, indolyl or imidazolyl group $R_4$ may optionally be attached to the α-carbon atoms through an alkylene chain. Moreover, the cycloalkyl, cycloalkenyl, aryl or heterocyclic group $R_6$ may be optionally attached to the carbonyl carbon atom adjacent the nitrogen atom through an alkylene chain. As examples of such alkylene chains, there may be mentioned the alkylene chains given hereinbefore for $R_3$.

Therefore, when such an alkylene chain is interposed, $R_4$ represents cycloalkylalkyl, aralkyl, indolylalkyl, imidazolylalkyl, cycloalkenylalkyl or heterocycle-alkyl groups.

As examples of such cycloalkylalkyl, cycloalkenylalkyl, aralkyl and heterocycle-alkyl groups, there may be mentioned the corresponding groups given hereinbefore for $R_3$.

The indolylalkyl group may for example be 3-indolylmethyl, 2-(3-indolyl)ethyl, 3-(3-indolyl)propyl, 4-(3-indolyl)butyl, and the like. The imidazolyl group may for example be 4-imidazolylmethyl, 2-(4-imidazolyl)ethyl, 3-(4-imidazolyl)propyl, 4-(4-imidazolyl)butyl, and so on.

The groups represented by $R_4$ and $R_5$ as well as the alkyl, alkenyl, cycloalkyl, cycloalkenyl, aryl, heterocyclic, cycloalkylalkyl, cycloalkenylalkyl, aralkyl and heterocycle-alkyl groups represented by $R_6$ may optionally be substituted and such substituents may be similar to those mentioned as substituents on the groups represented by $R_3$.

As examples of such substituted groups $R_4$, $R_5$ and $R_6$, there may be mentioned the corresponding substituted groups $R_3$.

As examples of the substituted indolyl $R_4$, there may be mentioned 5-bromo-2-indolyl, 5-chloro-2-indolyl, 5-fluoro-2-indolyl, 5-methoxy-2-indolyl, 1-methyl-2-indolyl, 5-methyl-2-indolyl, and so on. The substituted imidazolyl $R_4$ may for example be 1-methyl-5-imidazolyl, 3-methyl-5-imidazolyl, 2-methyl-4-imidazolyl and the like.

As examples of the substituted indolylalkyl $R_4$, there may be mentioned 5-bromo-2-indolylmethyl, 5-bromo-2-indolylethyl, 5-chloro-2-indolylmethyl, 5-chloro-2-indolylethyl, 5-fluoro-2-indolylmethyl, 5-fluoro-2-indolylethyl, 5-methoxy-2-indolylmethyl, 5-methoxy-2-indolylethyl, 1-methyl-2-indolylmethyl, 1-methyl-2-indolylethyl, 5-methyl-2-indolylmethyl, 5-methyl-2-indolylethyl and so on.

As examples of the substituted imidazolylalkyl $R_4$, there may be mentioned 1-methyl-5-imidazolylmethyl, 1-methyl-5-imidazolylethyl, 3-methyl-5-imidazolylmethyl, 3-methyl-5-imidazolylethyl, 2-methyl-4-imidazolylmethyl, 2-methyl-4-imidazolylethyl, 1-methyl-4-imidazolylmethyl, 1-methyl-4-imidazolylethyl and so on.

As examples of the substituted benzyl $R_5$, there may be mentioned 4-bromobenzyl, 2-, 3- or 4-chlorobenzyl, 4-fluorobenzyl, 4-methoxybenzyl, 4-ethoxybenzyl, 2-, 3- or 4-methylbenzyl, 3,4-dimethoxybenzyl and so on.

As typical examples of the above-described N-acyl-α-aminoacyl group of the formula:

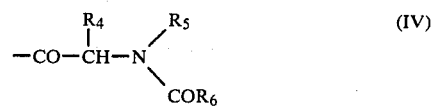

there may be mentioned N-acetyl-N-methyl-glycyl, N-benzoyl-N-methyl-glycyl, N-(4-chlorobenzoyl)-N-methylglycyl, N-acetyl-N-benzyl-alanyl, N-acetyl-N-methyl-leucyl, N-acetyl-N-methyl-phenylalanyl, 2-(N-acetyl-N-methyl)amino-3-methoxycarbonylpropionyl, 2-(N-acetyl-N-methyl)amino-3-methylmercaptopropionyl, 2-(N-acetyl-N-methyl)amino-3-ethylmercaptopropionyl, $N^\alpha$-acetyl-$N^\alpha$,N'-dimethylhistidinyl, N-acetyl-N-methylisoleucyl, N-acetyl-N-methylleucyl, N-acetyl-N-methyl-methionyl, N-acetyl-N-methylphenylalanyl, N-acetyl-N-methyl-triptophanyl, N-acetyl-N-methyl-4'-acetoxy-tyrosinyl, N-benzyl-N-methyl-valyl, N-acetyl-N-methyl-phenylglycyl, N-isonicotinoyl-N-methyl-α-aminobutyryl, (N-acetyl-N-methyl)amino-3-cyanopropionyl, N-acetyl-N-methyl-α-(2-thiazolyl)glycyl, N-acetyl-N-methyl-(4'-dimethylamino)-phenylalanyl and so on.

When the acyl group represented by $R_1$ and/or $R_2$ as above described is a group of the formula:

(wherein $R_7$ and $R_8$ are as respectively defined hereinbefore), the hydrocarbon residues $R_7$ and $R_8$ may for example be alkyl, alkenyl, cycloalkyl, cycloalkenyl, cycloalkylalkyl, cycloalkenylalkyl, aryl, aralkyl, phenylcycloalkyl, cycloalkylphenyl, biphenyl, and so on.

As examples of the alkyl, alkenyl, cycloalkyl, cycloalkenyl, cycloalkylalkyl, cycloalkenylalkyl, aryl and aralkyl groups represented by $R_7$ and $R_8$, there may be mentioned the corresponding groups already given for $R_3$.

As examples of the phenylcycloalkyl groups $R_7$ and $R_8$, there may be mentioned said cycloalkyl groups of 3 to 10 carbon atoms (particularly, 3 to 7 carbon atoms) substituted by a phenyl group, e.g. 2-phenylcyclopropyl and 4-phenylcyclohexyl, while as examples of the cycloalkylphenyl group, there may be mentioned a phenyl group substituted by said cycloalkyl group, e.g. 4-cyclopentylphenyl and 4-cyclohexylphenyl. The biphenyl may for example be 4-biphenyl.

As examples of the heterocyclic groups $R_7$ and $R_8$, there may be mentioned 4-, 5- or 6-membered heterocyclic groups containing N, O or/and S atoms, which may optionally be saturated or unsaturated, and optionally be fused to a benzene ring. As examples of such heterocyclic groups, there may be mentioned azetidinyl, pyrrolyl, furyl, thienyl, thiazolyl, isothiazolyl, oxazolyl, isoxazolyl, pyrazolyl, imidazolyl, pyridyl, pyrimidyl, pyrazinyl, triazinyl, quinolyl, quinazolyl, quinoxalyl, indolyl, benzofuranyl, benzothienyl, etc.

Optionally, $R_7$ and $R_8$ may, taken together, form a heterocyclic group in combination with the adjacent N atom, and, as examples of such heterocyclic group, there may be mentioned azetidinyl, pyrrolidinyl, piperazinyl, morpholinyl, and so on.

The hydrocarbon residues and heterocyclic groups, as represented by $R_7$ and $R_8$, as well as the heterocyclic group designated by

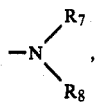

may optionally be substituted. As examples of such substituents thereon, there may be mentioned alkoxy groups of 1 to 4 carbon atoms (e.g. methoxy, ethoxy, propoxy, isopropoxy, butoxy, isobutoxy, sec-butoxy, etc.), $C_{1-4}$ alkylthio (e.g. methylthio, ethylthio, propylthio, isopropylthio, butylthio, etc.), phenoxy, phenylthio, cyclohexyloxy, halogens (e.g. fluorine, chlorine, bromine and iodine), cyano, $C_{2-5}$ alkoxycarbonyl (e.g. methoxycarbonyl, ethoxycarbonyl, propoxycarbonyl, isopropoxycarbonyl, butoxycarbonyl, isobutoxycarbonyl, sec-butoxycarbonyl, etc.), benzyloxycarbonyl, nitro, aminosulfonyl, dialkylamino (e.g. dimethylamino, diethylamino, diisopropylamino, dibutylamino, etc.) and so on. These substituents may be the same or different and may be present in the number of 1 to 3.

As to substituents on the groups, other than alkyl and alkenyl, which are among the hydrocarbon residues mentioned above, i.e. substituents on the hydrocarbon residues having cyclic moieties, and on heterocyclic groups, there may be mentioned, in addition to the abovementioned substituent groups, alkyl groups of 1 to 4 carbon atoms (which may be further substituted by said hydrocarbon residues $R_7$ and $R_8$), such as methyl, ethyl, propyl, isopropyl, butyl, trifluoromethyl, chloromethyl, 2-cyanoethyl, methoxymethyl, ethoxycarbonylmethyl and dimethylaminoethyl. As examples of substituents on the alkyls $R_7$ and $R_8$, there may be mentioned, in addition to the groups above-mentioned as substituents on said hydrocarbon residues, heterocyclic groups (which may be substituted) similar to the heterocyclic groups $R_7$ and $R_8$.

As specific examples of the substituted hydrocarbon residues $R_7$ and $R_8$, there may be mentioned 2-methoxyethyl, 3-methoxypropyl, β-methoxyisopropyl, 3-isopropoxypropyl, 3-sec-butoxypropyl, 3-cyclohexyloxypropyl, 3-phenoxypropyl, 2-chloroethyl, 3-chloropropyl, 4-chlorobutyl, 2-propylthioethyl 2-phenylthioethyl, 2-cyanoethyl, 5-cyanopentyl, 4-cyanocylohexylmethyl, methoxycarbonylmethyl, ethoxycarbonylmethyl, 1- or 2-methoxycarbonylethyl, 1-methoxycarbonylisobutyl, 5-methoxycarbonylpentyl, 5-dimethylaminopentyl, trifluoromethyl, 2-, 3- or 4-tolyl, xylyl, 2,4,5- or 2,4,6-trimethylphenyl, 2-, 3- or 4-chlorophenyl, 2,5-dichlorophenyl, 2-, 3- or 4-fluorophenyl, 4-bromophenyl, 4-iodophenyl, 2- or 3-trifluorophenyl, 2-, 3- or 4-nitrophenyl, 4-chloro-3-trifluoromethylphenyl, 2-methyl-4-nitrophenyl, 5-nitro-1-naphthyl,8-chloro-1-naphthyl, 4-methoxycarbonylphenyl, 4-ethoxycarbonylphenyl, 4-aminosulfonylphenyl, 2-, 3- or 4-methoxyphenyl, 4-ethoxyphenyl, 2,5-dimethoxyphenyl, 1-methoxycarbonyl-2-phenethyl, 1-methoxycarbonyl-1-phenylmethyl, 2-, 3- or 4-methylbenzyl, 2-, 3- or 4-chlorobenzyl, 2- or 3-fluorobenzyl, 3-iodo-benzyl, 2,4- or 3,4-dichlorobenzyl, 4-methoxybenzyl, α-methylbenzyl, 1,1-dimethylphenethyl, 4-methoxyphenethyl, 2-, 3- or 4-picolyl, 5-methyl-2-thienyl, 5-methyl-furfuryl, 3-piperazinopropyl, 2-morpholinoethyl, 4-methyl-1-piperazinylpropyl, 2-(1-methyl-2-pyrrolidinyl)ethyl, 2-thiazolylmethyl, 2-methyl-4-oxazolylmethyl, 5-chloro-1-methyl-3-indolylethyl and so on.

As specific examples of optionally substituted or unsubstituted heterocyclic groups $R_7$ and $R_8$, there may be mentioned 1-methyl-2-azetidinyl, 1-methyl-2-pyrrolyl, 5-methyl-2-furyl, 5-nitro-2-furyl, 3-methyl-2-thienyl, 4,5-dichloro-2-thienyl, 2-methyl-4-thiazolyl, 1,1-methyl-4-imidazolyl, 2-dimethyl-4-chloro-5-imidazolyl, 3,5-bismethylthio-4-isothiazolyl, 3-methyl-5-isoxazolyl, 2-methyl-4-oxazolyl, 1-methyl-3-pyrazolyl, 2-, 3- or 4-pyridyl, 4,5,6-trichloro-2-pyrimidinyl, 3,5,6-trichloro-2-pyrazinyl, 4,6-dichloro-2-s-triazinyl, 3- or 4-quinolyl, 2-quinazolyl, 2-quinoxalyl, 5-fluoro-1-methyl-3-indolyl, 2-benzofuryl, 2-benzothienyl and so on. When the heterocyclic group of

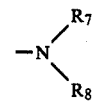

is substituted, the resultant group may for example be 2-, 3- or 4-methyl-1-piperidinyl, 4-methyl-1-piperazinyl, 2,6-dimethylmorpholino, 2-propyl-1-piperidinyl, etc.

As typical examples of

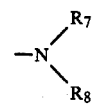

where $R_7$ and $R_8$ are other than hydrogen, there may be mentioned dimethylamino, diethylamino, dipropylamino, diisopropylamino, diisobutylamino, dibenzylamino, diphenethylamino, diphenylpropylamino, (N-methyl-N-benzyl)amino, (N-ethyl-N-butyl)amino, (N-methyl-N-cyclopentyl)amino, (N-methyl-N-cyclohexyl)amino or (N-methyl-N-furfuryl)amino.

When the acyl group represented by $R_1$ and $R_2$ as described above is a group of the formula:

$$-CO-O-R_9 \qquad (VI)$$

wherein $R_9$ is as defined hereinbefore), the hydrocarbon residue $R_9$ may for example hydrocarbon residues of 1 to 18 carbon atoms, such as alkyl, cycloalkyl, aryl, aralkyl group, etc.

As examples of the alkyl $R_9$, there may be mentioned alkyl groups of 1 to 18 carbon atoms (e.g. methyl, ethyl, propyl, isopropyl, butyl, isobutyl, sec-butyl, tertbutyl, pentyl, hexyl, heptyl, octyl, nonyl, decyl, undecyl, dodecyl, tetradecyl, hexadecyl, octadecyl, octadecyl, 1-ethylpropyl, neopentyl, 1-ethylpentyl, 1- or 2-ethylhexyl, etc.), although alkyl groups of 1 to 8 carbon atoms are among others preferred.

The cycloalkyl group $R_9$ as described above may for example cycloalkyl groups of 3 to 10 carbon atoms (e.g. cyclopropyl, cyclobutyl, cyclopentyl, cyclohexyl, cycloheptyl, cyclooctyl, adamantyl group, etc.).

As examples of the aryl group $R_9$ as described above, there may be mentioned phenyl, α- or β-naphthyl group.

As examples of the aralkyl group $R_9$ as described above, there may be mentioned the aryl groups given above, and, among others, an alkyl group of 1 to 4 carbon atoms substituted by a phenyl group, e.g. benzyl, phenethyl, 1- or 3-phenylpropyl, 1-phenylethyl, 1-methyl-3-phenylpropyl, 4-phenylbutyl, etc.

The hydrocarbon residue $R_9$ as described above may optionally be substituted, and as examples of such substituents there may be mentioned alkoxy groups of 1 to 4 carbon atoms (e.g. methoxy, ethoxy, propoxy, isopropoxy, butoxy, isobutoxy, sec-butoxy, etc.), phenoxy, benzyloxy, halogens (e.g. fluorine, chlorine, bromine and iodine), cyano group, and so on. Said substituents may be the same or different, and may be present in the number of 1 to 3.

As substituents on the groups other than alkyl groups, which are among the hydrocarbon residues $R_9$ mentioned above, i.e. substituents on the cyclic groups such as cycloalkyl, aryl and aralkyl groups, there may be mentioned, in addition to the above-mentioned substituent groups, alkyl groups of 1 to 4 carbon atoms (e.g. methyl, ethyl, propyl, isopropyl, butyl, etc.), halogenated alkyl groups of 1 to 4 carbon atoms (e.g. chloromethyl, bromomethyl, dichloromethyl, chlorodifluoromethyl, trifluoromethyl, etc.) and so on.

As specific examples of the substituted alkyl groups $R_9$, there may be mentioned 2-methoxyethyl, 2-ethoxyethyl, 2-butoxyethyl, 4-ethoxybutyl, chloromethyl, 1- or 2-chloroethyl, 2-bromoethyl, 2-fluoromethyl, 3-chloropropyl, 2,3-dichloropropyl, 2-chloroisopropyl, 1-chloromethyl-2-chloroethyl, 2,2,2-trichloroethyl, 2,2,2-trifluoroethyl, 1- or 2-cyanopropyl, and so on; examples of the substituted cycloalkyl group include 1-methylcyclobutyl, 1-methoxycyclopentyl, and 1-methylcyclohexyl; as examples of the substituted aralkyl group, there may be mentioned 2-, 3- or 4-chlorobenzyl, 4-bromobenzyl, 4-methoxybenzyl, 2,5- or 3,4-dimethoxybenzyl, 3-chloro-4-methylbenzyl and so on; and, as examples of the substituted aryl group, there may be mentioned 2-, 3- or 4-methylphenyl, 2-, 3- or 4-methoxyphenyl, 4-ethoxyphenyl, 2-, 3- or 4-chlorophenyl, 4-fluorophenyl, 2,4-dichlorophenyl, 2-, 3- or 4-chloromethylphenyl, 4-trifluoromethylphenyl, 4-bromophenyl or 3-dimethylaminophenyl.

The desired compound (I) can be produced by reacting the starting compound (II) with a carboxylic acid of the formula:

$$R_2\text{—OH} \quad \text{(VII)}$$

[wherein $R_2$ is as defined hereinbefore] or a reactive derivative with respect to carboxyl function of the same carboxylic acid.

As the means of the acylation may be mentioned a method of acylating the starting compound (II) with a carboxylic acid (VII) in the presence of carbodiimides.

The carboxylic acid (VII) may be used, for example, in a proportion of about 1 to 500 mole equivalents on the starting compound (II), and is preferably used in a proportion of about 1 to 30 mole equivalents on the same basis.

The carbodiimide may be used in a proportion of about 1 to 700 mole equivalents on the starting compound (II), and, in many cases, is preferably used in a proportion of about 1 to 50 mole equivalents on the same basis. The carbodiimide to be employed is any compound having a carbodiimide linkage (—N=C=N—) which may be transformed in a urea bond (—NH—CO—NH—) during the acylation reaction, and may for example be a compound of the formula:

$$R_{10}\text{—N}=\text{C}=\text{N—}R_{11} \quad \text{(VIII)}$$

[wherein $R_{10}$ and $R_{11}$ are organic residues which may transform the carbodiimide linkage into a urea bond during the acylation reaction].

As the organic residues $R_{10}$ and $R_{11}$, there may be mentioned $C_{3-7}$ cycloalkyl groups having or not having di-lower ($C_{1-6}$; the same applies hereinafter) alkylamino groups, lower alkyl groups having or not having di-lower alkylamino or morpholino groups, and phenyl having or not having lower alkyl groups. As the carbodiimides, there may be mentioned dicyclohexylcarbodiimide being practically preferable, and other examples include diphenylcarbodiimide, di-o-tolylcarbodiimide, di-p-tolylcarbodiimide, di-tert-butylcarbodiimide, 1-cyclohexyl-3-(2-morpholinoethyl)carbodiimide, 1-cyclohexyl-3-(4-diethylaminocyclohexyl)carbodiimide, 1-ethyl-3-(2-diethylaminopropyl)carbodiimide and 1-ethyl-3-(3-dimethylaminopropyl)carbodiimide.

The acylation reaction may be carried out in the presence of a suitable solvent. As examples of such solvent there may be mentioned esters (e.g. ethyl acetate), ethers (e.g. diethyl ether, dioxane, tetrahydrofurane, etc.), halogenated hydrocarbons (e.g. methylene chloride, chloroform, etc.), nitriles (e.g. acetonitrile), aromatic hydrocarbons (e.g. benzene), nitromethane, pyridine, dimethylformamide, dimethylsulfoxide, sulfolane and various suitable mixtures thereof.

The acylation reaction may be normally conducted at a suitable temperature from a temperature under ice-cooling to the reflux temperature of the reaction system.

The acylation reaction may be allowed to proceed more advantageously by employing a catalyst which can promote the acylation of the starting compound (II). Examples of such catalyst include a basic catalyst or an acid catalyst. As examples of the base catalyst there may be mentioned tertiary amines (e.g. aliphatic tertiary amines such as triethylamine, and aromatic tertiary amines such as pyridine, α-, β-, or γ-picoline, 2,6-lutidine, 4-dimethylaminopyridine, 4-(1-pyrrolidinyl)pyridine, dimethylaniline and diethylaniline], alkali metal halides (e.g. potassium fluoride, anhydrous lithium iodide, etc.), salts of organic acids (e.g. sodium acetate) and so on. As examples of the acid catalyst, there may be mentioned Lewis acids [e.g. anhydrous zinc chloride, anhydrous aluminium chloride ($AlCl_3$), anhydrous ferric chloride, titanium tetrachloride ($TiCl_4$), stannic tetrachloride ($SnCl_4$), antimony pentachloride, cobalt chloride, cupric chloride, boron trifluoride etherate, etc.], inorganic strong acids (e.g. sulfuric acid, perchloric acid, hydrogen chloride, hydrogen bromide, etc.), organic strong acids (e.g. benzenesulfonic acid, p-toluene-sulfonic acid, trifluoroacetic acid, trichloroacetic acid, etc.), acidic ion exchange resins (e.g. polystyrene sulfonic acid), and so on. When $R_2$ of the formula VII is a group shown by the formula —CO—$R_3$ [wherein $R_3$ is as defined hereinbefore], the reaction is generally conducted by preferably employing as the base catalyst 4-dimethylaminopyridine or 4-(1-pyrrolidinyl)pyridine or the like. When a carboxylic acid having, as $R_2$ in the formula (VII), an N-acyl-α-aminoacyl of the formula:

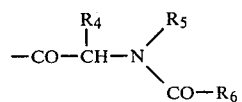

[wherein $R_4$, $R_5$ and $R_6$ are as defined hereinbefore], is employed, anhydrous zinc chloride is employed as a preferred catalyst.

The catalyst may be employed in the range of a catalytic amount which will be sufficient to prmote the acylation of the starting compound (II) with a carboxylic acid (VII), and, normally, in the range of about 0.001 to 10 mole equivalents, preferably in the range of about 0.01 to 1 mole equivalent based on the compound (VII). The use of such a catalyst often leads to marked increases in the yield of 20-acyloxymaytansinoid compound (I). It also helps save on the amount of carboxylic acid (VII), and thus, often reduces the requirement of (VII) down to about 1 to 10 mole equivalents based on the starting compound (II).

When isomers such as D-isomer and L-isomer exist in the carboxylic acid, e.g. one having an N-acyl-α-aminoacyl group $$(-CO-\underset{\underset{CO-R_6}{|}}{CH}-N\underset{CO-R_6}{\overset{R_5}{\diagup}}),$$

such isomers can be employed as the carboxylic acid (VII) in the acylation reaction, either solely or as a mixture of optional proportion.

When an optically active acyl group is introduced into the 20 position hydroxy group of the starting compound (II) through said reaction, it is sometimes desirable to utilize the corresponding optical isomer of the carboxylic acid (VII). Even when an optically active carboxylic acid (VII) is utilized, still, there sometimes results a 20-O-acyl-maytansinoid compound (I) as a mixture of D- and L-isomer in relation to the introduced acyl group.

As the means for acylation with the use of reactive derivative of the carboxylic acid (VII) may be mentioned a method of acylating with the use of a derivative having a functional group capable of acylating the 20-position or 20-position and 3-position hydroxyl groups of the starting compound (II), such as an acid anhydride and halide (e.g. chloride, bromide, etc.) of the carboxylic acid (VII). The solvent and catalyst employable in the means of acylation are exemplified by the same as those mentioned above in the acylation reaction in the presence of carbodiimides. The reaction temperature is normally about −40° to +100° C., and preferably about −20° to +40° C., although warming to higher temperatures may be effected to increase the rate of reaction.

The compound (I) of the present invention in which $R_2$ is designated by $$-CO-N\overset{R_7}{\underset{R_8}{\diagup}}$$

or $-CO-O-R_9$ [where $R_7$, $R_8$ and $R_9$ are as defined hereinbefore] can be produced by acylating the starting compound (II), for example, by carbamoylating or carbonating it.

The means for carbamoylation or carbonation may for example be a method of reacting the starting compound (II) in the presence of a base as a catalyst with a carbamic acid halide of the formula:

$$R_7\diagdown\!\!\!\diagup R_8\, NCOZ \qquad (IX)$$

or a halogeno-carbonate of the formula:

$$R_9O.CO.Z \qquad (X)$$

[wherein $R_7$, $R_8$ and $R_9$ are as defined hereinbefore; Z is halogen].

Referring to the above-mentioned formula (IX) or (X), halogen Z may for example be chlorine or bromine.

As examples of the base useful in the reaction, there may be mentioned tertiary amines similar to those given above, alkali metals (e.g. lithium, sodium, etc.), alkali metal hydrides (e.g. sodium hydride), or alkali metal alkyls or organic metal compounds of alkali metals [e.g. n-butyllithium, sec-butyllithium, tert-butyl lithium, phenyllithium, naphthalene sodium, sodium methylsulfinylmethide, dimsyl sodium ($CH_3SOCH_2Na$)]. Particularly desirable is pyridine or n-butyllithium.

The reaction is conducted in a solvent. The solvent may be any of solvents which do not inhibit the reaction; for example, when a tertiary amine such as pyridine is used as a catalyst, utilizable are ethers (e.g. tetrahydrofuran, dimethyl ether, diethyl ether, dioxane, etc.), esters (e.g. methyl acetate, ethyl acetate, butyl acetate, etc.), halogenated hydrocarbons (e.g. dichloromethane, chloroform, etc.), aromatic hydrocarbons (e.g. toluene, xylene, benzene, hexane, petroleum ether, etc.), or suitable mixture thereof, and pyridine, triethylamine, etc. may be used as the solvent, as well.

Further, n-butyllithium, alkali metals (e.g. sodium, lithium, etc.), and the like may be employed as a catalyst. In such a case, ethers (e.g. tetrahydrofuran, dimethyl ether, diethyl ether, etc.), aromatic hydrocarbons (e.g. toluene, xylene, etc.), and suitable mixtures of these solvents are used, although tetrahydrofuran is the most widely used.

In conducting the reaction, the starting compound (II) is dissolved in such a solvent and, after addition of said catalyst, a carbamic acid halide of the formula (IX) or halogeno-carbonate of the formula (X) is added. The catalyst is desirably employed in a proportion of about 3 to 20 mole equivalents and, for still better results, about 4 to 10 mole equivalents based on the starting compound (II). The carbamic acid halide or halogeno-carbonate is used in a proportion of about 3 to 20 mole equivalents and, preferably, about 5 to 10 mole equivalents on the same basis.

The reaction may be carried out at a suitable temperature within the range of about −80° to +50° C., although it is normally preferable to conduct the reaction at a temperature between about −30° and +40° C. The reaction solution, if necessary, is neutralized with dilute aqueous acid solution and, directly as it is or after removal of the solvent by distillation, can be subjected to conventional procedures known per se as will be described hereinafter to isolate the product.

The reaction may in some cases be conducted using other reactive derivative, with respect to the carboxyl function, of carbamic acid, in place of said carbamic acid halide.

An alternative carbamoylation procedure comprises reacting the starting compound (II) with a compound of the formula:

$$R_7-N=C=O \quad \text{(XI)}$$

[wherein $R_7$ is as defined hereinbefore].

This reaction procedure yields a 20-O-acylmaytansinoid compound in which a side chain with hydrogen of $R_8$ in the formula (V) is linked in the 20-position.

The reaction is preferably conducted in a state of solution. The solvent may be practically any solvent free from active hydrogen (e.g. the hydrogen atom of —OH or —NH—) which is reactive to the compound (XI). Thus, examples of the solvent are ethers (e.g. diethyl ether, dimethoxyethane, dioxane, tetrahydrofuran, etc.), halogenated hydrocarbons (e.g. dichloromethane, chloroform, carbon tetrachloride, 1,2-dichloroethane, etc.), aromatic hydrocarbons (e.g. benzene, toluene, xylene, chlorobenzene), nitriles (e.g. acetonitrile, propionitrile, etc.), esters (e.g. ethyl acetate) and suitable mixtures of these solvents. The reaction is desirably conducted in such a solvent as free from moisture as possible.

The amount of the compound (XI) necessary for the reaction may be nearly equimolar with the hydroxyl of the starting compound (II) to be acylated. However, it is still desirable to employ an excess of the compound (XI), for it may be partially consumed by the moisture contained in the solvent and, in some cases, by the dimerization or other reaction of the compound (XI) which per se is reactive. Thus, it is normally advisable to employ about 2 to 20 times the molar quantity and, preferably, about 2 to 5 times the molar quantity of the compound (II). The reaction may be conducted at about $-20°$ to $+80°$ C. and, preferably, at about $5°$ to $40°$ C. The reaction may be sometimes completed with reactive compound (XI) (normally, the compounds having nitro or polyhalogen substituents) by simply admixing both of the starting compounds with each other, but it is normally desirable to use a catalyst. As examples of the catalyst there may be mentioned the catalysts commonly employed in the carbamoylation of alcohols or phenols with isocyanic acid esters, such as bases [e.g. tertiary amines (e.g. triethylamine, pyridine, etc.), alkali metal alkoxides (e.g. potassium-tert-butylate, sodium methylate, etc.), alkali metal acetates (e.g. lithium-, sodium-, potassium-, rubidium-, or cecium acetate), metal salts (e.g. chlorides, organic carboxylates, etc. of lead, bismuth, tin, cobalt, zinc, cadmium, manganese, titanium, iron, copper, etc.), metal complexes or organo-metallic compounds (e.g. 2,4-pentadiene-metal complex, ferrocenes, dibutyltin oxide, dioctyltin oxide, dibutyltin bislaurate), etc.] and so on. Among these, anhydrous zinc chloride is used as the especially suited catalyst for the reaction from the standpoints of reaction selectivity, reaction rate, etc. The catalyst is used in a catalytic amount sufficient to accelerate the reaction, and generally, in the range of about 0.01 to 10 mole equivalents, preferably about 0.1 to 3 mole equivalents, against the compound (XI).

The 20-O-acylmaytansinoid compound (I) of the present invention produced by the above mentioned methods can be isolated and collected from the reaction mixture by conventional procedures, e.g. by appropriately applying such methods as concentration, solvent extraction, chromatography and recrystallization. When the compounds (I) are produced in the form of a mixture of isomers (e.g. D-isomer and L-isomer) in relation to the side-chain acyloxy group, these isomers can generally be separated from each other by separating means known per se, e.g. by silica gel column chromatography. The 20-O-acylmaytansinoid compound (I) of the present invention encompasses these individual isomers as well as mixtures thereof.

When the above mentioned acylation is applied to the starting compound (II) in which $R_1$ is H to produce the desired compound (I) in which $R_1$ is acyl group, use can be made of different forms of reactions depending on the desired compounds: for example, (a) the starting compound (II) in which $R_1$ is H is acylated to obtain the desired compound (I) in which $R_1$ and $R_2$ are the same acyl group, and (b) the compound (II) in which $R_1$ is H is acylated to firstly obtain the compound (XIII-I) of the formula:

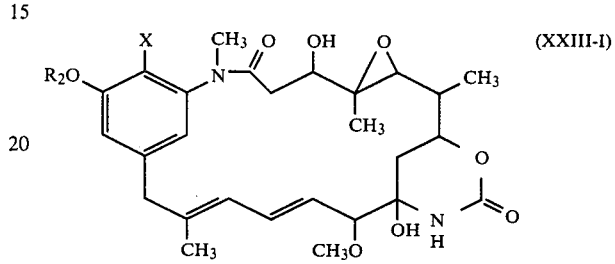

[wherein X and $R_2$ are as defined hereinbefore], and the resultant compound is subjected to the second-stage acylation to thus produce the desired compound (I).

In producing the compound (I) in which $R_1$ and $R_2$ are the same acyl group through the route (a), the above-mentioned acylation method is applied to the starting compound (II) in which $R_1$ is H (demethylmaytansinol, demethyldechloromaytansinol). In conducting the reaction, a catalyst capable of accelerating the reaction is employed. Examples of the catalyst which is useful include those as described in each of the above-mentioned acylation reactions; (i) in the case of acylation with the use of carboxylic acid of $R_3COOH$ and carbodiimide or carboxylic acid anhydride (in the latter case, further addition of carbodiimide may sometimes result in acceleration of the reaction, and the amount to be added may be the same as the one employed for activation of the carboxylic acid), preferably employed are a base catalyst such as tertiary amines [e.g. 4-dimethylaminopyridine, 4-(1-pyrrolidino)-pyridine, etc.] or an acid catalyst such as organic strong acids (e.g. trifluoroacetic acid), (ii) in the case of acylation with the use of amino acid derivative of

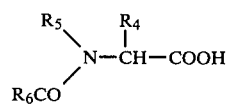

and carbodiimide, desirably used are Lewis acids (e.g. zinc chloride), tertiary amines [e.g. 4-dimethylaminopyridine, 4-(1-pyrrolidino)pyridine, etc.], or neutral salts (e.g. potassium fluoride, lithium iodide, etc.), (iii) in the case of acylation with the use of a carbamic acid halide of

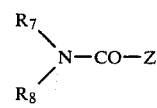

or a halogenocarbonate of R$_9$—O—CO—Z, the reaction is conducted in the presence of alkali metals (e.g. lithium, sodium, etc.), alkali metal hydrides (e.g. sodium hydride) or alkali metal alkyls (e.g. butyllithium, sec-butyllithium, phenyllithium, naphthalenesodium, sodium methylsulfinylmethide, etc.), phenylmagnesium bromide, (among these, butyllithium is preferred), etc. and (iv) in the case of acylation with R$_7$NCO—, preferably used are (heavy) metal salts such as zinc chloride and cuprous chloride, and tertiary amines such as pyridine and triethylamine. The reaction is desirably conducted in a solvent and, examples of such a solvent may be any of the solvents which do not hinder the reaction. In the reactions cited under (i), (ii) and (iv), useful are halogenated hydrocarbons (e.g. dichloromethane, chloroform, etc.), esters (e.g. methyl acetate, ethyl acetate, butyl acetate, etc.), ethers (e.g. diethyl ether, dioxane, tetrahydrofuran, etc.), nitriles (e.g. acetonitrile) and suitable mixtures of these solvents, although dichloromethane, chloroform, etc. are particularly preferable. In the reaction (iii), employed are said ethers or hydrocarbons (e.g. pentane, hexane, etc.), aromatic hydrocarbons (e.g. benzene, toluene, etc.) or mixtures of these solvents, although solvents containing tetrahydrofuran are in particular desirable. In the reaction (i), carboxylic acid may be used in a proportion of about 5 to 500 mole equivalents, and, preferably in many cases, about 10 to 50 mole equivalents, against the starting compound; carbodiimides may be used in a proportion of, for example, about 5 to 700 mole equivalents, and, preferably in many cases, about 5 to 70 mole equivalents, against the starting compound; and, carboxylic acid anhydride may be used in a proportion of, for example, about 5 to 500 mole equivalents, and, preferably in many cases, about 5 to 50 mole equivalents, against the starting compound. And, the reaction may be normally conducted at a suitable temperature ranging from a temperature under ice-cooling from a reflux temperature of the reaction system. In the reaction (ii), an amino acid derivative type carboxylic acid and carbodiimide are used in the same amounts as in the reaction (i); the catalyst in the reaction (ii) may be employed in a catalytic amount sufficiently to promote the acylation and, normally in a proportion of about 0.001 to 10 mole equivalents, preferably about 0.01 to 2 mole equivalents, against carboxylic acid; and, the reaction temperature can be selected out of the same temperature range as described for the reaction (i). In the acylation reaction (iii), a carbamic acid halide or halogeno-carbonate may be used in a proportion of about 5 to 50 mole equivalents, preferably about 5 to 20 mole equivalents, against the starting compound; a catalyst of the alkali metal, alkali metal hydride, alkali metal alkyl or phenylmagnesium bromide may be used in a proportion of about 5 to 50 mole equivalents, preferably about 5 to 20 mole equivalents; and, the reaction can be conducted at a suitable temperature selected out of the range of about −80° to +40° C., preferably about −40° to +25° C. In the reaction (iv), isocyanic acid ester may be used in a proportion of about 2 to 200 mole equivalents, preferably about 5 to 50 mole equivalents, against the starting compound; a catalyst of the (heavy) metal salt or tertiary amines may be used in a proportion of about 0.001 to 10 mole equivalent, preferably about 0.01 to 1 mole equivalent, against the isocyanic acid ester, whereby the tertiary amines may also be employed as the solvent; and, the reaction may be conducted at a suitable temperature within the range of a temperature under ice-cooling to a reflux temperature of the reaction system.

So as to acylate, through the route (b) mentioned above, the starting compound (II) in which R$_1$ is H to produce 20-acyl compound (I), relatively mild reaction conditions are employed. Namely, the required amount of a R$_3$COOH type carboxylic acid or corresponding carboxylic acid anhydride and (ii) an amino acid type carboxylic acid are in the range of about 1 to 30 mole equivalents, preferably about 3 to 10 mole equivalents, against the starting compound, while that of carbodiimide being in the range of about 1 to 50 mole equivalents, preferably about 3 to 15 mole equivalents. Although the catalyst is not necessarily required to be added to allow the reaction to proceed, it is normally advisable to add a tertiary amine (e.g. pyridine, 4-dimethylaminopyridine, triethylamine, etc.) of about 0.01 to 1 mole equivalent against the carboxylic acid, at the initiation of, or in the course of, the reaction, so as to make the rate of reaction faster and allow the reaction to go to completion. The reaction is conducted in a solvent as having been described in the procedure of (a), and is preferably carried out at a temperature under ice-cooling to the room temperature. (iii) when carbamoylation or carbonation of hydroxyl group of 20-position of the compound (XVII) corresponding to the starting compound (II) in which R$_1$ is H is conducted, the starting compound is reacted with a carbamic acid halide or halogenocarbonate in the presence of a base. Examples of the base include the bases employed in the carbamoylation or carbonation through the route (a) (the amount to be used is in the range of about 1 to 20 mole equivalents, preferably about 2 to 10 mole equivalents, to the starting compound), although tertiary amines (e.g. pyridine, 4-dimethylaminopyridine, etc.) are sometimes preferred. The amount of the tertiary amine is not particularly restricted, only if it is not less than the equimolar quantity of the carbamoylating or carbonating reagent, and may be, directly as it is, employed as a solvent for the reaction. Further examples of the reaction solvent include halogenomethanes (e.g. dichloromethane, chloroform, etc.), ethers (e.g. tetrahydrofuran, dioxane, diethyl ether, etc.), or mixtures of these solvents. The reaction can be conducted at a suitable temperature between about −80° and +40° C., preferably about −20° and +30° C. Acylation of the 3-position hydroxyl group of the 20-monoacyl derivative (XIII-1) obtained in this way is carried out through the same reaction as in the route (a) mentioned above.

In the latter step reaction of the route (a) or (b), there is formed in some cases, in combination with a bisacyloxy derivative of the desired compound (I), a 3,9,20-triacyloxy derivative (XIII-2) of the formula:

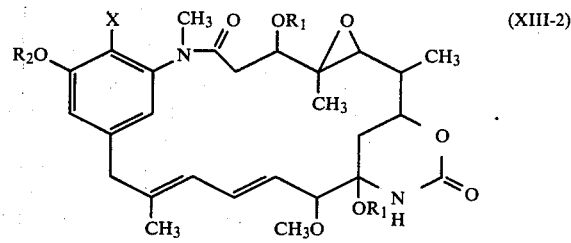

[wherein X is as defined hereinbefore; R$_1$ and R$_2$ are acyl group, respectively].

Triacyloxy derivative (XIII-2) is markedly formed, when the carboxylic acid or its reactive derivative to be employed for the acylation is lower alkane acids (e.g. acetic acid, propionic acid, butyric acid, isobutyric acid, valeric acid, isovaleric acid, etc) or their reactive derivatives. The triacyloxy derivative (XIII-2) can be obtained as the main product, when the reaction is conducted using the reagents (e.g. acylating reagent, catalyst, etc.) of two to three times the amounts of those employed in the synthesis of the bisacyl derivative, or when the additional amounts are added in the course of the reaction.

The compound (XIII-2), by treating it with an acid, can be easily converted into the compound (I) in which $R_1$ in the 9-position is hydrogen atom. Examples of the acids which are employable in said reaction include mineral acids (e.g. hydrogen chloride, hydrochloric acid, sulfuric acid, phosphoric acid, etc.), organic strong acids (e.g. benzene-sulfonic acid, toluene-sulfonic acid, methansulfonic acid, trifluoroacetic acid, trichloroacetic acid, etc.), and so on, and trifluoroacetic acid, among others, is preferred. The reaction is preferably conducted in the state of a solution, and usable as the solvent are the same solvents as used in the above-mentioned carbamoylation. Said reaction normally proceeds rapidly at a temperature of about $-20°$ to $+40°$ C. Also, the reaction can be, in some cases, conducted by merely passing a carbamoylation reaction solution containing the compound (XIII-2) through a silica gel column.

The desired product (I) can also be produced by (c) applying the above-mentioned acylation procedure to the starting compound (II) in which $R_1$ is H, or demethylmaytansinol or demethyldechloromaytansinol (XVII), to produce the desired compound of a bisacyloxy derivative (XIII-3), and yielding the compound (XIII-4) in which the 20-position acyloxy group is selectively converted into the hydroxyl group, followed by acylating it. In other words, the acyloxy group introduced in the 20-position can be regarded, in this case, as a temporary protective group for the 20-position. This may be understood by the facts; that the 20-position hydroxyl group is the phenolic hydroxyl group, in contrast to the 3-position hydroxyl group being the hydroxyl of secondary alcohol, whereby the esters derived from phenol, being chemically more active than esters derived from alcohols, are more susceptible to hydrolysis; and that in the maytansinoid compounds according to the present invention, the 3-position hydroxyl group is relatively blocked sterically by neighboring groups and situated in the position comparatively unsusceptible to acylation reaction, etc., whereas the 20-position hydroxyl group is situated in the position comparatively liable to the steric effect. And, it may follow in a sense that, since the 20-position acylated derivative (XIII-1) can be selectively produced from demethylmaytansinol or demethyldechloromaytansinol (XVII) as described above, more advantageous production of the compound (XIII-3) will be made possible by selecting an acyl group either being more susceptible to elimination during the reaction or possibly eliminated by a more selective elimination means as compared with the 3-position acyl group. As examples of the acyl groups being employed in such a case, there may be mentioned acyl type protective groups as being used as the protective groups for phenolic hydroxyl group in the conventional synthetic reactions (New Experimental Chemistry Course compiled by Chemical Society of Japan, Vol. 14, "Synthesis and Reactions of Organic Compounds [V]"; published by Maruzen, 1978). Examples of such protective groups, which are, among others, employed advantageously in the present invention, include (i) substituted acetyls, e.g. trifluoroacetyl (eliminating reagents: $KHCO_3$ or $K_2CO_3$-methanol), chloroacetyl (eliminating reagents: pyridine-ethanol, thiourea, 2-mercaptoethylamine, phenylenediamine, ethylenediamine-ethanol or silica gel), (ii) aromatic acyls, e.g. benzoyl (eliminating reagents: KOH-alcoholic aqueous solution), p-nitrobenzoyl (eliminating reagents: KOH-alcoholic aqueous solution), (iii) carbonate type acyls (example of eliminating reagents: benzyloxycarbonyl($H_2$-Pd/C)), tert-butoxycarbonyl (eliminating reagents: trifluoroacetic acid), etc., and so on.

So as to introduce these acyl type protective groups, the acylating agents (e.g. anhydride or halides corresponding to the acyl group) corresponding to these acyl groups can be used to conduct the same acylating method as the one of acylating the above-mentioned compound (II). A reaction for detaching these acyl-type protective groups is desirably conducted in a homogeneous solution except the case with insoluble reagents (e.g. silica gel, palladium carbon, etc.) and employable as the solvent are alcohols (e.g. methanol, ethanol, etc.), ethers (e.g. tetrahydrofuran, dioxane, etc.), ketones (e.g. acetone, methyl ethyl ketone, etc.), or suitable mixtures of these solvents, or these solvents containing water or mixed solutions thereof. The reaction can be conducted at a suitable temperature from a temperature under ice-cooling to a reflux temperature of the solvent. The eliminating reagents may be desirably used in a proportion of about 0.5 to 50 mole equivalents against the starting bis-acyloxy derivative. In view of the fact that the starting material of the bis-acyloxy derivative and the desired product of 3-acyloxy derivative (XIII-4) are both sensitive, in many cases, to the bases or acids employed here, it is in some cases advisable to add the required amounts of the detaching reagents little by little in several parts, accordingly. When a catalytic reduction with the use of palladium carbon is employed, it is desirably conducted in the same solvent as described above, under the stream of hydrogen of atmospheric or slightly elevated pressure, while using palladium of about 1 to 5% by weight based on the bisacyl derivative. The detaching reaction with the use of silica gel can be carried out by admixing with silica gel in a solvent chosen from esters (e.g. ethyl acetate), halogenated hydrocarbons (e.g. dichloromethane, chloroform, etc.) or mixtures thereof, in addition to the same solvents as being above described, at a suitable temperature of from the room temperature to a reflux temperature of the solvent, or by flowing down a solution of the bisacyloxy derivative as mentioned above through a column of silica gel.

As examples of the method of acylating the 20-position of the compound (XIII-4) there may be mentioned the same procedure as the above mentioned one for acylating the compound (II).

The desired compound (I) can be also produced by (d) further introducing the acyl group into the 3-position of demethylmaytansinol or demethyldechloromaytansinol (XVII) to produce the compound (XIII-5) in which the 3-position is acylated, followed by introducing the acyl group into the 20-position.

As an example of the reaction through the route (d), there may be mentioned the reaction which comprises carbamolying selectively the 3-position hydroxyl group of demethylmaytansinol or demethyldechloromaytansinol (XVII) with an isocyanic acid ester, and then acylating the 20-position in different ways. Selective carbamoylation of the 3-position hydroxyl group with an isocyanic acid ester is conducted in the presence of a catalyst. Examples of such catalyst include the same as cited for the carbamoylation reaction of the 20-position with an isocyanic acid ester, although anhydrous zinc chloride is among others preferred. The isocyanic acid ester may be used in a proportion of about 3 to 100 mole equivalents, preferably about 5 to 50 mole equivalents, against the starting material of demethylmaytansinol or demethyldechloromaytansinol, while the catalyst may be employed in a proportion of about 0.1 to 10 mole equivalents, preferably about 0.3 to 3 mole equivalents, against the isocyanic acid ester. The reaction is conducted in a solvent, and the preferred examples of the solvent include halogeno-methanes (e.g. dichloromethane, chloroform, etc.), ethers (e.g. tetrahydrofuran, dioxane, etc.), esters (e.g. ethyl acetate) and mixtures of these solvents. The reaction may be conducted at a suitable temperature of from a temperature under ice-cooling to a reflux temperature of the solvent. As examples of the method of acylating the compound (XIII-5), there may be mentioned the same method as the above-mentioned procedure of acylating the compound (II). Isolation and collection of the product (I) obtained in this way, along with separation of isomers therefrom, can be carried out in the same manner as those described above.

The compound (I) being obtained in this way can be used as an antifungal, antiprotozoal or antitumor agent. Its toxicity is low. The compound (I) can be also employed as an intermediate for the synthesis of useful medicines.

The biological activity of the compound (I) is shown below.

(A) Antimicrobial activity

With trypticase-soy-agar medium (Baltimor Biologicals Limited, U.S.A.) as the assay medium, the minimal inhibitory concentrations of the compound (I) is assayed against the microorganisms mentioned below employing the paper disc method. Thus, on the plates of those microorganisms, the antibacterial activity of 20-O-acylmaytansinoid compound (I) is assayed with paper discs (supplied by Toyo Seisakusho, Japan, thin-type, 8 mm diameter) immersed with 0.02 ml of a 300 µg/ml solution of 20-O-acylmaytansinoid compound (I). The results show that the compound (I) is inactive against the following microorganisms:

*Escherichia coli, Proteus vulgaris, Proteus mirabilis, Pseudomonas aeruginosa, Staphylococcus aureus, Bacillus subtilis, Bacillus cereus, Klebsiella pneumoniae, Serratia marcescens, Mycobacterium avium.*

On the other hand, the antifungal activity of the test compound is assayed against *Hamigera avellanea* IFO 7721 by the paper disc method, employing agar plates [each containing the medium consisting of 3.5 g of disodium phosphate 0.5 g monopotassium phosphate, 5 g yeast extract (Difco), 10 g glucose, 15 g agar, 1000 ml distilled water, and adjusted to pH 7.0]. Thus, on the plates inoculated with the above microorganism, the zones of growth inhibition are determined using paper discs (supplied by Toyo Seisakusho, Japan, thin-type, 8 mm diameter) immersed with 0.02 ml of a 100 µg/ml solution of 20-O-acylmaytansinoid compound (I).

The results shows that 20-O-acylmaytansinoid compound (I) inhibits growth of the said microorganisms.

The zones of growth inhibition by the compound (I) are shown in Table 1.

Then, with *Tetrahymena pyriformis* W strain used as the test microorganism and a medium composed of 20 g tryptose peptone (Difco), 1g yeast extract, 2 g glucose, 1000 ml distilled water and 10 ml of a 1 M phosphate buffer of pH 7.0 as the assay medium, the microorganism is incubated at 28° C. for 44 to 48 hours, and the growth inhibitory activity of said antibiotic compound is assayed by the serial dilution method. The results show that 20-O-acylmaytansinoid compound (I) inhibits the growth of the test organism.

Table 1 shows the growth inhibition activity of the compound (I) against the said microorganism.

TABLE 1

| Test Compounds | Antifungal activity, φmm *Hamigera avellanea* IFO 7721 | Antiprotozoal activity, MIC, µg/ml *Tetrahymena pyriformis* W |
|---|---|---|
| PDM-3 20-acetate | 31 | 2 |
| PDM-3 20-propionate | 34 | 2 |
| PDM-3 20-i-butyrate | 40 | 2 to 4 |
| PDM-3 20-butyrate | 40 | 2 to 4 |
| PDM-3 20-i-valerate | 44 | 2 |
| PDM-3 20-valerate | 44 | 2 to 4 |
| PDM-3 20-crotonate | 35 | 2 to 4 |
| PDM-3 20-benzoate | 35 | 2 to 4 |
| PDM-3 20-o-bromobenzoate | 27 | 1 to 2 |
| PDM-3 20-phenylacetate | 31 | 1 to 2 |
| PDM-3 20-cyclohexyl-carboxylate | 22 | 1 to 2 |
| PDM-3 20-picolinate | 21 | 2 |
| PDM-3 20-phenyl-carbamate | 16.5 | $\leq 1$ |

(B) Antitumor activity

In a therapeutic test in mice into which leukemia P-388 tumor cells have been intraperitoneally transplanted, 20-O-acylmaytansinoid compound (I) is administered intraperitoneally once daily for 9 consecutive days. The result shows that the compound (I) produces a definite prolongation of their life spans.

(C) Acute toxicity

The acute toxicity test in mice by the intravenous route shows that 20-O-acylmaytansinoid compound (I) produces no death at all at the dose level of 1000 µg/kg.

Because 20-O-acylmaytansinoid compound (I) has thus strong growth-inhibitory activity against fungi and protozoa, it is useful as an antifungal or antiprotozoal agent. Moreover, since 20-O-acylmaytansinoid compound (I) has a life-span extending activity in tumor-bearing, warm-blooded animals (e.g. mouse), it is expected to be of value as an antitumor agent.

As an antifungal or antiprotozoal agent, 20-O-acylmaytansinoid compound (I) can be used with advantage for testing bacterial flora in samples of soil, activated sludge and animal body fluids. Thus, when useful bacteria are to be isolated from soil samples or when the activity of bacteria other than protozoa or fungi is to be tested in the operation and analysis of an activated sludge system for the treatment of waste water, compound (I) can be utilized to ensure selective growth of bacterial flora without permitting the growth of fungi or protozoa concomitantly present in the samples. By way of example, a test sample is added to a liquid or solid medium, and 0.1 ml of a 10 to 100 μm/ml solution of 20-O-acylmaytansinoid compound (I) in 1% aqueous methanol is added per 1 ml of the medium, followed by effecting incubation.

The compound (I) according to the present invention shows the life-span extending activity in tumor-bearing warm-blooded animals (e.g. mouse, rat, dog, cat, etc.) and can therefore be used as an antitumor agent.

As an antitumor agent, the compound (I) according to the present invention can be administered parenterally or orally. In the case of parenteral administration, injections are preferred and, subcutaneous, intraperitoneal, intravenous and intramuscular injections, for example, are selectively employed. The dosage may range from about 12.5 to about 1000 μg per kg of body weight per dose, although it may be increased or decreased according to the condition, animal species and other factors. Such an injection may be prepared by the conventional procedures, for example by dissolving about 100 to 3000 μg of the compound (I) of the present invention in about 0.5 ml of alcohol (e.g. methanol, ethanol, etc.) and making it up with a sufficient amount of physiological saline to make a total of 10 ml. When the dosage is small, this solution may be further diluted with physiological saline.

The compounds (XIII-1 to -4) being produced in the acylation reaction of the present invention can be also used, for example, as the starting compound for production of the useful compound (I).

Compound (II) which is useful in the method of the present invention can, for example, be produced by bringing a maytansinoid compound (XIV) of the formula:

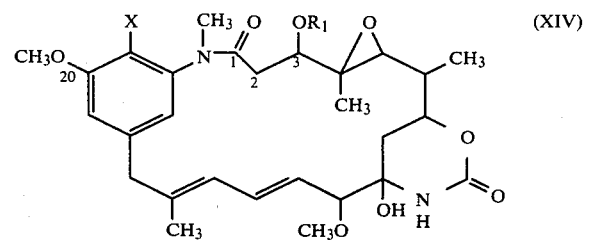
(XIV)

[wherein X and $R_1$ are as defined hereinbefore]into contact with a culture broth, or a processed matter of the culture broth, of a microorganism belonging to the genus Bacillus, the genus Streptomyces or the genus Actinomyces which is able to transform the 20-methoxy group of said maytansinoid compound into a hydroxyl group, and a starting compound (II) wherein $R_1$ is H can be produced by demethylating the 20-position of the above-mentioned compound (XIV) wherein $R_1$ is an acyl group through the above-mentioned conversion method with the use of microorganisms, followed by further subjecting to the reductive cleavage of the O-ester bond in 3-position with the use of a complex metal hydride compound.

The compound of the formula (XIV) wherein $R_1$=—CO—CH(CH$_3$)$_2$ and X=Cl is to be referred to as ansamitocin P-3, the compound (XIV) wherein $R_1$=—CO(CH$_2$)$_2$CH$_3$ and X=Cl will be referred to as ansamitocin P-3′, and the compound (XIV) wherein $R_1$=—COCH$_2$—CH(CH$_3$)$_2$ and X=Cl is to be referred to as ansamitocin P-4.

The above-mentioned compound (XIV) may be one of the known maytansines, ansamitocins and other compounds. The maytansine compounds are described for example in U.S. Pat. No. 3,896,111.

Maytanacine and maytansinol propionate can also be produced by the manner as described in Journal of the American Chemical Society 97, 5294 (1975) or by growing Nocardia sp. No. C-15003 (FERM-P No. 3992; IFO 13726; ATCC-31281) in a culture medium and isolating for collecting the metabolite from the culture broth [see Japanese Patent Publication Laid-open No. 121998/1978, Patent Application in the Federal Republic of Germany Laid-open as Offenlegungsschrift 2,746,253] [FERM: Fermentation Research Institute, Agency of Industrial Science and Technology, Japan; IFO: Institute for Fermentation, Osaka, Japan; ATCC: The American Type Culture Collection, U.S.A.].

Ansamitocin P-3, ansamitocin P-3′, and ansamitocin P-4 can be produced by cultivating the above-mentioned Nocardia sp. No. C-15003 [see Japanese Patent Application Laid-open No. 130693/1978, Patent Application in the Federal Republic of Germany Laid-open as Offenlegungsschrift 2,746,209].

The above-mentioned compound (XIV) can for example be produced by acylating maytansinol or dechloromaytansinol with a carboxylic acid of the formula $R_1$OH [wherein $R_1$ is as previously defined] or a reactive derivative with respect to carboxyl function of said carboxylic acid.

The compound (XIV) can be obtained by reacting maytansinol or dechloromaytansinol either with a carbamic acid halide of the formula:

(IX)

[wherein $R_7$ and $R_8$ are as defined hereinbefore; Z is halogen] in the presence of a base (carbamoylation reaction) or with a compound of the formula $R_7$—N=C=O in the presence of a catalyst (carbonation reaction). The compound (XIV) can also be produced by reacting maytansinol or dechloromaytansinol with a halogenocarbonate of the formula:

[wherein $R_9$ and Z are as defined hereinbefore] in the presence of a base.

The above acylation (inclusive of the carbamoylation or carbonation) can be conducted by the same procedure as in the acylation described hereinbefore.

Maytansinol, which is used for the production of the above compound (XIV), is a compound known as a plant principle [Kupchan et al, J. Amer. Chem. Soc., 97, 5294 (1975)], which can also be obtained by the reductive cleavage of a maytansine compounds.

Moreover, maytansinol can also be produced by the steps of growing Nocardia sp. No. C-15003 (FERM-P No. 3992, IFO-13726, ATCC-31281) in a culture medium to obtain maytanacine, maytansinol propionate or ansamitocins of the formula:

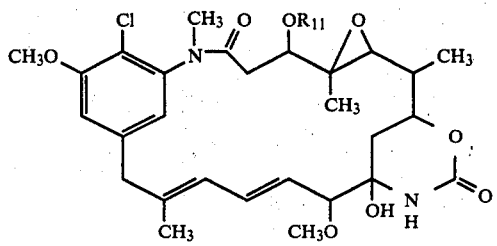

(XV)

[wherein $R_{11}$ is acetyl, propionyl, iso-butyryl, n-butyryl or iso-valeryl] and subjecting the same metabolite to a reductive cleavage reaction with the use of a metal hydride compound, e.g. LiAlH$_4$ [see Nature, vol. 270, 721 (1977), Japanese Patent Application Laid-open No. 130693/1978, Patent Application in the Federal Republic of Germany Laid-open as Offenlegungsschrift 2,746,209].

Dechloromaytansinol can be produced by the reduction with a metal hydride compound of a compound (XIV) in which X is Cl. The metal hydride compound is preferably a metal complex such as lithium aluminium hydride (LiAlH$_4$), and is used normally in the amount of about 1 to 25 moles, preferably of about 4 to 10 moles, per mole of the starting compound (XIV) (X=Cl). Normally, this reduction is preferably conducted in a solvent, which may for example be an ether (e.g. diethyl ether, tetrahydrofuran, etc.) and, preferably, tetrahydrofuran. This reaction can be carried out normally at a temperature of about −70° C. to +80° C., and preferably about −40° C. to +20° C. In many cases, this reaction gives rise to a compound corresponding to the compound (XIV) (X=Cl) in which the 3-acyl group alone has been eliminated, that is to say, maytansinol, as a by-product. After the reduction reaction, the excess reducing agent is destroyed by adding water, acetic acid or ethyl acetate, etc., and the reaction mixture, after being made acidic, is extracted with a suitable solvent (e.g. ethyl acetate). The resulting crude product is isolated and purified, for example, by silica gel chromatography or high-pressure liquid chromatography, whereby the desired dechloromaytansinol is obtained.

The microorganisms employable in the above-mentioned procedure of transforming the 20-methoxy of said compound into a hydroxyl group may be any microorganism of the genus Bacillus, the genus Streptomyces or the genus Actinomyces, inclusive of any mutants thereof, so long as is can transform the 20-methoxy group of the maytansinoid compound (XIV) into a hydroxy group. As examples of such organisms which can be used in the said procedure, there may be mentioned *Bacillus megaterium* IFO 12108 (NRRL B-349), *Streptomyces flavotricini* IFO 12770 (ATCC 23621 & 19757), *Streptomyes platensis* IFO 12901 (ATCC 23948), *Streptomyces libani* IFO 13452 (ATCC 23732) and *Actinomyces nigrescens* IFO 12894 (ATCC 23941). [NRRL: Northern Utilization Research and Development Division, U.S. Department of Agriculture, U.S.A.].

The microorganisms assigned the above-mentioned IFO numbers are found on the List of Cultures, 1978 (sixth edition), published by the Institute for Fermentation, Osaka, Japan. The microorganisms appearing on the List can be obtained from the said Institute for Fermentation, Osaka.

Generally speaking, microorganisms of the genera Bacillus, Streptomyces and Actinomyces are liable to vary in character, and can be made to undergo mutation, for example, by such artificial mutagenic treatments as irradiation with X-rays, ultraviolet ray or other radiation, or by means of an artificial mutagen (e.g. nitrosoguanidine, ethyleneimine, etc.). All such mutants can be employed in the practice of the present invention insofar as they are able to transform the 20-methoxy group of maytansinoid compound (XIV) into a hydroxyl group.

The culture medium which is used in the cultivation of the above-mentioned microorganisms may be any liquid or solid medium containing the nutrients which the particular microorganisms are able to utilize, although a liquid medium is preferable for large scale operations. The culture medium is prepared using the carbon sources which will be assimilated by the microorganism and the nitrogen sources, inorganic materials, trace nutrients, etc. which will be digested by the microorganism. Thus, as such carbon sources, there may be employable glucose, lactose, sucrose, maltose, dextrin, starch, glycerin, mannitol, sorbitol, fats and oils (e.g. soybean oil, lard oil, chicken oil, etc.) and so on, while the nitrogen sources may for example be meat extract, dried yeast, soybean meal, corn steep liquor, peptone, cottonseed meal, spent molasses, urea, ammonium salts (e.g. ammonium sulfate, ammonium chloride, ammonium nitrate, ammonium acetate, etc.), and so on. The medium may further contain appropriate amounts of salts containing sodium, potassium, calcium, magnesium, etc., metal salts such as salts of iron, manganese, zinc, cobalt, nickel, etc., salts of phosphoric acid, boric acid, etc., and salts of organic acids such as acetic acid, propionic acid, etc. The medium may also contain other components such as amino acids (e.g. glutamic acid, aspartic acid, alanine, glycine, lysine, methionine, proline, etc.), peptides (e.g. dipeptides, tripeptides, etc.), vitamins (e.g. B$_1$, B$_2$, nicotinic acid, B$_{12}$, C, E, etc.), nucleic acids (e.g. purine, pyrimidine and their derivatives, etc.) and so on. It is, of course, possible to add inorganic or organic acids, alkalis, buffers, etc. for the purpose of adjusting the pH of the medium, or to add suitable amounts of fats and oils, surfactants, etc. for defoaming purposes.

The cultivation may be carried out by any procedure such as stationary, shake or aerobic stirred culture. Of course, submerged aerobic culture is preferred for large scale operations. While the cultural conditions depend on the condition and composition of the medium, the microorganisms, the culture procedure and so on, it is normally desirable that the cultivation be carried out at a temperature of 20° to 45° C. and at an initial pH of substantial neutrality. The temperature in the intermediate stage of cultivation is desirably between 24° C. and 37° C., and the initial pH of the medium is desirably between 6.5 and 8.5. While the cultivation is completed in about 6 to 100 hours, the incubation period of 16 to 60 hours is particularly satisfactory.

The term "culture broth" as used herein means the product obtained in the cultivation process described above.

The term "processed matter of the culture broth" as used herein means the cells or disrupted cells containing a demethylation enzyme system which are obtainable by subjecting the above-mentioned culture broth to any of such physical or chemical treatments as filtration, centrifugation, ultrasonic disruption, treating with a French press, alumina grinding or treatment with a bacteriolytic enzyme, surfactant or an organic solvent.

The demethylation enzyme system purified by the conventional procedure, and the bacterial cells or demethylation enzyme system immobilized by the conventional procedure may also be successfully utilized.

The method with the use of said microorganisms comprises bringing the compound (XIV) into contact with the above-mentioned culture broth or processed matter of the said culture broth. The concentration of the starting compound in the reaction solution is suitably within the range of 1 to 200 μg/ml. The preferred reaction temperature is 20° to 50° C. and the preferred pH is 5 to 10, although the temperatures from 24° to 40° C. and pH levels from 6 to 9 are especially desirable. The reaction time may range from 10 minutes to 100 hours and, preferably, 1 to 48 hours. While the reaction may be carried out under stationary, shake, aerobic submerged or stirred conditions, it is more advantageous to conduct the reaction under shake, aerated or stirred culture conditions. If desired, a reaction stimulator, an enzyme stabilizer and other agents may be added to the reaction system. As examples of said reaction stimulator, there may be mentioned coenzymes such as nicotinamide-adenine dinucleotide (NAD), nicotinamide-adenine dinucleotide phosphate, (NADP), flavine mononucleotide (FMN) and flavine-adenine dinucleotide (FAD), etc., their precursors (e.g. adenine, adenosine, adenylic acid, nicotinamide, flavine, riboflavine, etc.), metal salts (e.g. magnesium chloride, manganese chloride, ferrous chloride, ferric chloride, zinc chloride, etc.), surfactants [e.g. Triton X-100 (Rohm and Haas Co., U.S.A.), Brij-58 (Kao-Atlas Co., Japan), etc.], 3′,5′-cyclic adenylic acid and so on. The enzyme stabilizer may for example be cysteine, 2-mercaptoethanol, dithiothreitol, sucrose or glycerin.

The compound (II) thus produced can be detected by thin-layer chromatography (hereinafter referred to briefly as TLC). The reaction mixture is extracted with ethyl acetate, and the extract is concentrated to one-hundredth of its initial volume to be subjected to TLC using a silica-gel glass plate (Kieselgel 60F$_{254}$, 0.25 mm, 20×20 cm) (hereinafter "Kieselgel" means the product of E. Merck A.G., West Germany) and a 9:1 solvent mixture of chloroform and methanol. The chromatogram is irradiated with ultraviolet ray at 2537 A to detect the desired compound.

The compound (II) can be isolated from the reaction mixture by utilizing the purification procedures normally used for the recovery of microbial metabolites, by taking advantage of the weakly acidic and lipophilic property of compounds of this class. By way of example, the procedure utilizing the difference in solubility between the compound (II) and impurities, the procedure which takes advantage of the differential adsorptive affinity of various adsorbents such as activated charcoal, macroporous nonionic resins, silica gel, alumina, etc., for the compound (II) versus impurities and the procedure of removing impurities by means of ion exchange resins may be employed alone, in combination or in repetition. When resorted to the procedure relying on the solubility difference, use is made of a suitable solvent for extraction from the filtrate such as water-immiscible organic solvents, e.g. fatty acid esters (e.g. ethyl acetate, amyl acetate, etc.), alcohols (e.g. butanol), halogenated hydrocarbons (e.g. chloroform), ketones (e.g. methyl isobutyl ketone), and so on. The extraction is carried out in the weakly acidic region; preferably, the compound (II) is extracted with ethyl acetate from the culture broth filtrate preadjusted at pH 6. The extract thus obtained is washed with water and concentrated under reduced pressure, followed by adding a non-polar solvent such as petroleum ether and hexane to recover a crude product (i) containing the active component. Since the TLC of this crude product gives many spots other than that of the novel demethylmaytansinoid compound (II), the following stepwise purification procedure is carried out. Thus, normally various adsorption chromatographic techniques are useful for this purpose and, as the adsorbents, the common supports such as silica gel, alumina and macroporous nonionic adsorbent resins can be utilized. However, for the purification of the crude product (i), silica gel is the most advantageous of all the absorbents. Development is started with a non-polar solvent such as petroleum ether and hexane, followed by elution of the demethylmaytansinoid compound (II) with an added polar solvent such as ethyl acetate, acetone, ethanol and methanol. By way of example, column chromatography is carried out using silica gel (hereinafter silica gel mean the product of E. Merck AG., West Germany, 0.05 to 0.2 mm) as the carrier and with incremental ratios of ethyl acetate to hexane. The eluate is assayed by TLC and the fractions containing demethylmaytansinoid compound (II) are pooled, concentrated under reduced pressure, and treated with petroleum ether or hexane to recover a crude product (ii). Because this crude product still contains impurities, it is further purified as follows. Thus, for example, the second purification process is carried out on a second silica gel column using a different solvent system. The development is started with a halogenated hydrocarbon such as dichloromethane and chloroform, followed by eluating with a polar solvent such as an alcohol (e.g. ethanol, methanol, etc.) and a ketone (e.g. acetone, methyl ethyl ketone, etc.) to recover the novel demethylmaytansinoid compound (II). The solvent systems for the first and the second silica gel column may be reversed in order, and it is possible to employ other suitable combinations of organic solvents which are normally employed.

When a macroporous adsorbent resin is employed for the purification of the crude product (ii), the novel demethylmaytansinoid compound (II) may be separated by elution with a mixture of a lower alcohol, a lower ketone or an ester with water. As examples of the lower alcohols, there may be mentioned methanol, ethanol, propanol, butanol, and others. The lower ketone may for example be acetone or methyl ethyl ketone, while examples of the ester include ethyl acetate. Thus, by way of illustration, the crude product (ii) is dissolved in 50 v/v % aqueous methanol and adsorbed on a column of Diaion HP-10 (Mitsubishi Chemical Industries, Ltd., Japan). The column is washed with 50 v/v % aqueous methanol, followed by elution with 90 v/v % aqueous methanol to obtain the desired demethylmaytansinoid compound (II).

The demethylmaytansinoid compound (II) thus obtained is concentrated under reduced pressure and crystallized from ethyl acetate. Alternatively, after the concentration, petroleum ether is added to the concentrate and the resulting powders are recovered.

Furthermore, by deacylating the compound (XVI) which is the demethylmaytansinoid compound (II) in which $R_1$ is an acyl group, there can be obtained the demethylmaytansinoid compound (XVII) (namely, demethylmaytansinol) which is the compound (II) in which $R_1$ is H. Since the acyl group is present in the β-position of the carbonyl group, the conventional reductive cleavage reaction procedure can be utilized with advantage. Thus, the compound (XVII) can be obtained by the reductive cleavage of the O-ester bond in the 3-position with the use of a complex metal hydride compound [e.g. lithium aluminium hydride (LiAlH$_4$)] at a low temperature (e.g. −20° to 0° C.), the reaction being thus accomplished without affecting other functional groups such as carbonyl, epoxy, carbon-carbon double bond, etc. The compound (XVII) can be isolated and purified in the same manner as the above-mentioned procedure for the compound (II).

When the demethylmaytansinoid compound (II) described in detail in the above contains stereoisomerism in acyl group R$_1$ (e.g. D- and L-isomer), the compound (II) encompasses such isomers and a mixture thereof. Generally, such as isomeric configuration may already be present in the starting compound (XIV) and, there are cases in which these isomers have been separated into respective components during the process of production of the compound (XIV) by the per se conventional separation procedure such as silica gel chromatography and high speed liquid chromatography.

Generally, the isomeric relation in the compound (II) is in many cases identical with that in the compound (XIV).

Moreover, when a mixture of these isomers is employed as the starting compound (XIV), the product compound (II) is obtained as a mixture of isomers. These isomers can be separated from each other generally by a procedure per se known, e.g. by silica gel chromatography.

The Reference Examples and Examples are to be below described to illustrate the present invention more specifically but should not be considered to be limitative of the scope of the invention. Unless otherwise indicated, all percents (%) are by weight/volume (w/v %).

REFERENCE EXAMPLE 1

In 5 ml of dry dichloromethane is dissolved 99.6 mg (0.176 mmole) of maytansinol, followed by adding 377.2 mg (1.76 mmoles) of hexanoic anhydride (caproic anhydride) and 43.5 mg (0.366 mmole) of p-dimethylaminopyridine (DMAP). After the mixture is stirred at the room temperature (ca. 23° C.) for 6 hours, 30.5 mg (0.25 mmole) of DMAP is further added, followed by stirring the mixture at the room temperature for additional 18 hours. To the reaction mixture are added 5 ml of 1 N-HCl and 5 ml of water, and the organic layer is taken by separation, washed with 10% aqueous sodium hydrogen carbonate (10 ml) and dried over anhydrous sodium sulfate. The solvent is distilled off and the residue is chromatographed on a column of silica gel (75 g), elution being carried out with ethyl acetate (ca. 250 ml) and, then, with ethyl acetate/ethyl acetate saturated with water (2:1 v/v) (ca. 900 ml). The eluate is collected in 16 g fractions, and fractions No. 13 through 30 are pooled and concentrated to remove the solvent, whereby 3.0 mg of the crude product is obtained. The crude product is dissolved in ethyl acetate and, after addition of ether, a white powdery solid is recovered by filtration, resulting in 34.3 mg of maytansinol 3-hexanoate m.p. 159°–162° C. (decomp.).

REFERENCE EXAMPLE 2

In 1.0 ml of dichloromethane is dissolved 23.5 mg of maytansinol, and at about 22° C., 70.5 mg (ca. 10 mmole equivalent) of acetic-formic anhydride (prepared by cooling 2 ml of acetic anhydride at −5° to 0° C., adding 1 ml of 99% formic acid under stirring over a period of about 10 minutes at −5° to 0° C., heating the mixture at 50° C. for 15 minutes and quenching it to 0° C.) and 11.7 mg of 4-dimethylaminopyridine are added, followed by stirring at room temperature overnight. To the reaction mixture is added 10 drops of methanol, and after stirring for 3 hours at the room temperature, the mixture is concentrated to dryness under reduced pressure. The residue is spotted on a silica gel preparative thin layer chromatoplate and developed twice with ethyl acetate saturated with water. The silica gel in the zone 6.0 to 8.0 cm above the base line is scraped off, and extracted with 10% methanoldichloromethane. The solvent is distilled off under reduced pressure to recover 8.35 mg of maytansinol 3-formate as a colorless glassy substance.

REFERENCE EXAMPLE 3

By a similar procedure to that described in Reference Example 1 or 2, the following compounds can be prepared.

(A) From maytansinol and octanoic anhydride (caprylic anhydride), there is obtained maytansinol 3-octanoate as a white sandy solid melting at 151°–160° C. (decomp.)

(B) From maytansinol and decanoic acid (capric acid), there is obtained maytansinol 3-decanoate as a white sandy solid melting at 130°–134° C. (decomp.).

(C) From maytansinol and heptanoic acid, there is obtained maytansinol 3-heptanoate, m.p. 158°–160° C. (decomp.).

(D) From maytansinol and tridecanoic acid, there is obtained maytansinol 3-tridecanoate, m.p. 110°–116° C. (decomp.).

(E) From maytansinol and hexadecanoic acid (palmitic acid), there is obtained maytansinol 3-hexadecanoate as a white powder melting at 105°–116° C. (decomp.).

(F) From maytansinol and valeric anhydride, there is obtained maytansinol 3-valerate, m.p. 165°–168° C.

REFERENCE EXAMPLE 4

To a mixed solution of maytansinol (103.2 mg, 0.183 mmoles) and cyclohexanecarboxylic acid (140 mg, 1.094 mmoles) in 5 ml of dry dichloromethane is added dicyclohexylcarbodiimide (DCC) (267 mg, 1.296 mmoles), and after stirring at a room temperature for a short while until insolubles begin to separate out, p-dimethylaminopyridine (DMAP) (50.8 mg, 0.416 mmoles) is added. The mixture is stirred at a room temperature overnight. Then, the insolubles are filtered off, and the filtrate is washed with 0.5 N-HCl (ca. 10 ml) and with saturated aqueous sodium hydrogen carbonate (ca. 10 ml) in that order and is dried over anhydrous sodium sulfate. The solvent is distilled off, and the residue is chromatographed on a column of silica gel (75 g), followed by eluting with ethyl acetate and collecting the eluate in 16 g fractions. The fractions No. 14 through No. 30 are pooled and concentrated to remove the solvent, resulting in 59 mg of the crude product. The crude product is dissolved in ethyl acetate, followed by adding ether. There is obtained 24.3 mg of maytansinol 3-cyclohexanecarboxylate as crystals melting at 202°–206° C. (decomp.).

REFERENCE EXAMPLE 5

The following compounds can be produced by the procedure similar to that described in Reference Example 4.

(A) From maytansinol and cyclopropanecarboxylic acid, there is obtained maytansinol 3-cyclopropanecarboxylate, m.p. 182°–187° C. (decomp.).

(B) From maytansinol and phenylacetic acid, there is obtained maytansinol 3-phenylacetate, m.p. 180°–182° C. (decomp.).

(C) From maytansinol and benzoic acid, there is obtained maytansinol 3-benzoate, m.p. 174°–177° C. (decomp.).

(D) From maytansinol and p-chlorobenzoic acid, there is obtained maytansinol 3-p-chlorobenzoate, m.p. 178°–183° C. (decomp.).

(E) From maytansinol and 2-furancarboxylic acid, there is obtained maytansinol 3-(2-furan)carboxylate, m.p. 180°–189° C. (decomp.).

(F) From maytansinol and phenylpropionic acid, there is obtained maytansinol 3-phenylpropionate, m.p. 160°–163° C. (decomp.).

(G) From maytansinol and nicotinic acid, there is obtained maytansinol 3-nicotinate as a white powder melting at 184°–187° C. (decomp.).

(H) From maytansinol and picolinic acid, there is obtained maytansinol 3-picolinate, m.p. 190°–193° C. (decomp.).

(I) From maytansinol and isonicotinic acid, there is obtained maytansinol 3-isonicotinate as white crystals melting at 185°–187° C. (decomp.).

(J) From maytansinol and N-acetyl-L-proline, there is obtained maytansinol 3-(N-acetyl)prolinate, both as white crystals melting at 195°–198° C. (decomp.) and as a glassy product with a UV spectrum ($\lambda_{max}^{MeOH}$) nm: 233, 244, 253, 282, and 292.

(K) From maytansinol and 2-thiophenecarboxylic acid, there is obtained maytansinol 3-(2-thiophene)carboxylate as a glassy solid melting at 161°–163° C. (decomp.).

REFERENCE EXAMPLE 6

In 800 ml of dry THF is dissolved 15.0 g of antibiotic ansamitocin mixture (ansamitocin P-2=12%; ansamitocin P-3=71%; ansamitocin P-4=17%) and, in dry region gas stream, the solution is chilled to −50° C. by the use of a dry-ice-ethanol bath. Then, 13.0 g of lithium aluminium hydride (LiAlH$_4$) is added at one time, and the mixture is stirred at −50° C. to −22° C. for 2 hours. The mixture is cooled to −28° C., to which is added an additional 3 g of LiAlH$_4$, and stirred at −28° C. to −22° C. for 80 minutes, followed by cooling again down to −50° C. to add dropwise 750 ml of 2 N-HCl carefully over a period of 30 minutes. The reaction mixture is extracted three times with 2.6 l, 1.6 l and 0.8 l portions of ethyl acetate, and the extracts are combined, washed with saturated aqueous sodium chloride (100 ml×2) dried (250 g MgSO$_4$). The solvent is distilled off under reduced pressure, and the residue (13.6 g) is chromatographed on a column of silica gel (1.2 kg), elution being carried out with ethyl acetate/water (=98.5:1.5, v/v). The eluate is collected in 400 g fractions, and the fractions No. 35 through No. 52 are pooled. The solvent is distilled off and the residue is dried in vacuo to recover 7.25 g of maytansinol. Then, by the same procedure, there is obtained 1.55 g of an approximately equimolar mixture of maytansinol and dechloromaytansinol from the fractions No. 53 through No. 68. Similarly, 0.87 g of dechloromaytansinol is recovered from the fractions No. 69 through No. 86. Reprecipitation from chloroform-hexane yields 0.71 g of dechloromaytansinol as a white powder, m.p. 174°–179° C. (decomp.).

REFERENCE EXAMPLE 7

In 15 ml of dry dichloromethane is dissolved 100.0 mg (0.189 mmole) of dechloromaytansinol, and 69 mg (0.476 mmole) of N-acetyl-N-methyl-L-alanine, 117 mg (0.568 mmole) of DCC and 39 mg (0.287 mmole) of anhydrous zinc chloride are successively added in the order mentioned. After the mixture is stirred at the room temperature (ca. 23° C.) for 30 minutes, 55 mg (0.379 mmole) of N-acetyl-N-methyl-L-alanine, 98 mg (0.476 mmole) of DCC and 31 mg (0.228 mmole) of anhydrous zinc chloride are further added, and the mixture is stirred again at a room temperature for 2 hours. The insolubles are filtrated off, and the filtrate is washed with water, dried and concentrated to dryness. To the residue is added 30 ml of ethyl acetate and, insolubles are filtered off, then the filtrate is concentrated to dryness. The residue is dissolved in about 5 ml of ethyl acetate and chromatographed on a column of silica gel (25 mm of outer diameter×500 mm). Elution is carried out with ethyl acetate/ethyl acetate saturated with water (=2:1 v/v) and then with ethyl acetate saturated with water, and the eluate is collected in 15 g fractions. The fractions No. 55 through No. 103 are pooled, and the solvent is distilled off, whereupon 53 mg of crude dechloromaytansine is obtained. This residue is dissolved in ethyl acetate, to which solution is added with ether, followed by cooling. By the above procedure, there is obtained 24 mg of L-dechloromaytansine as colorless crystals. m.p. 184°–186° C. (decomp.).

The above chromatographic fractions No. 168 through No. 221 are pooled, and the solvent is distilled off to recover 65 mg of D-dechloromaytansine. The residue is dissolved in chloroform, and ether is added, followed by recovering the resulting crystals by filtration. By the above procedure, there is obtained 21 mg of D-dechloromaytansine as colorless microcrystals. m.p. 175°–178° C. (decomp.).

REFERENCE EXAMPLE 8

The following compounds can be produced in a similar manner to that described in Reference Example 7.

(A) From dechloromaytansinol and isobutyric anhydride, there is obtained dechloromaytansinol 3-isobutyrate as white prisms melting at 250°–252° C. (decomp.).

(B) From dechloromaytansinol and nicotinic acid, there is obtained dechloromaytansinol 3-nicotinate, m.p. 170°–173° C. (decomp.).

(C) From dechloromaytansinol and cyclohexanecarboxylic acid, there is obtained dechloromaytansinol 3-cyclohexanecarboxylate, m.p. 217°–220° C. (decomp.).

(D) From dechloromaytansinol and phenylacetic acid, there is obtained dechloromaytansinol 3-phenylacetate, m.p. 165°–170° C. (decomp.).

REFERENCE EXAMPLE 9

In 30 ml of dry dichloromethane is 150.0 mg (0.265 mmole) of maytansinol, followed by adding 24.0 mg (0.663 mmole) of N-acetyl-N-methyl-L-leucine and 174.2 mg (0.846 mmole) of dicyclohexylcarbodiimide (DCC). After the mixture is stirred at a room temperature for a while, 46 mg (0.338 mmole) of anhydrous zinc chloride is added, followed by stirring at the room temperature for 30 minutes. An additional 46 mg of anhydrous zinc chloride is added, and the mixture is stirred at the same temperature for about 45 minutes. Again, 104.3 mg (0.558 mmole) of N-acetyl-N-methyl-L-leucine, 141 mg (0.686 mmole) of DCC and 46 mg of anhydrous zinc chloride are added, followed by stirring at the same temperature for 2.5 hours. The reaction mixture is washed with water, and the organic layer is dried over Na$_2$SO$_4$, then the solvent is distilled. The residue is chromatographed on a column of silica gel (75 g), and elution is carried out with ethyl acetate (ca. 600 ml) and then with ethyl acetate saturated with water, the eluate being collected in 17 g fractions. The fractions No. 14 through No. 34 are pooled and, after the solvent is distilled off, the resulting residue (100 mg) is chromatographed on a column of silica gel (35 g) (solvent system: chloroform/methanol=60/1(v/v)), the eluate being collected in 25 g fractions. The fractions No. 16 through No. 30 are pooled, and the solvent is distilled off, followed by dissolving the residue in ethyl acetate. After cooling, the resultant crystals are recovered by filtration. By this procedure, there is obtained 89 mg of the compound A. The initial chromatographic fractions No. 35 through No. 56 and, after the solvent distilled off, the residue is chromatographed on silica gel (40 g) [solvent system: chloroform/methanol=60/1 (v/v) (ca. 200 ml), do. 40/1, 1 l; collected in 25 g fractions). The fractions No. 17 through No. 35 are pooled and, after the solvent is distilled off, the residue is dissolved in ethyl acetate. Following addition of diethyl ether, the resulting precipitate is recovered by filtration. By this procedure, there is obtained 52 mg of the compound B.

Both of the compounds A and B are the desired compounds and, based on the following physicochemical data, are considered to be maytansinol 3-(N-acetyl-N-methyl)-L-leucine ester and maytansinol 3-(N-acetyl-N-methyl)-D-leucine ester, respectively.

Compound A: m.p. 172°–175° C. (decomp.)
Compound B: m.p. 157°–159° C. (decomp.)

REFERENCE EXAMPLE 10

The following compounds can be produced in a similar manner to that described in Reference Example 9.
(A) From maytansinol and N-acetyl-N-benzyl-D-alanine, there is obtained maytansinol 3-(N-acetyl-N-benzyl)alanine ester as isomers only dissimilar with respect to the stereo-chemical arrangement of the 2'-substituent. m.p. 174°–177° C. (decomp.), 163°–166° C. (decomp.).
(B) From maytansinol and N-acetyl-N-methyl-L-phenylalanine, there is obtained maytansinol 3-(N-acetyl-N-methyl)phenylalanine ester as isomers only dissimilar with respect to the stereo-chemical arrangement of the 2'-substituent. m.p. 189°–193° C. (decomp.), 212°–214° C. (decomp.).
(C) From maytansinol and N-tert-butoxycarbonyl-N-methyl-L-alanine, there are obtained maytansinol 3-(N-tertbutyloxycarbonyl-N-methyl-L-alanine) ester [UV-spectrum ($\lambda_{max}^{MeOH}$) nm: 234, 244, 254, 282, 290] and maytansinol 3-(N-tert-butyloxycarbonyl-N-methyl-D-alanine) ester [UV-spectrum ($\lambda_{max}^{MeOH}$) nm: 234, 241(sh), 253.5, 282, 290].
(D) From maytansinol and N-acetylsarcosine, there is obtained maytansinol 3-(N-acetyl)sarcosine ester as a glassy substance.
NMR spectrum (CDCl$_3$) δ ppm: 0.87(3H, s), 1.28(3H, d, J=5 Hz), 1.68(3H, s), 2.14(3H, s), 2.19(1H, dd, J=3 Hz and 14 Hz), 2.55(1H, dd, J=11 Hz and 14 Hz), 2.76(1H, d, J=9 Hz), 3.07(2H, s), 3.13(3H, s), 3.18 (3H, s), 3.35(3H, s), 3.47(1H, d, J=9 Hz), 3.52(1H, d, J=13 Hz), 3.98(3H, s), 4.18(1H, m), 4.92(1H, dd, J=3 Hz and 11 Hz), 5.74(1H, dd, J=9 Hz and 15 Hz), 6.18(1H, d, J=11 Hz), 6.44(1H, dd, J=11 Hz and 15 Hz), 6.53(1H, s), 6.82(2H, s), etc.
(E) From maytansinol and N-acetylglycine, there is obtained maytansinol 3-(N-acetyl)-glycine ester, m.p. 189°–192° C. (decomp.).

REFERENCE EXAMPLE 11

In 80 ml of dichloromethane are dissolved maytansinol (300 mg, 0.5315 mmole) and N-acetyl-N-methyl-L-alanine (1.585 g, 10.62 mmole), followed by adding 3.285 g of dicyclohexylcarbodiimide and 72.5 mg (0.532 mmole) of anhydrous zinc chloride. The mixture is stirred at about 20° C. for 6 hours and, then, allowed to stand at that temperature for 11 hours. Then, N-acetyl-N-methyl-L-alanine (530 mg), dicyclohexylcarbodiimide (1095 mg) and anhydrous zinc chloride (150 mg) are further added. After 2 hours, the reaction mixture is filtered and, the filtrate is washed with about 150 ml of water and dried over anhydrous sodium sulfate. The insolubles are filtered off and, the filtrate is chromatographed on a column of silica gel (60 g), elution being carried out with chloroform/methanol (40:1, v/v). After discarding the forerun, the eluate is collected in 25 g fractions. The fractions No. 14 through No. 25 are pooled, concentrated and rechromatographed on silica gel (65 g), elution being carried out with ethyl acetate-/ethyl acetate saturated with water (=2/1, v/v). The forerun is discarded and the eluate is collected in 16 g fractions. The fractions No. 25 through No. 60 yield 149.3 mg of the compound A. The rechromatographic fractions Nos. 23 and 24 as well as No. 61 through No. 100 are pooled and concentrated to dryness to recover 20.5 mg of the product. This product is subjected to preparative silica gel TLC (Kieselgel 60F$_{254}$, Art. 5717), and the chromatogram is developed with 10% isopropanolchloroform to recover an additional 6.3 mg of the product A. The above rechromatographic fractions No. 101 through No. 105 are pooled and concentrated to obtain 320 mg of a product. The product is rechromatographed on a column of silica gel (75 g) (solvent: chloroform/methanol=40/1, v/v) to recover 95.7 mg of compound B which is an isomer of the compound A. The total yield of the compound A is 155.6 mg and that of the compound B is 95.7 mg.

The compound A was identified with naturally occurring maytansine (L-form) by comparison of the following data with data on natural maytansine as given in Journal of Organic Chemistry 42, No. 14, 2349–2357(1977). UV spectrum (λ max, EtOH) nm: 289, 281, 254, 242(sh), 233. Mass spectrum (m/e): 691, 630, 485, 470, 450, 128, 100, 58. $[\alpha]_D^{23}$ −136°±30° (c=0.055, CHCl$_3$)

The compound A was dissolved in a mixture of ethyl acetate and ether, and allowed to stand in a refrigerator, whereupon crystals were separated out. These crystals were recrystallized once from ethyl acetate-ether and, then, twice, from dichloromethane-ether. By the above procedure there was obtained the compound A as colorless plates melting at 191°–195° C. (decomp.).

The compound B was identified with an isomer of maytansine and assumed to be D-maytansine by comparison of the following data with the data on maytansine. UV spectrum (λ max, EtOH) nm: 289, 281, 253, 240(sh), 233. Mass spectrum (m/e): 691, 630, 485, 470, 450, 128, 100, 58. $[\alpha]_D^{23}$ −129°±30° (c=0.055, CHCl₃)

A solution of the compound B in chloroform was treated with ether to form crystals, which were then recrystallized twice from the same solvent system. By the above procedure there was obtained the compound B as crystals melting at 155°–178° C. (gradually decomposed).

REFERENCE EXAMPLE 12

The following compounds can be produced in a similar manner to that described in Reference Example 11.

(A) From maytansinol and N-methyl-N-propionyl-L-alanine, there are obtained natural type (L-form) maytanpurine [colorless needles, m.p. 185°–189° C. (slightly decomposed)] and D-maytanpurine [colorless needles, m.p. 192°–197° C. (decomp.)].

(B) From maytansinol and N-isobutyryl-N-methyl-L-alanine, there are obtained natural type (L-form) maytanbutine [colorless needles, m.p. 185°–187° C. (decomp.)] and D-maytanbutine [colorless needles, m.p. 195°–198° C. (decomp.)].

(C) From maytansinol and N-isovaleryl-N-methyl-L-alanine, there are obtained natural type (L-form) maytanvaline and D-maytanvaline.

NMR spectrum (CDCl₃) δ of natural type maytanvaline: 0.79(3H, s), 0.91(3H, d, J=6 Hz), 0.95(3H, d, J=6 Hz), 1.27(3H, d, J=6 Hz), 1.30(3H, d, J=7 Hz), 1.64(3H, s), 2.13 (2H, d, J=7 Hz), 2.15(1H, dd, J=14 Hz and 3 Hz), 2.60(1H, dd, J=14 Hz and 11 Hz), 2.83(3H, s), 3.00(1H, d, J=9 Hz), 3.07(1H, d, J=13 Hz), 3.17(3H, s), 3.34(3H, s), 3.47(1H, d, J=9 Hz), 3.59(1H, br.), 3.65(1H, d, J=13 Hz), 3.95(3H, s), 4.27(1H, m), 4.74(1H, dd, J=12 Hz and 3 Hz), 5.35(1H, q, J=7 Hz), 5.64(1H, dd, J=15 Hz and 9 Hz), 6.28(1H, br.,s), 6.39(1H, dd, J=15 Hz and 11 Hz), 6.67(1H, d, J=2 Hz), 6.69 (1H, d, J=11 Hz), 6.79(1H, d, J=2 Hz), 0.7–2.0(3H), Mass spectrum (m/e): 733, 672, 485, 470, 450, 170.

NMR spectrum (CDCl₃) δ of D-maytanvaline: 0.89(3H, s), 0.93(3H, d, J=6 Hz), 0.96(3H, d, J=6 Hz), 1.26(3H, d, J=4 Hz), 1.49(3H, d, J=7 Hz), 1.69(3H, s), 2.66(1H, dd, J=15 Hz and 12 Hz), 3.02(3H, s), 3.12(3H, s), 3.18(1H, d, J=13 Hz), 3.32(3H, s), 3.42(1H, d, J=9 Hz), 3.50(1H, d, J=13 Hz), 3.96(3H, s), 4.29(1H, m), 4.92(1H, dd, J=11 Hz and 3 Hz), 5.00(1H, q, J=7 Hz), 5.05(1H, br.), 5.78(1H, dd, J=15 Hz and 9 Hz), 6.17(1H, d, J=11 Hz), 6.24 (1H, s), 6.43(1H, dd, J=15 Hz and 11 Hz), 6.77(1H, d, J=1.5 Hz), 6.83(1H, d, J=1.5 Hz), 0.8–2.5(7H).

Mass spectrum (m/e): 733, 672, 485, 470, 450, 170.

REFERENCE EXAMPLE 13

(i) In 600 ml of methanol is suspended 53.5 g (0.52 mole) of N-methyl-L-alanine, and under ice-cooling and stirring, 76 g of dry hydrogen chloride gas is dissoled. The suspension of the starting material is liquidated with the progress of the reaction, and after stirring at the room temperature overnight, a homogeneous solution is obtained. After 85 g (0.8 mole) of methyl orthoformate is added, the reaction mixture is further allowed to stand at a room temperature for 24 hours. A small amount of insolubles is filtered off and the filtrate is concentrated under reduced pressure. By the above procedure there is obtained the hydrochloride of N-methyl-L-alanine methyl ester as a solid product.

NMR spectrum (in DMSO-d₆) δ: 1.50(3H, d, J=7 Hz), 2.60(3H, m; after addition of D₂O, s), 3.75(3H, s), 4.12(1H, m; after addition of D₂O, q, J=7 Hz), 9.83(2H, br.).

(ii) In 300 ml of chloroform is dissolved 33.7 g (0.22 mole) of N-methyl-L-analine methyl ester.hydrochloride, followed by the addition of 65 ml of acetic anhydride and 110 ml of triethylamine. The mixture is allowed to stand at a room temperature for 24 hours and, after the excess of acetic anhydride is decomposed with water, is neutralized with sodium hydrogen carbonate. The chloroform layer is separated and, the water layer is extracted with ethyl acetate (120 ml×5), followed by combining the chloroform and ethyl acetate layers to concentrate under reduced pressure. The brown, oily substance obtained is dissolved in chloroform, washed with aqueous sodium hydrogen carbonate and concentrated under reduced pressure. By the above procedure, there is obtained 31.8 g of N-acetyl-N-methyl-L-alanine methyl ester as brown oil.

NMR spectrum (CDCl₃): 1.38(3H, d, J=7 Hz), 2.12(3H, s), 2.97(3H, s), 3.70(3H, s), 5.23(1H, g, J=7 Hz).

The ester obtained above is dissolved in a mixture of 100 ml methanol and 170 ml 1 N-aqueous sodium hydroxide. The solution is allowed to stand at a room temperature for 2 hours, and the methanol is removed under reduced pressure. The alkaline aqueous solution is extracted with chloroform. The water layer is brought to pH 1 with concentrated hydrochloric acid under ice-cooling and extracted with ethyl acetate (140 ml×5). The extract is dried over anhydrous sodium sulfate and concentrated under reduced pressure to recover a white solid. Recrystallization from ethyl acetate-hexane yields 8.1 g of N-acetyl-N-methyl-L-alanine as colorless needles.

$[\alpha]_D^{25}$ −58.5° (c=1, DMF)
−74.3° (c=1, H₂O)
m.p. 121°–122° C.

(iii) The following compounds can be produced in a similar manner to that described above.

(A) From N-methyl-L-alanine methyl ester.hydrochloride and propionic anhydride, there is obtained N-methyl-N-propionyl-L-alanine (colorless prisms), m.p. 108°–110° C.

(B) From N-methyl-L-alanine methyl ester.hydrochloride and isobutyryl chloride, there is obtained N-isobutyryl-N-methyl-L-alanine (colorless prisms), m.p. 117°–118° C.

(C) From N-methyl-L-alanine methyl ester.hydrochloride and isovaleryl chloride, there is obtained N-methyl-N-isovaleryl-L-alanine (colorless scales), m.p. 88°–89° C.

REFERENCE EXAMPLE 14

(i) Production of β-methoxycarbonylethyl isocyanate.

In 600 ml of dry toluene is dissolved 26.4 g of monomethyl succinate, followed by adding 55 g of diphenylphosphorylazide and 22 g of triethylamine. The mixture is allowed to stand at the room temperature with stirring for 3 hours, and is washed with water and dried. The solvent is concentrated to about one third of its original volume and, finally, the mixture is refluxed for 2 hours. After the solvent is completely evaporated off, the residue is distilled under reduced pressure. By the above procedure, there is obtained 13.6 g of the above-indicated compound.

b.p.$^8$: 64°–66° C.

(ii) Production of 5-dimethylaminopentyl isocyanate.

In 136 ml of ethanol are dissolved 23.5 g of methyl 6-N,N-dimethylaminocaproate and 10.2 g of Hydrazine hydrate and the solution is allowed to stand under reflux overnight. To the reaction mixture is added an excess of ethanolic oxalic acid, and the white precipitate is recovered by filtration and extracted with 300 ml of 50% aqueous ethanol while hot. After cooling, some insoluble matters are removed and the filtrate is concentrated to dryness, whereupon 23.3 g of white powder is obtained. The entire amount of this powdery residue is suspended in 136 ml of water, and treated under cooling with 12.3 g of sodium nitrite. The reaction mixture is adjusted to pH 10.5 with 5 N-sodium hydroxide and extracted three times with 150 ml of benzene each. The benzene layers are combined, washed with water, dried, and kept under reflux for an hour. The solvent is carefully evaporated off, and the residue is distilled under reduced pressure. By the above procedure there is obtained 6.1 g of the above indicated compound, b.p.$^{14}$: 110°–115° C.

REFERENCE EXAMPLE 15

In 10 ml of dry dichloromethane is dissolved 56 mg (0.099 mmole) of maytansinol, followed by adding 24 mg (0.202 mmole) of phenyl isocyanate. At the room temperature (18°–23° C.), 30 mg (0.221 mmole) of anhydrous zinc chloride is added, and the mixture is stirred at that temperature for 3 hours. The reaction mixture is washed with water, dried (Na$_2$SO$_4$) and concentrated. The residue is chromatographed on silica gel [solvent system: ethyl acetate/ethyl acetate saturated with water=4/1 (v/v) through 3/1 (v/v)], the eluate being collected in 17 g fractions. Fractions No. 9 through No. 17 are pooled and the solvent is distilled off. By the above procedure there is obtained 58 mg of maytansinol 3-N-phenylcarbamate.

m.p. 187°–189° C. (recrystallized from ethyl acetate-hexane).

REFERENCE EXAMPLE 16

In 10 ml of dichloromethane is dissolved 54 mg (0.0956 mmole) of maytansinol, followed by adding 50 mg (0.877 mmole) of methyl isocyanate and 30 mg of cuprous chloride. The reaction mixture is stirred at a room temperature for 4 hours, after which it is filtered and concentrated. The residue is chromatographed on a column (25 mm diameter×45 cm long) of silica gel and elution is carried out with chloroform/methanol (40/1, v/v), the eluate being collected in 25 g fractions. The fractions No. 34 through No. 44 are pooled and concentrated to dryness to obtain 44 mg of white glassy substance. The substance is reprecipitated from chloroform-hexane. By the above procedure there is obtained 28 mg of maytansinol 3-(N-methyl)carbamate 9-(2-,4-dimethyl)allophanate as white powder m.p. 149°–151° C. (decomp.).

In 0.2 ml of dichloromethane is dissolved 10 mg of maytansinol 3-(N-methyl)carbamate 9-(2,4-dimethyl)allophanate and, two drops of trifluoroacetic acid is added. The reaction mixture is stirred at a room temperature for 5 minutes and after addition of a further amount of dichloromethane, it is washed with aqueous sodium hydrogen carbonate. The solvent is distilled off, and the residue is chromatographed on 12 g of silica gel. By the above procedure there is obtained 5.2 mg of maytansinol 3-(N-methyl)carbamate.

REFERENCE EXAMPLE 17

The following compounds can be produced in a similar manner to that described in Reference Examples 14 through 16.

(A) From maytansinol and methyl isocyanate, there is obtained maytansinol 3-(N-methyl)carbamate, m.p. 196°–200° C. (decomp.).

(B) From maytansinol and butyl isocyanate, there is obtained maytansinol 3-(N-butyl)carbamate, m.p. 162°–165° C.

(C) From maytansinol and octadecyl isocyanate, there is obtained maytansinol 3-(N-octadecyl)carbamate, m.p. 105°–109° C.

(D) From maytansinol and cyclohexyl isocyanate, there is obtained maytansinol 3-(N-cyclohexyl)carbamate, m.p. 175°–178° C.

(E) From maytansinol and α-naphthyl isocyanate, there is obtained maytansinol 3-(N-α-naphthyl)carbamate, m.p. 172°–175° C.

(F) From maytansinol and p-ethoxyphenyl isocyanate, there is obtained maytansinol 3-(N-p-ethoxyphenyl)carbamate, m.p. 221°–223° C.

(G) From dechloromaytansinol and phenyl isocyanate, there is obtained dechloromaytansinol 3-(N-phenyl) carbamate as a colorless glassy substance.

NMR spectrum (CDCl$_3$) δ ppm: 0.87(3H, s), 1.26(3H, d, J=6 Hz), 1.70(3H, s), 2.03(3H, s), 2.23(1H, dd, J=2.5 Hz and 14 Hz), 2.69(1H, dd, J=11 Hz and 14 Hz), 2.87(1H, d, J=9 Hz), 3.23(3H, s), 3.30(3H, s), 3.42(1H, d, J=9 Hz), 3.49(1H, d, J=14 Hz), 3.85(3H, s), 4.30(1H, m), 4.78(1H, dd, J=2.5 Hz and 11 Hz), 5.37(1H, dd, J=9 Hz and 15 Hz), 6.10(1H, d, J=10.5 Hz), 6.39(1H, s), 6.43 (1H, dd, J=10.5 Hz and 15 Hz), 6.57–7.56(ca. 9H, m), etc.

(H) From maytansinol and isopropyl isocyanate, there is obtained maytansinol 3-isopropylcarbamate. Mass spectrum (m/e), 588 (M+ −61).

(I) From maytansinol and pyridyl-3-isocyanate, there is obtained maytansinol 3-(m-pyridyl)carbamate. Mass spectrum (m/e), 623 (M+ −61).

(J) From maytansinol and 5-dimethylaminopentyl isocyanate, there is obtained maytansinol 3-(5-dimethylamino)pentylcarbamate. Mass spectrum (m/e), 659(M+ −61).

(K) From maytansinol and β-methoxycarbonylethyl isocyanate, there is obtained maytansinol 3-(β-methoxycarbonylethyl)carbamate. Mass spectrum (m/e), 632 (M+ −61).

(L) From maytansinol and N,N-dimethylcarbamoyl chloride, there is obtained maytansinol 3-N,N-dimethylcarbamate. Rf=0.39(solvent: chloroform/methanol=95/5); mass spectrum (m/e), 574(M+ −61).

REFERENCE EXAMPLE 18

*Bacillus megaterium* IFO 12108 is inoculated into a culture medium (pH 7.5) containing 2% dextrin, 0.5% peptone, 0.5% yeast extract and 0.5% meat extract, and the inoculated medium is shake-cultured at 30° C. for 16 hours. To 2.75 l of this culture is added 110 mg of ansamitocin P-4 and, the reaction is carried out under shaking at 30° C. for 51 hours. As assayed by thin-layer chromatography (TLC), the ansamitocine P-4 has disappeared completely and, instead, PDM-4 has been produced in the reaction mixture.

To 2.75 l of the above culture broth is added 1.3 l of ethyl acetate, and the mixture is stirred to extract. The mixture is suction-filtered through a filter coated with 30 g of Hyflo Super Cel (Johns-Manville Products Co., Inc. U.S.A.). This procedure is repeated twice. The ethyl acetate layers are combined, washed twice with 800 ml of 1/200 N-HCl and 400 ml of 0.5% aqueous sodium hydrogen carbonate in that order, and washed twice with 400 ml portions of water. It is dried with 10 g of anhydrous sodium sulfate and concentrated under reduced pressure to 2 ml. To this residue is added 50 ml of petroleum ether, and the resultant precipitate is recovered by filtration (126 mg). The crude product (i) of PDM-4 thus obtained is dissolved in a small amount of chloroform and run onto a column (1 cm diameter) of 5 g of silica gel (0.05-0.2 mm). Elution is carried out with 100 ml of chloroform, 100 ml of chloroform/methanol (40:1) and 200 ml of chloroform/methanol (20:1), the elutate being collected in 10 ml fractions. Each fraction is spotted to a silica gel-glass plate (Kieselgel 60F$_{254}$, 0.25 mm, 20×20) at a distance of 2.5 cm from the bottom end, and the chromatogram is developed over about 17 cm with ethyl acetatemethanol (19:1) to locate absorption spots by irradiation of UV ray (2537 A). The fractions No. 13 through No. 17 which show the absorption in the region of the Rf value of 0.64 are combined and concentrated under reduced pressure to about 1 ml. To the concentrate is added 30 ml of petroleum ether, whereby 79 mg of the crude product (ii) of PDM-4 is obtained.

79 mg of the crude product of PDM-4 obtained in the above is dissolved in a small amount of chloroform, and the solution is linearly applied to each of four silica gel glass plate (Kieselgel F$_{254}$, 2 mm, 20×20) at a distance of 2.5 cm from its bottom end. Each chromatogram is developed with ethyl acetate-methanol (19:1), and the corresponding absorption band of silica gel located at Rf of 0.64 is scraped off and extracted twice with ethyl acetate containing a small amount of water. The ethyl acetate extract thus obtained is washed with water, dried over anhydrous sodium sulfate, concentrated under reduced pressure, and treated with petroleum ether. By the above procedure, there is obtained 68 mg of PDM-4 as white powder, m.p. 185°-188° C.

REFERENCE EXAMPLE 19

The following compounds can be produced with the use of *Bacillus megaterium* IFO 12108 in a similar manner to that described in Reference Example 18.
(A) From maytansinol is obtained demethylmaytansinol as white powder, m.p. 194°-196° C.
(B) From maytansinol propionate is obtained demethylmaytansinol propionate, m.p. 193°-195° C.

REFERENCE EXAMPLE 20

A culture medium (pH 7.2) containing 1% dextrin, 1% glucose, 1% glycerine, 0.5% peptone, 0.5% yeast extract, 0.5% meat extract, 0.3% sodium chloride and 0.5% calcium carbonate is inoculated with *Streptomyces flavotricini* IFO 12770 and the medium is cultured under shaking at 28° C. for 48 hours. To 2 l of the resultant culture is added 20 mg of ansamitocin P-3, and the reaction is carried out under shaking at 28° C. for 48 hours. The culture broth is purified in a similar manner to that described in Reference Example 18. By the above procedure there is obtained 12 mg of PDM-3 as a white powder, m.p. 165°-168° C.

REFERENCE EXAMPLE 21

To the culture broth of *Streptomyces flavotricini* IFO 12770 obtained in a similar manner to that described in Reference Example 20 is added maytanacine, followed by carrying out the reaction and purification as Reference Example 18. By the above procedure there is obtained demethylmaytanacine, m.p. 224°-226° C.

REFERENCE EXAMPLE 22

The following compounds can be produced with the use of *Bacillus megaterium* IFO 12108 in a similar manner to that given in Reference Example 18.
(A) From maytansinol 3-picolinate is obtained demethylmaytansinol 3-picolinate.
UV spectrum ($\lambda_{max}^{MeOH}$) nm: 232, 243, 252, 280, 289.
Mass spectrum (m/e): 655, 594, 471, 456, 436.
(B) From maytansinol 3-phenylcarbamate is obtained demethylmaytansinol 3-phenylcarbamate.
UV spectrum ($\lambda_{max}^{MeOH}$) nm: 233, 252, 280, 288.
Mass spectrum (m/e): 608, 471, 456, 436.
(C) From dechloromaytansinol 3-phenylacetate is obtained demethyldechloromaytansinol 3-phenylacetate.
UV spectrum ($\lambda_{max}^{MeOH}$) nm: 230, 240, 249, 277, 285.
Mass spectrum (m/e): 634(M+), 573, 437, 422.
(D) From maytansinol 3-hexanoate is obtained demethylmaytansinol 3-hexanoate.
UV spectrum ($\lambda_{max}^{MeOH}$) nm: 233, 240, 252, 280, 289.
Mass spectrum (m/e): 587, 471, 456, 436.
(E) From maytansinol 3-p-chlorobenzoate is obtained demethylmaytansinol 3-p-chlorobenzoate.
UV spectrum ($\lambda_{max}^{MeOH}$) nm: 240, 252, 280, 289
Mass spectrum (m/e): 627, 471, 456, 436
(F) From dechloromaytansinol 3-isobutyrate is obtained demethyldechloromaytansinol 3-isobutyrate, m.p. 213°-215° C.

REFERENCE EXAMPLE 23

The following compound can be produced with the use of *Streptomyces flavotricini* IFO 12770 in a similar manner to that described in Reference Example 20.
(A) From maytansinol 3-cyclohexanecarboxylate is obtained dechloromaytansinol 3-cyclohexanecarboxylate.
UV spectrum ($\lambda_{max}^{MeOH}$) nm: 233, 240, 252, 280, 289.
Mass spectrum (m/e): 599, 471, 456, 436.

REFERENCE EXAMPLE 24

The following compounds can be produced with the use of *Streptomyces platensis* IFO 12901 in a similar manner to that described in Reference Example 20.
(A) From maytansinol 3-phenylacetate is obtained demethylmaytansinol 3-phenylacetate.
UV spectrum ($\lambda_{max}^{MeOH}$): 233, 240, 252, 280, 289.
Mass spectrum (m/e): 607, 471, 456, 436.
(B) From L-maytansine is obtained L-demethylmaytansine. m.p. 194°-196° C.
Specific rotation: −117.9° (c=0.56, EtOH).
Mass spectrum (m/e): 616, 471, 456, 436, 128.
UV spectrum ($\lambda_{max}^{MeOH}$) nm: 288, 281, 252, 243, 232
(C) From D-maytansine is obtained D-methylmaytansine.
Mass spectrum (m/e): 616, 471, 456, 436, 128.
UV spectrum ($\lambda_{max}^{MeOH}$) nm: 288, 281, 252, 243, 232.

REFERENCE EXAMPLE 25

The following compounds can be produced with the use of *Actinomyces nigrescens* IFO 12894 in a similar manner to that described in Reference Example 20.

(A) From maytanpurine (D, L) are obtained L-demethylmaytanpurine and D-demethylmaytanpurine, respectively.
(i) L-demethylmaytanpurine
Mass spectrum (m/e): 630, 471, 456, 436, 142.
UV spectrum ($\lambda_{max}^{MeOH}$) nm: 288, 281, 252, 243, 232.
(ii) D-demethylmaytanpurine
Mass spectrum (m/e): 630, 471, 456, 436, 142.
UV spectrum ($\lambda_{max}^{MeOH}$) nm: 288, 281, 252, 243, 232.
(B) From maytanbutine (D, L), there are obtained L-demethylmaytanbutine and D-demethylmaytanbutine, respectively.
(i) L-demethylmaytanbutine
Mass spectrum (m/e): 644, 471, 456, 436, 156.
UV spectrum ($\lambda_{max}^{MeOH}$) nm: 288, 281, 252, 243, 232.
(ii) D-demethylmaytanbutine
Mass spectrum (m/e): 644, 471, 456, 436, 156.
UV spectrum ($\lambda_{max}^{MeOH}$) nm: 288, 281, 252, 243, 232.
(C) From maytanvaline (D, L) there are obtained L-demethylmaytanvaline and D-demethylmaytanvaline, respectively.
(i) L-demethylmaytanvaline
Mass spectrum (m/e): 658, 471, 456, 436, 170.
UV spectrum ($\lambda_{max}^{MeOH}$) nm: 288, 281, 252, 243, 232.
(ii) D-demethylmaytanvaline
Mass spectrum (m/e): 658, 471, 456, 436, 170.
UV spectrum ($\lambda_{max}^{MeOH}$) nm: 288, 281, 252, 243, 232.

REFERENCE EXAMPLE 26

The following compounds can be produced with the use of *Bacillus megaterium* IFO 12108 in a similar manner to that described in Reference Example 18: below tabulated are the starting compounds, product compounds and the Rf values of the product compounds [developing solvent: CHCl$_3$/MeOH=9/1; plate: silica gel glass plate Kieselgel 60F$_{254}$, thickness of 0.25 mm)].

| Starting compound (XIV) | Product compound (II) | Rf value |
|---|---|---|
| Maytansinol | Demethylmaytansinol | 0.30 |
| Maytanacine | Demethylmaytanacine | 0.38 |
| Maytansinol propionate | Demethylmaytansinol propionate | 0.40 |
| Ansamitocin P-3 | PDM-3 | 0.42 |
| Ansamitocin P-3' | PDM-3' | 0.43 |
| Ansamitocin P-4 | PDM-4 | 0.44 |
| Maytansinol 3-valerate | Demethylmaytansinol 3-valerate | 0.45 |
| Maytansinol 3-hexanoate | Demethylmaytansinol 3-hexanoate | 0.48 |
| Maytansinol 3-heptanoate | Demethylmaytansinol 3-heptanoate | 0.49 |
| Maytansinol 3-octanoate | Demethylmaytansinol 3-octanoate | 0.50 |
| Maytansinol 3-phenylacetate | Demethylmaytansinol 3-phenylacetate | 0.43 |
| Maytansinol 3-phenylpropionate | Demethylmaytansinol 3-phenylpropionate | 0.45 |
| Maytansinol 3-benzoate | Demethylmaytansinol 3-benzoate | 0.42 |
| Maytansinol 3-cyclohexanecarboxylate | Demethylmaytansinol 3-cyclohexanecarboxylate | 0.45 |
| Maytansinol 3-p-chlorobenzoate | Demethylmaytansinol 3-p-chlorobenzoate | 0.43 |
| Maytansinol 3-nicotinate | Demethylmaytansinol 3-nicotinate | 0.31 |
| Maytansinol 3-isonicotinate | Demethylmaytansinol 3-isonicotinate | 0.30 |
| Maytansinol 3-picolinate | Demethylmaytansinol 3-picolinate | 0.40 |
| Maytansinol 3-(2-furan)carboxylate | Demethylmaytansinol 3-(2-furan)carboxylate | 0.38 |
| Maytansinol 3-cyclopropanecarboxylate | Demethylmaytansinol 3-cyclopropanecarboxylate | 0.39 |
| Dechloromaytansinol | Demethyldechloromaytansinol | 0.28 |
| Dechloromaytansinol 3-isobutyrate | Demethyldechloromaytansinol 3-isobutyrate | 0.42 |
| Dechloromaytansinol 3-phenylacetate | Demethyldechloromaytansinol 3-phenylacetate | 0.43 |
| Dechloromaytansinol 3-nicotinate | Demethyldechloromaytansinol 3-nicotinate | 0.31 |
| Dechloromaytansinol 3-cyclohexanecarboxylate | Demethyldechloromaytansinol 3-cyclohexanecarboxylate | 0.45 |
| D-maytanvaline | Demethyl-D-maytanvaline | 0.47 |
| Maytansinol 3-(N-methyl)carbamate | Demethylmaytansinol 3-(N-methyl)carbamate | 0.27 |
| Maytansinol 3-(N-butyl)carbamate | Demethylmaytansinol 3-(N-butyl)carbamate | 0.39 |
| Maytansinol 3-(N-phenyl)carbamate | Demethylmaytansinol 3-(N-phenyl)carbamate | 0.40 |
| Maytansinol 3-(N-cyclohexyl)carbamate | Demethylmaytansinol 3-(N-cyclohexyl)carbamate | 0.39 |
| Maytansinol 3-(3-pyridyl)carbamate | Demethylmaytansinol 3-(3-pyridyl)carbamate | 0.22 |

REFERENCE EXAMPLE 27

The following compounds are obtained with the use of *Streptomyces flavotricini* IFO 12770 in a similar manner to that described in Reference Examples 18 or 20: below tabulated are the starting compounds, product compounds and the Rf values of the product compounds [developing solvent: CHCl$_3$/MeOH=9/1; plate: silica gel glass plate Kieselgel 60F$_{254}$, thickness of 0.25 mm)].

| Starting compound (XIV) | Product compound (II) | Rf value |
|---|---|---|
| Maytansinol | Demethylmaytansinol | 0.30 |
| Maytanacine | Demethylmaytanacine | 0.38 |
| Maytansinol propionate | Demethylmaytansinol propionate | 0.40 |
| Ansamitocin P-3 | PDM-3 | 0.42 |
| Ansamitocin P-3' | PDM-3' | 0.43 |
| Ansamitocin P-4 | PDM-4 | 0.44 |
| Maytansinol 3-valerate | Demethylmaytansinol 3-valerate | 0.45 |
| Maytansinol 3-hexanoate | Demethylmaytansinol 3-hexanoate | 0.48 |
| Maytansinol 3-heptanoate | Demethylmaytansinol 3-heptanoate | 0.44 |
| Maytansinol 3-octanoate | Demethylmaytansinol 3-octanoate | 0.50 |
| Maytansinol 3-phenylacetate | Demethylmaytansinol 3-phenylacetate | 0.43 |
| Maytansinol 3-phenylpropionate | Demethylmaytansinol 3-phenylpropionate | 0.45 |
| Maytansinol 3-benzoate | Demethylmaytansinol 3-benzoate | 0.42 |
| Maytansinol 3-cyclohexanecarboxylate | Demethylmaytansinol 3-cyclohexanecarboxylate | 0.45 |
| Maytansinol 3-p-chlorobenzoate | Demethylmaytansinol 3-p-chlorobenzoate | 0.43 |
| Maytansinol 3-nicotinate | Demethylmaytansinol 3-nicotinate | 0.31 |
| Maytansinol 3-isonicotinate | Demethylmaytansinol 3-isonicotinate | 0.30 |
| Maytansinol 3-picoliate | Demethylmaytansinol 3-picolinate | 0.40 |
| Maytansinol 3-(2-furan)carboxylate | Demethylmaytansinol 3-(2-furan)- | 0.38 |

-continued

| Starting compound (XIV) | Product compound (II) | Rf value |
|---|---|---|
| Maytansinol 3-cyclopropanecarboxylate | Demethylmaytansinol 3-cyclopropanecarboxylate | 0.39 |
| Dechloromaytansinol 3-isobutyrate | Demethyldechloromaytansinol 3-isobutyrate | 0.42 |
| Dechloromaytansinol 3-phenylacetate | Demethydechloromaytansinol 3-phenylacetate | 0.43 |
| Dechloromaytansinol 3-nicotinate | Demethyldechloromaytansinol 3-nicotinate | 0.31 |
| Dechloromaytansinol 3-cyclohexanecarboxylate | Demethyldechloromaytansinol 3-cyclohexanecarboxylate | 0.45 |
| Maytansinol 3-(N-acetyl-N-benzyl)alanine ester [m.p.174–177° C.(decomp.)] | Demethylmaytansinol 3-(N-acetyl-N-benzyl)-alanine ester | 0.46 |
| Maytansinol 3-(N-acetyl-N-methyl)-L-leucine ester | Demethylmaytansinol 3-(N-acetyl-N-methyl)-L-leucine ester | 0.43 |
| Maytansinol 3-(N-acetyl-N-methyl)phenylalanine ester [m.p.189–193° C.(decomp.)] | Demethylmaytansinol 3-(N-acetyl-N-methyl)-phenylalanine ester | 0.45 |
| L-maytansine | Demethyl-L-maytansine | 0.39 |
| D-maytansine | Demethyl-D-maytansine | 0.39 |
| L-maytanpurine | Demethyl-L-maytanpurine | 0.43 |
| D-maytanpurine | Demethyl-D-maytanpurine | 0.44 |
| L-maytanbutine | Demethyl-L-maytanbutine | 0.44 |
| D-maytanbutine | Demethyl-E-maytanbutine | 0.46 |
| D-maytanvaline | Demethyl-D-maytanvaline | 0.47 |
| Dechloro-D-maytansine | Demethyldechloro-D-maytansine | 0.39 |
| Maytansinol 3-(N-methyl) carbamate | Demethylmaytansinol 3-(N-methyl)carbamate | 0.27 |
| Maytansinol 3-(N-butyl) carbamate | Demethylmaytansinol 3-(N-butyl)carbamate | 0.39 |
| Maytansinol 3-(N-phenyl) carbamate | Demethylmaytansinol 3-(N-phenyl)carbamate | 0.40 |
| Maytansinol 3-(N-cyclohexyl)carbamate | Demethylmaytansinol 3-(N-cyclohexyl)-carbamate | 0.39 |
| Maytansinol 3-(pyridyl)carbamate | Demethylmaytansinol 3-(pyridyl)carbamate | 0.22 |

REFERENCE EXAMPLE 28

The following compounds are obtained with the use of *Streptomyces platensis* IFO 12901 in a similar manner to that described in Reference Examples 18 or 20: below tabulated are the starting compounds, product compounds and the Rf values of the product compounds [developing solvent: $CHCl_3/MeOH = 9/1$; plate: silica gel glass plate (Kieselgel 60F$_{254}$ thickness of 25 mm)].

| Starting compound (XIV) | Product compound (II) | Rf value |
|---|---|---|
| Maytanacine | Demethylmaytanacine | 0.38 |
| Maytansinol propionate | Demethylmaytansinol propionate | 0.40 |
| Ansamitocin P-3 | PDM-3 | 0.42 |
| Ansamitocin P-3' | PDM-3' | 0.43 |
| Ansamitocin P-4 | PDM-4 | 0.44 |
| Maytansinol 3-valerate | Demethylmaytansinol 3-valerate | 0.45 |
| Maytansinol 3-hexanoate | Demethylmaytansinol 3-hexanoate | 0.48 |
| Maytansinol 3-heptanoate | Demethylmaytansinol 3-heptanoate | 0.49 |
| Maytansinol 3-octanoate | Demethylmaytansinol 3-octanoate | 0.50 |
| Maytansinol 3-phenylacetate | Demethylmaytansinole 3-phenylacetate | 0.43 |
| Maytansinol 3-phenylpropionate | Demethylmaytansinol 3-phenylpropionate | 0.45 |
| Maytansinol 3-benzoate | Demethylmaytansinol 3-benzoate | 0.42 |
| Maytansinol 3-cyclohexanecarboxylate | Demethylmaytansinol 3-cyclohexanecarboxylate | 0.45 |
| Maytansinol 3-p-chlorobenzoate | Demethylmaytansinol 3-p-chlorobenzoate | 0.43 |
| Maytansinol 3-nicotinate | Demethylmaytansinol 3-nicotinate | 0.31 |
| Maytansinol 3-isonicotinate | Demethylmaytansinol 3-isonicotinate | 0.30 |
| Maytansinol 3-picolinate | Demethylmaytansinol 3-picolinate | 0.40 |
| Maytansinol 3-cyclopropanecarboxylate | Demethylmaytansinol 3-cyclopropanecarboxylate | 0.39 |
| Dechloromaytansinol 3-isobutyrate | Demethyldechloromaytansinol 3-isobutyrate | 0.42 |
| Dechloromaytansinol 3-phenylacetate | Demethyldechloromaytansinol 3-phenylacetate | 0.43 |
| Dechloromaytansinol 3-nicotinate | Demethyldechloromaytansinol 3-nicotinate | 0.31 |
| Dechloromaytansinol 3-cyclohexanecarboxylate | Demethyldechloromaytansinol 3-cyclohexanecarboxylate | 0.45 |
| Maytansinol 3-(N-acetyl-N-benzyl)alanine ester [m.p. 174–177° C.(decomp.)] | Demethylmaytansinol 3-(N-acetyl-N-benzyl)-alanine ester | 0.46 |
| Maytansinol 3-(N-acetyl-N-benzyl)alanine ester [m.p. 163–166° C.(decomp.)] | Demethylmaytansinol 3-(N-acetyl-N-benzyl)-alanine ester | 0.45 |
| Maytansinol 3-(N-acetyl-N-methyl)-L-leucine ester | Demethylmaytansinol 3-(N-acetyl-N-methyl)-L-leucine ester | 0.43 |
| Maytansinol 3-(N-acetyl-N-methyl)phenylalanine ester [m.p.189–193° C.(decomp.)] | Demethylmaytansinol 3-(N-acetyl-N-methyl)-phenylalanine ester | 0.45 |
| Maytansinol 3-(N-acetyl-N-methyl)phenylalanine ester [m.p.212–214° C.(decomp)] | Demethylmaytansinol 3-(N-acetyl-N-methyl)-phenylalanine ester | 0.42 |
| L-maytansine | Demethyl-L-maytansine | 0.39 |
| D-meytansine | Demethyl-D-maytansine | 0.39 |
| L-maytanpurine | Demethyl-L-maytanpurine | 0.43 |
| D-maytanpurine | Demethyl-D-maytanpurine | 0.44 |
| L-maytanbutine | Demethyl-L-maytanbutine | 0.44 |
| D-maytanbutine | Demethyl-D-maytanbutine | 0.46 |
| L-maytanvaline | Demethyl-L-maytanvaline | 0.45 |
| D-maytanvaline | Demethyl-D-maytanvaline | 0.47 |
| Dechloro-D-maytansine | Demethyldechloro-D-maytansine | 0.39 |
| Maytansinol 3-(N-butyl)-carbamate | Demethylmaytansinol 3-(N-butyl)carbamate | 0.39 |
| Maytansinol 3-(N-phenyl)-carbamate | Demethylmaytansinol 3-(N-phenyl)carbamate | 0.40 |
| Maytansinol 3-(N-cyclohexyl)carbamate | Demethylmaytansinol 3-(N-cyclohexyl)-carbamate | 0.39 |
| Maytansinol 3-(3-pyridyl) carbamate | Demethylmaytansinol 3-(3-pyridyl)carbamate | 0.22 |

REFERENCE EXAMPLE 29

In 20 ml of tetrahydrofuran is dissolved 50 mg of crystals of demethyldechloromaytansinol 3-isobutyrate and, after cooling to −5° C., 50 mg of lithium aluminium hydride is added. The reaction mixture is transferred in an ice bath, and stirred for 30 minutes. Following addition of 10 ml each of ethyl acetate and 1/200 N hydrochloric acid, 50 ml of ethyl acetate is further added to conduct extraction. The ethyl acetate layer is washed with water, dried over added anhydrous sodium sulfate, and concentrated under reduced pressure to carry out preparative TLC on silica gel. The chromatogram is developed over a distance of 17 cm with ethyl acetate/methanol (19:1), and the absorbing zone of silica gel at Rf=0.20 to 0.25 is scraped off and extracted with ethyl acetate containing a small amount of water. The extract is washed with water, dried over anhydrous sodium sulfate and concentrated under reduced pressure. By the above procedure, there is obtained 43 mg of demethyldechloromaytansinol as a powdery residue. The compound is dissolved in a small amount of ethyl acetate and, there are deposited crystals from the solution upon standing. The crystals are collected by filtration and dried. Yield 33 mg. m.p. 198°–201° C. (decomp.).

REFERENCE EXAMPLE 30

The following compounds are obtained in a similar manner to that described in Reference Example 29.
(A) From L-demethylmaytansine there is obtained demethylmaytansinol. m.p. 195° C.
(B) From D-demethylmaytansine there is obtained demethylmaytansinol. m.p. 196° C.
(C) From Demethylmaytanacine there is obtained demethylmaytansinol. m.p. 194°–196° C.
(D) From demethylmaytansinol propionate there is obtained demethylmaytansinol. m.p. 194°–196° C.
(E) From PDM-3 there is obtained demethylmaytansinol. m.p. 194°–196° C.
(F) From PDM-4 there is obtained demethylmaytansinol. m.p. 194°–196° C.
(G) From demethylmaytansinol 3-(N-phenyl)carbamate there is obtained demethylmaytansinol. m.p. 194° C.

REFERENCE EXAMPLE 31

Production of maytansinol 3-isopropylcarbonate.

In 2.0 ml of dry tetrahydrofuran is dissolved 57 mg of maytansinol, and the solution is treated under a stream of nitrogen with 5 mole equivalents of 15% n-butyllithium (in a n-hexane solution). After adding 61 mg of isopropyl chloroformate to the solution, the reaction mixture is stirred for 15 minutes and allowed to stand to be brought back to the temperature of 0° C. Following addition of 0.5 ml of saturated sodium chloride and 20 ml of tetrahydrofuran, the organic layer is taken and dried to evaporate off the solvent. Separation and purification of the residue by silica gel column chromatography yields 5 mg of maytansinol 3-isopropylcarbonate. Silica gel thin layer chromatography (HPTLC): Rf=0.44 (developing solvent; chloroform/methanol=95:5), MS-spectrum (m/e): 650($M^+$), 589($M^+$-61).

REFERENCE EXAMPLE 32

The following compounds are obtained in a similar manner to that described in Reference Example 31.
(A) From maytansinol and n-octyl chloroformate there is obtained maytansinol 3-n-octylcarbonate. Silica gel thin layer chromatography (HPTLC produced by Merck): Rf=0.61 (developing solvent; chloroform/methanol=95:5). MS-spectrum (m/e), 659 ($M^+$-61).
(B) From maytansinol and phenyl chloroformate, there is obtained maytansinol 3-phenylcarbonate. Silica gel thin layer chromatography (HPTLC): Rf=0.45 (developing solvent; chloroform/methanol=95:5). MS-spectrum, 623($M^+$-61).
(C) From dechloromaytansinol and benzyl chloroformate, there is obtained dechloromaytansinol 3-benzylcarbonate. Silica gel thin layer chromatography (HPTLC): Rf=0.54 (developing solvent: chloroform/methanol=95:5). MS-spectrum (m/e), 603 ($M^+$-61).

EXAMPLE 1

In 1 ml of pyridine are dissolved PDM-3 (100 mg, 0.16 mmole) and acetic anhydride (237 mg, 2.32 mmole), and the solution is allowed to stand at a room temperature overnight. After adding 2 ml of methanol to the solution in an ice bath, the solvent is distilled off under reduced pressure, and the residue is extracted with 100 ml of ethyl acetate. The extracted ethyl acetate layer is washed with 0.5 N HCl (ca. 20 ml) and then with 1% sodium hydrogen carbonate (ca. 20 ml), and dried over anhydrous sodium sulfate, followed by evaporating off the solvent. The resultant residue is chromatographed on a column of silica gel (20 g), and elution is carried out with 100 ml of n-hexane/ethyl acetate (1:1) and 200 ml of ethyl acetate, the eluate being collected in 20 ml fractions. The fractions No. 9 through No. 14 are pooled, concentrated under reduced pressure, and treated with petroleum ether. By the above procedure there is obtained 92 mg of PDM-3 20-acetate as white powder.

Molecular formula: $C_{33}H_{43}ClN_2O_{10}$.

Elemental analysis (%); Found C, 59.41; H, 6.73; N, 4.18. Calcd. C, 59.77; H, 6.54; N, 4.22.

UV spectrum ($\lambda_{max}^{MeOH}$) nm: 240, 249, 279.

Mass spectrum (m/e): 601, 559, 513, 498, 478, 471, 456, 436 m.p. 179°–181° C.

EXAMPLES 2 through 8

The following compounds are obtained in a similar manner to that described in Example 1.

The description will be given below in the order of, and in terms of: number of the examples of embodiment, name of the desired compounds, molecular formulas of the compounds, (1) used amount of PDM-3 (mg), (2) name of the corresponding acid anhydrides (used amount in mg), (3) used amount of pyridine, (5a) found values of elemental analysis (%) for the desired compounds, (5b) calculated values of the same, (6) UV-spectrum ($\lambda_{max}^{MeOH}$) nm of the desired compounds, and (7) mass spectrum (m/e) of the desired compounds.

EXAMPLE 2

PDM-3 20-propionate, $C_{34}H_{45}ClN_2O_{10}$, (1) 104, (2) propionic anhydride (260), (3) 2, (4) 89, (6) 240, 249, 278, (7) 615, 559, 527, 512, 492, 471, 456, 436.

EXAMPLE 3

PDM-3 20-isobutyrate, $C_{35}H_{47}ClN_2O_{10}$, (1) 101, (2) isobutyric anhydride (245), (3) 2, (4) 92, (5a) C, 60.73; H, 6.99; N, 3.91, (5b) C, 60.81; H, 6.85; N, 4.05, (6) 240, 249, 278, (7) 629, 559, 541, 526, 506, 471, 456, 436.

EXAMPLE 4

PDM-3 20-butyrate, $C_{35}H_{47}ClN_2O_{10}$, (1) 102, (2) butyric anhydride (260), (3) 2, (4) 110, (5a) C, 60.49; H, 6.98; N, 3.86, (5b) C, 60.81; H, 6.85; N, 4.05, (6) 239, 248, 278, (7) 629, 559, 541, 526, 506, 471, 456, 436.

EXAMPLE 5

PDM-3 20-isovalerate, $C_{36}H_{49}ClN_2O_{10}$, (1) 100, (2) isovaleric anhydride (240), (3) 2, (4) 91, (5a) C, 61.08; H, 7.27, N, 3.74, (5b) C, 61.31; H, 7.00; N, 3.97, (6) 240, 249, 278, (7) 643, 559, 555, 540, 520, 471, 456, 436.

EXAMPLE 6

PDM-3 20-valerate, $C_{36}H_{49}ClN_2O_{10}$, (1) 101, (2) valeric anhydride (280), (3) 2, (4), 105, (5a) C, 61.12; H, 7.26; N, 3.74, (5b) C, 61.31; H, 7.00; N, 3.97, (6) 239, 248, 278, (7) 643, 559, 555, 540, 520, 471, 456, 436.

EXAMPLE 7

PDM-3 20-crotonate, $C_{35}H_{45}ClN_2O_{10}$, (1) 100, (2) crotonic anhydride (250), (3) 2, (4) 82, (5a) C, 60.63; H, 6.81; N, 3.94, (5b) C, 60.99; H, 6.58; N, 4.07, (6) 239, 248, 280, (7) 627, 559, 539, 524, 504, 471, 456, 436.

EXAMPLE 8

PDM-3 20-benzoate, $C_{38}H_{45}ClN_2O_{10}$, (1) 100, (2) benzoic anhydride (250), (3) 2, (4) 98, (5a) C, 62.58; H, 6.47; N, 3.68, (5b) C, 62.93; H, 6.25; N, 3.86, (6) 239, 248, 280, (7) 663, 575, 560, 559, 540, 471, 456, 436.

EXAMPLE 9

In 5 ml of pyridine are dissolved PDM-3 (106 mg, 0.17 mmole) and cyclohexanecarboxylic acid (160 mg, 1.24 mmoles) and, to the solution is added dicyclohexylcarbodiimide (DCC) (260 mg, 1.26 mmoles), followed by stirring at a room temperature overnight. After evaporating off the solvent under reduced pressure, 100 ml of ethyl acetate is added and, the insolubles are filtered out. The filtrate is washed with 0.5 N hydrochloric acid (ca. 20 ml) and then with 3% sodium hydrogen carbonate (ca. 30 ml), and dried over anhydrous sodium sulfate to evaporate off the solvent. The resultant residue is chromatographed on a column of silica gel (20 g), and elution is carried out with 100 ml of n-hexane/ethyl acetate (1:1) and 200 ml of ethyl acetate, the eluate being collected in 20 ml fractions. The fractions No. 8 through No. 13 are pooled, concentrated under reduced pressure and treated with petroleum ether. By the above procedure there is obtained 111 mg of PDM-3 20-cyclohexanecarboxylate as white powder.

Molecular formula: $C_{38}H_{51}ClN_2O_{10}$.

Elemental analysis (%): Found C, 62.22; H, 7.29; N, 3.71. Calcd. C, 62.41; H, 7.03; N, 3.83.

UV spectrum ($\lambda_{max}^{MeOH}$) nm: 239, 248, 278.

Mass spectrum (m/e): 669, 581, 566, 559, 546, 471, 456, 436.

EXAMPLES 10 through 11

The following compounds are obtained in a similar manner to that described in Example 9.

The description is to be given below in the order of, and in terms of; number of the examples of embodiment, name of the desired compounds, molecular formulas of the compounds, (1) used amount of PDM-3 (mg), (2) name of the corresponding carboxylic acids (used amount in mg), (3) used amount of pyridine (ml), (4) yield of the desired compounds (mg), (5a) found values of elemental analysis (%) of the desired compounds, (5b) calculated values of the same, (6) UV spectrum of the desired compounds, and (7) mass spectrum (m/e) of the desired compounds.

EXAMPLE 10

PDM-3 20-ortho-bromobenzoate, $C_{38}H_{44}BrClN_2O_{10}$, (1) 103, (2) ortho-bromobenzoic acid (300), (3) 5, (4) 95, (5a) C, 56.31; H, 5.69; N, 3.24, (5b) C, 56.76; H, 5.52; N, 3.48, (6) 238, 248, 278. m.p. 175°–177° C.

EXAMPLE 11

PDM-3 20-phenylacetate, $C_{39}H_{47}ClN_2O_{10}$, (1) 105, (2) phenylacetic acid (190), (3) 5, (4) 57, (5a) C, 63.02; H, 6.64; N, 3.51 (5b) C, 63.36; H, 6.41; N, 3.79, (6) 239, 248, 277, (7) 677, 589, 574, 559, 554, 471, 456, 436.

EXAMPLE 12

In 5 ml of pyridine are dissolved PDM-3 (105 mg, 0.17 mmole) an picolinic acid (180 mg, 1.46 mmoles), and to the solution is added DCC (260 mg, 1.26 mmoles), followed by stirring at the room temperature overnight. The solvent is evaporated off under reduced pressure, and the residue is treated with 50 ml of ethyl acetate added to filter out the insoluble matters. The filtrate is washed with water, and dried over anhydrous sodium sulfate, followed by distilling off the solvent. The resultant residue is chromatographed on a column of silica gel (20 g), and elution is carried out with ethyl acetate, the eluate being collected in 20 ml fractions. The fractions No. 6 through No. 12 are pooled, concentrated under reduced pressure and treated with added petroleum ether. By the above procedure there is obtained 43 mg of PDM-3 20-picolinate as white powder.

Molecular formula: $C_{37}H_{44}ClN_3O_{10}$.

Elemental analysis (%): Found C, 60.77; H, 6.39; N, 5.62. Calcd. C, 61.19; H, 6.11; N, 5.79.

UV spectrum ($\lambda_{max}^{MeOH}$) nm: 231, 239, 250, 279, 290 (sh).

Mass spectrum (m/e): 664, 576, 561, 559, 541, 471, 456, 436.

EXAMPLE 13

In 3 ml of pyridine are dissolved PDM-3 (102 mg, 0.16 mmole) and phenyl isocyanate (104 mg, 0.87 mmole) and, the solution is allowed to stand at the room temperature for 3 hours. After adding 2 ml of methanol, the solvent is distilled off under reduced pressure. The residue is treated with 100 ml of ethyl acetate added to filter out the insoluble matters. The filtrate is washed with 0.5 N hydrochloric acid (ca. 20 ml) and 1% aqueous sodium hydrogen carbonate (ca. 10 ml), and dried over anhydrous sodium sulfate, followed by evaporating off the solvent. The resultant residue is chromatographed on a column of silica gel (20 g) and, elution is carried out with 100 ml of n-hexane/ethyl acetate (1:1) and 200 ml of ethyl acetate, the eluate being collected in 20 ml fractions. The fractions No. 7 through No. 10 are pooled, concentrated under reduced pressure, and treated with diethyl ether added. By the above procedure there is obtained 41 mg of PDM-3 20-phenylcarbamate as crystals. m.p. 199°–201° C.

Molecular formula: $C_{38}H_{46}ClN_3O_{10}$.

Elemental analysis (%): Found C, 61.30; H, 6.48; N, 5.43. Calcd. C, 61.66; H, 6.26; N, 5.68.

UV spectrum ($\lambda_{max}^{MeOH}$) nm: 240, 247, 278.

Mass spectrum (m/e): 678, 559, 471, 456, 436.

EXAMPLE 14

To 3 ml of pyridine in an ice bath are added PDM-3 (105 mg, 0.17 mmole) and carbobenzoxy chloride (207 mg, 1.21 mmoles) and, the mixture is allowed to stand under stirring at a room temperature overnight. After evaporating off the solvent under reduced pressure, the residue is extracted with 100 ml of ethyl acetate. The extract of ethyl acetate is washed with water and dried over anhydrous sodium sulfate, followed by distilling off the solvent. The resultant residue is chromatographed on a column of silica gel (20 g), and elution is carried out with 100 ml of n-hexane/ethyl acetate (1:1) and 200 ml of ethyl acetate, the eluate being collected in 20 ml fractions. The fractions No. 7 through No. 10 are pooled, concentrated under reduced pressure and treated with petroleum ether. By the above procedure there is obtained 49 mg of PDM-3 20-benzylcarbonate as white powder.

Molecular formula: $C_{39}H_{47}ClN_2O_{11}$.

Elemental analysis (%): Found C, 61.74; H, 6.52; N, 3.48. Calcd. C, 62.02; H, 6.27; N, 3.71.

UV spectrum ($\lambda_{max}^{MeOH}$) nm: 240, 249, 279.

Mass spectrum (m/e): 693, 559, 471, 456, 436.

EXAMPLE 15

In 1 ml of pyridine is dissolved 28 mg of dechlorodemethylmaytansinol 3-isobutyrate, and to the solution is added 0.5 ml of acetic anhydride, followed by allowing it to stand at the room temperature overnight. After evaporating off the solvent, 50 ml of ethyl acetate is added. The extract layer of ethyl acetate is washed with 0.5 N hydrochloric acid (ca. 20 ml), 1% aqueous sodium hydrogen carbonate (ca. 30 ml) and water, and dried over anhydrous sodium sulfate to evaporate off the solvent. The resultant residue is chromatographed on a column of silica gel (5 g), and elution is carried out with 40 ml of ethyl acetate. The eluate is concentrated under reduced pressure and treated with petroleum ether. By the above procedure there is obtained 22 mg of 3-isobutyryl-20-acetyldechlorodemethylmaytansinol as powder.

NMR spectrum (90 MHz, in $CDCl_3$) δ: 0.86 (3H, s), 1.20(3H, d, J=7 Hz), 1.29(6H, d, J=7 Hz), 1.71(5H, s), 2.34(3H, s), 3.22(3H, s), 3.37(3H, s), etc.

EXAMPLE 16

To a solution of 50 mg of demethylmaytansine in 1 ml of pyridine is added 0.5 ml of acetic anhydride, followed by allowing the mixture to stand at a room temperature overnight. After evaporating off the solvent under reduced pressure, 50 ml of ethyl acetate is added for extraction. The extract is washed with 0.5 N hydrochloric acid (ca. 20 ml), 1% aqueous sodium hydrogen carbonate (ca. 30 ml) and water, and dried over anhydrous sodium sulfate to distill off the solvent. The resultant residue is chromatographed on a column of silica gel (3 g), and elution is carried out with 50 ml of ethyl acetate. The eluate is concentrated under reduced pressure, and treated with added petroleum ether. By the above procedure there is obtained 43 mg of demethylmaytansine 20-acetate as powder.

NMR spectrum (90 MHz, in $CDCl_3$): 0.79(3H, s), 1.28(3H, d, J=6 Hz), 1.31(3H, d, J=7 Hz), 1.65(3H, s), 2.13(3H, s), 2.39(3H, s), 2.87(3H, s), 3.22(3H, s), 3.37(3H, s), etc.

EXAMPLE 17

To a solution of 50 mg of demethylmaytansinol 3-phenylacetate in 2 ml of pyridine is added 0.5 ml of acetic anhydride, followed by allowing the mixture to stand at the room temperature overnight. After evaporating off the solvent under reduced pressure, 100 ml of ethyl acetate is added for extraction. The extract is washed with 0.5 N hydrochloric acid (ca. 20 ml), 1% aqueous sodium hydrogen carbonate (ca. 30 ml) and water, and dried over anhydrous sodium sulfate to distill off the solvent. The resultant residue is chromatographed on a column of silica gel (5 g), and elution is carried out with 50 ml of ethyl acetate. The eluate is concentrated under reduced pressure, and treated with added petroleum ether. By the above procedure there is obtained 44 mg of 3-phenylacetyl-20-acetyldemethylmaytansinol as powder.

NMR spectrum (90 MHz, in $d_6$-DMSO) δ: 0.80(3H, s), 1.14(3H, d, J=6 Hz), 1.60(3H, s), 2.34(3H, s), 2.97(3H, s), 3.28(3H, s), 7.31(5H, s), etc.

EXAMPLE 18

To a solution of 42 mg of PDM-3 in 5 ml of dichloromethane is added 0.78 ml of dichloromethane solution containing 41 mg of 4-dimethylaminopyridine (DMAP) and 58 mg of chloroacetic anhydride, followed by stirring the solution at the room temperature for 1 hour. The reaction mixture is washed with dilute hydrochloric acid, aqueous sodium hydrogen carbonate and water in that order, and dried ($MgSO_4$) to distill off the solvent under reduced pressure. The residue is dried in vacuo, resulting in 51 mg of PDM-3 20-chloroacetate.

NMR spectrum (90 MHz, in $CDCl_3$) δ: 0.79(3H, s: 4-C$\underline{H}_3$), 1.27(6H, d, J=7 Hz; —OCOCH(C$\underline{H}_3$)$_2$), 4.38(2H, s; —OCOC$\underline{H}_2$Cl), 4.77(1H, dd, J=4 Hz and 11 Hz; 3-C$\underline{H}$), 7.16(2H, s; arom.H), etc.

EXAMPLE 19

To a solution of 11.4 mg of demethylmaytansinol in 5 ml of dichloromethane are added 14.2 mg of nicotinic acid and 31.7 mg of dicyclohexylcarbodiimide (DCC), followed by stirring the mixture at a room temperature. After 45 minutes, 9.5 mg of DMAP is added and, when further 5 hours elapse, 14.6 mg of nicotinic acid, 33.4 mg of DCC and 7.6 mg of DMAP are added, followed by stirring the mixture at a room temperature overnight. The insolubles are filtered off, and the filtrate is concentrated under reduced pressure. The residue is chromatographed on a column of silica gel (12 g of silica gel, solvent: ethyl acetate (150 ml), then ethyl acetate saturated with water (600 ml) to collect the eluate in 15 g fractions. The fractions No. 25 through No. 35 are pooled and, the solvent is distilled off. The residue is again chromatographed over silica gel [$SiO_2$: 5 g, solvent: chloroform/methanol=40/1 (v/v]. The fractions No. 5 through No. 9 are pooled, and the solvent is evaporated off, resulting in leaving 7.4 mg of demethylmaytansinol 3,20-dinicotinate. MS spectrum (m/e): 699, 594, 576, 561, 541, 471, 456.

EXAMPLE 20

In 5 ml of dichloromethane is suspended 20 mg of demethylmaytansinol, and to the suspension are added 23 mg of DMAP and 0.83 ml of a dichloromethane solution containing 62 mg of chloroacetic anhydride, followed by stirring at a room temperature. After 2 hours and 3 hours, 0.2 ml and 0.1 ml of the dichloromethane solution of chloroacetic anhydride as described above are added, respectively, and the reaction mixture is stirred for 4 hours to be allowed to stand at a room temperature overnight. It is washed with dilute hydrochloric acid, aqueous sodium hydrogen carbonate and water in that order, and dried ($MgSO_4$). The solvent is distilled off under reduced pressure and, the residue is dried in vacuo. By the above procedure there is obtained 17 mg of demethylmaytansinol, 3, 20-bis-chloroacetate.

NMR spectrum (90 MHz, in $CDCl_3$): 0.83 (3H, s: 4-C$\underline{H}_3$), 4.05 and 4.22(for each, 1H, AB quartet, $J_{AB}$=14 Hz; 3-OCOC$\underline{H}_2$Cl), 4.37(2H, s; 20-

OCOCH$_2$Cl), 7.11(1H, d, J=1.5 Hz; 17-H), 7.36(1H, d, J=1.5 Hz; 21-H).

EXAMPLE 21

In 5 ml of dry dichloromethane is suspended 25 mg of demethylmaytansinol, and to the suspension is added 0.4 ml of a dichloromethane solution containing 28 mg of DMAP and 30 mg of chloroacetic anhydride, followed by stirring at the room temperature for 1 hour. The reaction mixture is washed with dilute hydrochloric acid and aqueous sodium hydrogen carbonate, and dried (MgSO$_4$).

The solution is concentrated to dryness and, the residue is dried in vacuo, resulting in leaving 23 mg of demethylmaytansinol 20-chloroacetate.

NMR spectrum (in CDCl$_3$, δppm): 0.82(3H, s; 4-CH$_3$), 4.37(2H, s; —OCOCH$_2$Cl), 7.08(1H, d, J=1.5 Hz; 17-H), 7.37(1H, d, J=1.5 Hz; 21-H), etc.

EXAMPLE 22

In 15 ml of dry acetonitrile is dissolved 72 mg of demethylmaytansinol, and to the solution are added 135 μl of isobutyric anhydride and 76 mg of DMAP, followed by stirring at the room temperature for 30 minutes. The reaction mixture is concentrated to dryness, and the residue is dissolved in ethyl acetate and washed with dilute hydrochloric acid and, then, aqueous saturated sodium chloride, followed by drying (MgSO$_4$). The solvent is evaporated off under reduced pressure and, the residue is chromatographed over silica gel (solvent; ethyl acetate containing water), resulting in leaving 54 mg of demethylmaytansinol 20-isobutyrate.

m.p. 166°-168° C. (decomp.)(recrystallized from chloroformhexane).

NMR spectrum (in CDCl$_3$, δppm): 0.82(3H s; 4-CH$_3$), 1.35(6H, d, J=7 Hz; —OCOCH(CH$_3$)$_2$), 2.87(1H, heptad, J=7 Hz; —OCOCH(CH$_3$)$_2$), 7.00(1H, d, J=1.5 Hz; 17-H), 7.32(1H, d, J=1.5 Hz; 21-H), etc.

MS spectrum (m/e); 620, 558, 541, 552, 507.

UV spectrum ($\lambda_{max}^{MeOH}$) nm: 242, 250, 271(sh), 279(sh).

Furthermore, the fore-running fractions in the above chromatography are combined and rechromatographed (the same solvent as described above), resulting in 8 mg of the compound which is supposed to be demethylmaytansinol 3,9,20-triisobutyrate.

MS spectrum (m/e): 698, 629, 559, 541, 526.

UV spectrum ($\lambda_{max}^{MeOH}$) nm: 241, 250, 272(sh), 281(sh).

EXAMPLE 23

In 20 ml of dichloromethane is dissolved 99.8 mg of demethylmaytansinol, and to the solution are added 207 mg of benzoic anhydride, 83.7 mg of DCC and 45.6 mg of DMAP, followed by stirring at a room temperature for 140 minutes. The reaction mixture is washed with water and dried (Na$_2$SO$_4$). The solvent is distilled off under reduced pressure and, to the residue is added a small amount of ethyl acetate, then added to filter out the insoluble matters are removed by filtration. The filtrate is concentrated to dryness and, the residue is chromatographed over silica gel (solvent: chloroform/methanol=40/1 to 30/1), the eluate being collected in 25 g fractions. The fractions No. 23 through No. 77 are pooled to distill off the solvent, and the residue is reprecipitated from ethyl acetateether, resulting in leaving 78.5 mg of demethylmaytansinol 20-benzoate, m.p. 190°-191° C. (decomp.)

NMR spectrum (in CDCl$_3$) δ ppm: 0.88(3H, s; 4-CH$_3$), 7.23 and 7.38(for each, 1H, d, J=2 Hz; 17-H and 21-H), 7.45-8.29(5H, m; arom.H), etc. MS spectrum (m/e): 593, 575, 558, 497, 489, 471, 456, 455, 454.

UV spectrum ($\lambda_{max}^{MeOH}$) nm: 240, 250(sh), 272(sh), 280(sh).

EXAMPLE 24

In 0.5 ml of dry dichloromethane is dissolved 2.0 mg of demethylmaytansinol 20-benzoate, and to the solution are added 5 mg of isobutyric anhydride and 1 mg of DMAP, followed by stirring at a room temperature overnight. The reaction mixture is washed with dilute hydrochloric acid and, then, with water, and dried. After distilling off the solvent, the residue is dissolved in ethyl acetate and chlomatographed by applying to silica gel plate (Art 5717) and developing with ethyl acetate saturated with water. The spots of silica gel corresponding to Rf value of about 0.7 are scraped off and elution is carried out with dichloromethane/methanol (9/1, v/v). The results of TLC[solvent: ethyl acetate saturated with water or chloroform/methanol (9/1, v/v)] and MS spectrum measurements show that the product compound thus obtained is identical with PDM-3 20-benzoate as obtained in Example 8.

EXAMPLE 25

In 15 ml of dichloromethane is suspended 66 mg of demethylmaytansinol, and to the suspension are added dropwise 76 mg of DMAP and then a dichloromethane solution containing 207 mg of chloroacetic acid, followed by stirring at a room temperature for 3 hours. The reaction mixture is washed with dilute hydrochloric acid, aqueous sodium hydrogen carbonate and water in that order, and dried (MgSO$_4$). Evaporation of the solvent yields 83 mg of crude demethylmaytansinol, 3,20-di-chloroacetate as a white glassy substance. By subjecting the substance three times consecutively to silica-gel column chromatography (solvent: ethyl acetate containing water for the first and second operations; chloroform/methanol (=40/1) for the third operation), there are obtained 37 mg of demethylmaytansinol 3-chloroacetate and 16 mg of a mixture of demethylmaytansinol 3-chloroacetate and demethylmaytansinol 3,20-di-chloroacetate.

Typical physical properties of demethylmaytansinol 3-chloroacetate are shown below:

m.p. 190°-191° C. (decomp.)(recrystallized from chloroform).

NMR spectrum (in DMSO-d$_6$, δ ppm): 0.85(3H, s; 4-CH$_3$), 4.25 and 4.45(in total, 2H, AB quartet, J$_{AB}$=15 Hz; 3-OCOCH$_2$Cl), 6.76 and 6.91(for each, 1H, d; arom-H), 10.49(1H, s; 20-OH).

MS spectrum (m/e): 626, 565, 471, 456, 436.

EXAMPLE 26

In 5 ml of dry dichloromethane is suspended 47.7 mg of demethylmaytansinol, and to the suspension are added 50 μl of phenyl isocyanate and about 20 mg of anhydrous zinc chloride, followed by stirring at a room temperature for 20 hours. The reaction mixture is washed with water and concentrated under reduced pressure. The residue is chromatographed over 30 g of silica gel (solvent: ethyl acetate). Except the portion eluted nearly with the front end of the solvent, the fractions No. 6 through No. 11 are pooled to evaporate off the solvent, and the residue is applied to a silica gel plate (Art 5717). The development is carried out twice with ethyl acetate saturated with water. The band having the Rf value of about 0.4 to 0.5 is scraped off, and eluted with dichloromethane/methanol (=9/1, v/v). Evaporation of the solvent yields 8.6 mg of demethylmaytansinol 3-phenylcarbamate.

NMR spectrum (in CDCl$_3$ δ ppm): 0.9(3H, s; 4-C$\underline{H}_3$), 4.69(1H, dd, J=3 Hz and 11 Hz; 3-C$\underline{H}$), 6.67 and 6.89(for each, 1H, d, J=ca. 2 Hz; 17-$\underline{H}$ and 21-$\underline{H}$), 6.93–6.84(after addition of heavy water, 5H, m; arom.$\underline{H}$).

EXAMPLE 27

In 6 ml of dichloromethane is dissolved crude demethylmaytansinol 20-chloroacetate as obtained by subjecting 36 mg of demethylmaytansinol to the reaction in accordance with Example 21. After adding 85 mg of isobutyric anhydride and 24 mg of DMAP, the mixture is stirred at a room temperature for 17 hours, and an additional 33 mg of isobutyric anhydride is added, followed by stirring at the same temperature for 3 hours. Further, another 22 mg of the acid anhydride is added and the mixture is stirred at the same temperature for 3 hours. The reaction mixture is washed with dilute hydrochloric acid, aqueous sodium hydrogen carbonate and water in that order, and dried. The solvent is distilled off, and the residue is subjected to silica gel chromatography (solvent: chloroform/methanol=40/1 (v/v)). There is obtained 32 mg of a white glassy solid of the substance which is supposed to be 20-chloroacetyldemethylmaytansinol 3,9-diisobutyrate.

m.p. 162°–164° C. (decomp.)

NMR spectrum (in CDCl$_3$, δ ppm): 0.83(3H, s; 4-C$\underline{H}_3$), 1.1–1.5(m; the absorption assigned to the terminal methyl group of two —COCH(CH$_3$)$_2$ groups, and others). 4.05 and 4.22 (in total, 2H, AB quartet, J$_{AB}$=14 Hz; —OCOCH$_2$Cl), 4.98(1H, dd, J=3 Hz and 11 Hz; 3-$\underline{H}$), 6.53(1H, s; 9-N$\underline{H}$), 7.04 and 7.30(for each, 1H, d, J=1.5 Hz; arom—$\underline{H}$).

MS spectrum (m/e): 704, 696, 634, 632, 602, 555, 541, 525, 523.

UV spectrum ($\lambda_{max}^{MeOH}$) nm: 242, 250.5, 271(sh), 280(sh).

EXAMPLE 28

In 5 ml of dichloromethane is dissolved 27 mg of demethylmaytansinol 20-benzoate, and to the solution are added 7 μl of phenyl isocyanate and 13 mg of anhydrous zinc chloride. Following stirring at the room temperature for 1 hour, additionally 5 μl of phenyl isocyanate and 10 mg of anhydrous zinc chloride are added, and the mixture is stirred at a room temperature for further 5.5 hours. The reaction mixture is washed with water, dried and chromatographed over silica gel (SiO$_2$: 40 g; solvent: ethyl acetate/ethyl acetate saturated with water (=3/1, v/v)), the eluate being collected in 20 g fractions. The fractions No. 11 through No. 19, and the solvent is distilled off, resulting in 16 mg of 3-N-phenylcarbamoyldemethylmaytansinol 20-benzoate.

NMR spectrum (in CDCl$_3$, δ ppm): 0.89(3H, s; 4-C$\underline{H}_3$), 4.74(1H, dd, J=3 Hz and 13 Hz; 3-$\underline{H}$), 7.0–7.8 and 8.19–8.26(10H, m; arom-$\underline{H}$).

EXAMPLE 29

In 3 ml of dichloromethane is dissolved 27.9 mg of demethylmaytansinol 20-benzoate and, to the solution under stirring, at the intervals of 30 minutes, are added the following amounts of DCC, N-acetyl-N-methyl-D,L-alanine and anhydrous zinc chloride in three parts as being given in that order: (1) 33.6 mg, 16.6 mg, 6 mg, (2) 21.7 mg, 16.4 mg, 6 mg, and (3) 19.8 mg, 11.6 mg, 6 mg. After the final addition, stirring is continued for further 30 minutes, and the reaction mixture is filtered to remove the insolubles. The filtrate is concentrated, and the residue is again dissolved in a small amount of ethyl acetate, then insolubles are recovered by filtration. The filtrate is washed with water and dried (Na$_2$SO$_4$), followed by distilling off the solvent. The residue is chromatographed over silica gel (SiO$_2$: 40 g; solvent: chloroform (=40/1, v/v)) and, the eluate is collected in 20 ml fractions. The fractions No. 15 through No. 25 are pooled, and after distilling off the solvent, the residue is again chromatographed on silica gel (SiO$_2$: 25 g; solvent: ethyl acetate saturated with water), the eluate being collected in 20 ml fractions. The fractions No. 9 through No. 18 are pooled, and the solvent is distilled off, yielding 15.8 mg of demethylmaytansine 20-benzoate (compound A), whereas the fractions No. 19 through No. 35, when treated in a similar manner, produces 16.8 mg of the substance which is supposed to be demethyl-D-maytansine 20-benzoate (compound B).

NMR spectrum (in CDCl$_3$, δ ppm): The compound A: 0.83(3H, s; 4-C$\underline{H}_3$), 2.14(3H, s; —COC$\underline{H}$(CH$_3$)N(CH$_3$)—COCH$_3$), 4.74(1H, dd, J=3 Hz and 11 Hz; 3-$\underline{H}$), 5.41 (1H, q, J=7 Hz; —COC$\underline{H}$(CH$_3$)—N(CH$_3$)—COCH$_3$), 7.47–7.74 and 8.19–8.28(in total, 5H, m; arom-$\underline{H}$).

The compound B: 0.89(3H, s; 4-C$\underline{H}_3$), 2.16(3H, s; —COC$\underline{H}$(CH$_3$)—N(CH$_3$)—COCH$_3$), 4.88(1H, dd, J=3 Hz and 11 Hz; 3-$\underline{H}$), 5.04 (1H, q, J=7 Hz; —COC$\underline{H}$(CH$_3$)—N(CH$_3$)—COCH$_3$), 7.47–7.74 and 8.19–8.28(in total, 5H, m; arom-$\underline{H}$).

EXAMPLE 30

Dechlorodemethylmaytansinol (39 mg), isobutyric anhydride (50 mg) and DMAP (40 mg) are mixed in 5 ml of dry dichloromethane and the mixture is stirred at room temperature. After 2.5 hours stirring, isobutyric anhydride (30 mg) is further added and the mixture is stirred at room temperature for 2 days.

The reaction mixture is washed with diluted sulfuric acid, aqueous sodium bicarbonate solution and water, successively, and then dried (Mg$_2$SO$_4$). Evaporation of the solvent yields 44 mg of the crude reaction product, which is chromatographed on a silica gel column [20 mm (diam.)×300 mm (length)] with a mixture of chloroform/methanol=100/1 (v/v). The eluate is collected in 25-g fractions. From fractions 23-35, 23 mg of dechlorodemethylmaytansinol 3,20-di-isobutyrate is obtained.

m.p.: 156°–158° C. (recrystallized from chloroform-hexane).

MS-spectrum (m/e): 656 (M+), 594, 592

EXAMPLE 31

PDM-3 (106.1 mg), phenyl chloroformate (166 mg) are dissolved in 5 ml of dry dichloromethane. To this, 0.1 N NaOH (10.5 ml) and cetyltrimethylammonium bromide (124.5 mg) are added and the mixture is stirred at room temperature for 30 minutes. Some saturated aqueous solution of NaCl is added and the aqueous phase separated is discarded. The organic phase is washed once more with an aqueous NaCl solution, dried (Na$_2$SO$_4$) and then evaporated to dryness. The residue is triturated with ethyl acetate and insolubles are filtered off. The filtrate is concentrated and chromatographed on a column of silica gel (40 g) with ethyl acetate, collecting 17 g fractions. Fractions 8 and 9 are combined and the solvent is evaporated to give 77.7 mg of PDM-3 20-phenylcarbonate.

m.p.: 173°–175° C.(decomp.).

EXAMPLE 32

In 1 ml of pyridine are dissolved PDM-3 (50 mg) and succinic anhydride (50 mg), and the solution is allowed to stand at room temperature overnight. The reaction mixture is washed with diluted hydrochloric acid and water, successively, and then dried ($Na_2SO_4$). Evaporation of the solvent yields 58 mg of the crude reaction product, which is chromatographed on a silica gel column [15 mm (diam.)×200 mm (length)] with a mixture of chloroform/methanol=25/1 (v/v). The eluate is collected in 15 g fractions. From fractions 12–16, 26 mg of PDM-3 20-succinic acid half ester is obtained. The Rf value is 0.27 [developing solvent: $CHCl_3/MeOH=9/1$; silica gel glass plate (Merck 60 $F_{254}$, thickness of 0.25 mm)].

What we claim is:

1. A compound of the formula:

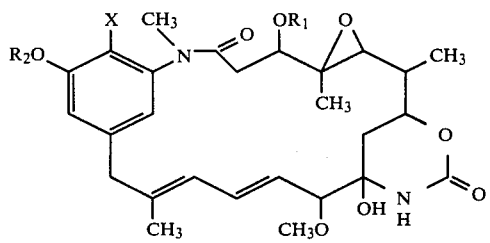

wherein X is chlorine or hydrogen, $R_1$ is hydrogen or acyl; $R_2$ is acyl; said acyl being represented by the formula:

$$-CO-R_3 \qquad (a)$$

wherein $R_3$ is hydrogen, $C_{1-18}$ alkyl, $C_{2-18}$ alkenyl, $C_{3-10}$ cycloalkyl, $C_{3-10}$ cycloalkenyl, heterocyclic group selected from the group consisting of azetidinyl, 2-pyridyl, 3-pyridyl, 4-pyridyl, 1,2,3,4-tetrahydropyridyl, piperidyl, quinolyl, 1,2-dihydroquinolyl, 3-isoquinolyl, 4-isoquinolyl, 1,2-dihydroisoquinolyl, pyrrolyl, pyrrolinyl, pyrrolidinyl, indolyl, furyl, pyranyl, dihydropyranyl, benzofuryl, benzopyranyl, thienyl, benzothienyl, imidazolyl, pyrazolyl, pyrazinyl, pyrimidinyl, pyridazinyl, 2-imidazolyl, imidazolidinyl, benzoimidazolyl, indazolyl, quinoxalyl, quinazolinyl, cinnolinyl, 1,4-dioxanyl 1,4-benzodioxanyl, 1,2-dithiolanyl, 1,3-dithiolanyl, 1,3-dithianyl, isooxazolyl, oxazolyl, morpholinyl, benzoisoxazolyl benzoxazolyl, isothiazolyl, thiazolyl, benzoisothiazolyl, benzothiazolyl, benzothiazinyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,5-triazolyl, 1,3,4-triazolyl, 1,3,5-triadinyl, benzotriazolyl and 1,2,3,4-tetrazolyl, said cycloalkyl, cycloalkenyl, phenyl or heterocyclic group being attached directly to the carbonyl carbon or through a $C_{1-4}$ alkylene chain, said alkyl, alkenyl, cycloalkyl, cycloalkenyl, phenyl or heterocyclic group being unsubstituted or substituted by $C_{1-4}$ alkoxy, $C_{2-4}$ alkanoyl, $C_{2-4}$ alkanoyloxy, $C_{2-4}$ alkanoyl, $C_{2-4}$ alkanoyloxy, $C_{2-4}$ alkoxycarbonyl, halogen, nitro, cyano, trifluoromethyl, di-$C_{1-4}$-alkylamino, $C_{1-4}$ alkylthio methylsulfinyl, methylsulfonyl, oxo, thioxo, $C_{1-4}$ alkanoylamido or carboxy group of the formula -$COOR_{12}$ wherein $R_{12}$ is hydrogen, $C_{1-6}$ alkyl, phenyl or benzyl, and said cycloalkyl, cycloalkenyl, phenyl or heterocyclic group being unsubstituted or substituted by $C_{1-4}$ alkyl;

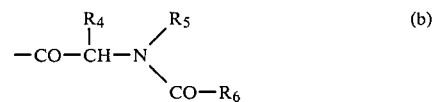

wherein $R_4$ is hydrogen, $C_{1-18}$ alkyl, $C_{3-10}$ cycloalkyl, phenyl, indolyl or imidazolyl group, said cycloalkyl, phenyl, indolyl or imidazolyl groups being attached directly to the alpha-carbon atom or, through a $C_{1-4}$ alkylene chain, said alkyl, cycloalkyl, phenyl, indolyl or imidazolyl being unsubstituted or substituted by $C_{1-4}$ alkoxy, $C_{2-4}$ alkanoyl, $C_{2-4}$ alkanoyloxy, $C_{2-4}$ alkoxycarbonyl, halogen, nitro, cyano, trifluoromethyl, di-$C_{1-4}$-alkylamino, $C_{1-4}$ alkylthio, methylsulfinyl, methylsulfonyl, oxo, thioxo or $C_{1-4}$ alkanoylamido, and said cycloalkyl, phenyl, indolyl or imidazolyl being unsubstituted or substituted by $C_{1-4}$ alkyl; $R_5$ is hydrogen, $C_{1-18}$ alkyl, $C_{3-10}$ cycloalkyl, $C_{4-14}$ cycloalkylalkyl, phenyl or benzyl group, said alkyl, cycloalkyl, cycloalkylalkyl, phenyl or benzyl group being unsubstituted or substituted by $C_{1-4}$ alkoxy, $C_{2-4}$ alkanoyl, $C_{2-4}$ alkanoyloxy, $C_{2-4}$ alkoxycarbonyl, halogen, nitro, cyano, trifluoromethyl, di-$C_{1-4}$-alkylamino, $C_{1-4}$ alkylthio, methylsulfinyl, methylsulfonyl, oxo, thioxo or $C_{1-4}$ alkanoylamido, and said cycloalkyl cycloalkylalkyl, phenyl or benzyl group being unsubstituted or substituted by $C_{1-4}$ alkyl; $R_6$ is hydrogen, $C_{1-7}$ alkoxy, bornyloxy, isobornyloxy, benzyloxy, $C_{1-18}$ alkyl, $C_{2-18}$ alkenyl, $C_{3-10}$ cycloalkyl, $C_{3-10}$ cycloalkenyl, phenyl or heterocyclic group selected from the group consisting of azetidinyl, 2-pyridyl, 3-pyridyl, 4-pyridyl, 1,2,3,4-tetrahydropyridyl, piperidyl, quinolyl, 1,2-dihydroquinolyl, 3-isoquinolyl, 4-isoquinolyl, 1,2-dihydroisoquinolyl, pyrrolyl, pyrrolinyl, pyrrolidinyl, indolyl, furyl, pyranyl, dihydropyranyl, benzofuryl, benzopyranyl, thienyl, benzothienyl, imidazolyl, pyrazolyl, pyrazinyl, pyrimidinyl, pyridazinyl, 2-imidazolyl, imidazolidinyl, benzoimidazolyl, indazolyl, quinoxalyl, quinazolinyl, cinnolinyl, 1,4-dioxanyl, 1,4-benzodioxanyl, 1,2-dithiolanyl, 1,3-dithiolanyl, 1,3-dithianyl, isooxazolyl, oxazolyl, morpholinyl, benzoisoxazolyl, benzoxazolyl, isothiazolyl, thiazolyl, benzoisothiazolyl, benzothiazolyl, benzothiazinyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,5-triazolyl, 1,3,4-triazolyl, 1,3,5-triadinyl, benzotriazolyl and 1,2,3,4-tetrazolyl, said cycloalkyl, cycloalkenyl, phenyl or heterocyclic groups being attached directly to the carbonyl carbon atom adjacent the nitrogen atom or through a $C_{1-4}$ alkylene chain, said alkyl, alkenyl, cycloalkyl, cycloalkenyl, phenyl or heterocyclic group being unsubstituted or substituted by $C_{1-4}$ alkoxy, $C_{2-4}$ alkanoyl, $C_{2-4}$ alkanoyloxy, $C_{2-4}$ alkoxycarbonyl, halogen, nitro, cyano, trifluoromethyl, di-$C_{1-4}$-alkylamino, $C_{1-4}$ alkylthio, methylsulfinyl, methylsulfonyl, oxo, thioxo or $C_{1-4}$ alkanoylamido, and said cycloalkyl, cycloalkenyl, phenyl or heterocyclic group being unsubstituted or substituted by $C_{1-4}$ alkyl;

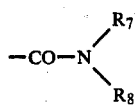

wherein $R_7$ and $R_8$ may be the same or different and each is hydrogen, $C_{1-18}$ alkyl, $C_{2-18}$ alkenyl, $C_{3-10}$ cycloalkyl, $C_{3-10}$ cycloalkenyl, $C_{4-14}$ cycloalkylalkyl, $C_{4-10}$ cycloalkenylalky phenyl, phenyl-$C_{1-4}$-alkyl, phenyl-$C_{3-10}$-cycloalkyl, $C_{3-10}$ cycloalkylphenyl, biphenyl or heterocyclic group selected from the group consisting of azetidinyl, pyrrolyl, furyl, thienyl, thiazolyl, isothiazolyl, oxazolyl, isoxazolyl, pyrazolyl, imidazolyl, pyridyl, pyrimidinyl, pyrazinyl, triazinyl, quinolyl, quinazolyl, quinoxalyl, indolyl, benzofuranyl and benzothienyl, and wherein $R_7$ and $R_8$ together may form a heterocyclic group of azetidinyl, pyrrolidinyl, piperadinyl or morpholinyl taken together with the adjacent nitrogen atom, these groups being unsubstituted or substituted by $C_{1-4}$ alkoxy, $C_{1-4}$ alkylthio, phenoxy, phenylthio, cyclohexyloxy, halogen, cyano, $C_{2-5}$ alkoxycarbonyl, benzyloxycarbonyl, nitro, aminosulfonyl or di-$C_{1-4}$-alkylamino, and said cyclic moiety or heterocyclic group being unsubstituted or substituted by $C_{1-4}$ alkyl; or

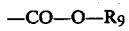  (d)

wherein $R_9$ is $C_{1-18}$ alkyl, $C_{3-10}$ cycloalkyl, phenyl or phenyl-$C_{1-4}$-alkyl, said groups being unsubstituted or substituted by $C_{1-4}$ alkoxy, phenoxy, benzyloxy, halogen or cyano, and said cyclic moiety being unsubstituted or substituted by $C_{1-4}$ alkyl.

2. A compound as claimed in claim 1, wherein $R_1$ and $R_2$ may be the same or different and each is acyl represented by the formula:

wherein $R_3$ is hydrogen or $C_{1-6}$ alkyl, $C_{2-4}$ alkenyl, $C_{3-10}$ cycloalkyl, phenyl or 2-, 3- or 4-pyridyl, said group being unsubstituted or substituted by halogen or carboxy or attached directly to the carbonyl carbon or through a $C_{1-4}$ alkylene chain; acyl represented by the formula:

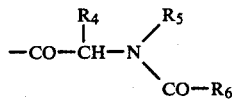

wherein $R_4$, $R_5$ and $R_6$ may be the same or different and each is hydrogen or $C_{1-6}$ alkyl; acyl represented by the formula

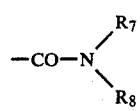

wherein $R_7$ and $R_8$ may be the same or different and each is hydrogen or phenyl; or acyl represented by the formula:

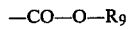

wherein $R_9$ is phenyl or benzyl.

3. A compound as claimed in claim 2, wherein each of $R_1$ and $R_2$ is independently

—CO—$R_3$ wherein $R_3$ is hydrogen, $C_{1-6}$ alkyl, $C_{2-4}$ alkenyl, $C_{3-10}$ cycloalkyl, phenyl or 2-, 3- or 4-pyridyl, each $R_3$ group being unsubstituted or substituted by halogen carboxy or attached directly to the carbonyl carbon or through a $C_{1-4}$ alkylene chain.

4. A compound as claimed in claim 2 wherein $R_1$ is:

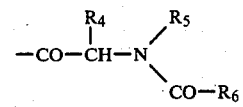

wherein each of $R_4$, $R_5$ and $R_6$ is independently hydrogen or $C_{1-6}$ alkyl.

5. A compound as claimed in claim 2 wherein $R_1$ is:

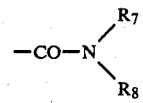

wherein each of $R_7$ and $R_8$ is independently hydrogen or phenyl.

6. A compound as claimed in claim 2 wherein $R_1$ is:

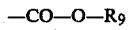

wherein $R_9$ is phenyl or benzyl.

7. A compound as claimed in claim 1, wherein $R_1$ is

wherein $R_3'$ is $C_{1-6}$ alkyl.

8. A compound as claimed in claim 1, wherein $R_1$ is

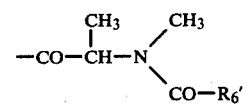

wherein $R_6'$ is $C_{1-6}$ alkyl.

9. A compound as claimed in claim 1, wherein the compound is 20-acetyl-3-isobutyryl-20-demethoxy-20-hydroxymaytansinol.

10. A compound as claimed in claim 1, wherein the compound is 3-isobutyryl-20-propionyl-20-demethoxy-20-hydroxymaytansinol.

11. A compound as claimed in claim 1, wherein the compound is 3,20-diisobutyryl-20-demethoxy-20-hydroxymaytansinol.

12. A compound as claimed in claim 1, wherein the compound is 20-butyryl-3-isobutyryl-20-demethoxy-20-hydroxymaytansinol.

13. A compound as claimed in claim 1, wherein the compound is 3-isobutyryl-20-isovaleryl-20-demethoxy-20-hydroxymaytansinol.

14. A compound as claimed in claim 1, wherein the compound is 3-isobutyryl-20-valeryl-20-demethoxy-20-hydroxymaytansinol.

15. A compound as claimed in claim 1, wherein the compound is 20-crotonyl-3-isobutyryl-20-demethoxy-20-hydroxymaytansinol.

16. A compound as claimed in claim 1, wherein the compound is 20-benzoyl-3-isobutyryl-20-demethoxy-20-hydroxymaytansinol.

17. A compound as claimed in claim 1, wherein the compound is 20-cyclohexylcarbonyl-3-isobutyryl-20-demethoxy-20-hydroxymaytansinol.

18. A compound as claimed in claim 1, wherein the compound is 20-ortho-bromobenzyl-3-isobutyryl-20-demethoxy-20-hydroxymaytansinol.

19. A compound as claimed in claim 1, wherein the compound is 3-isobutyryl-20-phenylacetyl-20-demethoxy-20-hydroxymaytansinol.

20. A compound as claimed in claim 1, wherein the compound is 3-isobutyryl-20-picolinyl-20-demethoxy-20-hydroxymaytansinol.

21. A compound as claimed in claim 1, wherein the compound is 3-isobutyryl-20-phenylcarbamoyl-20-demethoxy-20-hydroxymaytansinol.

22. A compound as claimed in claim 1, wherein the compound is 20-benzyloxycarbonyl-3-isobutyryl-20-demethoxy-20-hydroxymaytansinol.

23. A compound as claimed in claim 1, wherein the compound is 20-acetyl-3-isobutyryl-20-demethoxy-20-hydroxy-19-dechloromaytansinol.

24. A compound as claimed in claim 1, wherein the compound is 20-acetyl-20-demethoxy-20-hydroxymaytansine.

25. A compound as claimed in claim 1, wherein the compound is 20-acetyl-3-phenylacetyl-20-demethoxy-20-hydroxymaytansinol.

26. A compound as claimed in claim 1, wherein the compound is 20-chloroacetyl-3-isobutyryl-20-demethoxy-20-hydroxymaytansinol.

27. A compound as claimed in claim 1, wherein the compound is 3,20-nicotinoyl-20-demethoxy-20-hydroxymaytansinol.

28. A compound as claimed in claim 1, wherein the compound is 3,20-dichloroacetyl-20-demethoxy-20-hydroxymaytansinol.

29. A compound as claimed in claim 1, wherein the compound is 20-chloroacetyl-20-demethoxy-20-hydroxymaytansinol.

30. A compound as claimed in claim 1, wherein the compound is 20-isobutyryl-20-demethoxy-20-hydroxymaytansinol.

31. A compound as claimed in claim 1, wherein the compound is 20-benzoyl-20-demethoxy-20-hydroxymaytansinol.

32. A compound as claimed in claim 1, wherein the compound is 20-benzoyl-3-N-phenylcarbamoyl-20-demethoxy-20-hydroxymaytansinol.

33. A compound as claimed in claim 1, wherein the compound is 20-benzoyl-20-demethoxy-20-hydroxymaytansine.

34. A compound as claimed in claim 1, wherein the compound is 20-benzoyl-20-demethoxy-20-hydroxy-D-maytansine.

35. A compound as claimed in claim 1, wherein the compound is 3,20-diisobutyryl-20-demethoxy-20-hydroxy-19-dechloromaytansinol.

36. A compound as claimed in claim 1, wherein the compound is 20-phenoxycarbonyl-20-demethoxy-20-hydroxymaytansinol.

37. A compound as claimed in claim 1, wherein the compound is 20-(3'-carboxypropionyl)-3-isobutyryl-20-demethoxy-20-hydroxymaytansinol.

* * * * *